United States Patent
Singh et al.

(10) Patent No.: US 7,217,531 B2
(45) Date of Patent: May 15, 2007

(54) MULTIPLEX ANALYSIS USING MEMBRANE-BOUND SENSITIZERS

(75) Inventors: Sharat Singh, San Jose, CA (US); Po-Ying Chan-Hui, Oakland, CA (US); Hrair Kirakossian, San Jose, CA (US)

(73) Assignee: Monogram Biosciences, South San Francisco, CA (US)

( * ) Notice: Subject to any disclaimer, the term of this patent is extended or adjusted under 35 U.S.C. 154(b) by 0 days.

(21) Appl. No.: 11/214,234

(22) Filed: Aug. 27, 2005

(65) Prior Publication Data
US 2006/0024846 A1   Feb. 2, 2006

Related U.S. Application Data

(62) Division of application No. 10/379,965, filed on Mar. 4, 2003, now Pat. No. 6,949,347.

(60) Provisional application No. 60/440,838, filed on Jan. 17, 2003, provisional application No. 60/361,975, filed on Mar. 5, 2002.

(51) Int. Cl.
*G01N 33/53* (2006.01)

(52) U.S. Cl. .................. 435/7.1; 435/7.2; 435/7.8; 436/8; 436/518

(58) Field of Classification Search .............. 436/8, 436/518; 435/7.1, 7.2, 7.8
See application file for complete search history.

(56) References Cited

U.S. PATENT DOCUMENTS

| | | | |
|---|---|---|---|
| 4,331,590 A | 5/1982 | Bocuslaski | 260/112 B |
| 4,650,750 A | 3/1987 | Giese | 435/7 |
| 4,709,016 A | 11/1987 | Giese | 530/389 |
| 4,780,421 A | 10/1988 | Kameda | 436/518 |
| 5,292,414 A | 3/1994 | Sessler | 204/157.5 |
| 5,340,716 A | 8/1994 | Ullman | 435/6 |
| 5,344,928 A | 9/1994 | Masuya | 544/37 |
| 5,360,819 A | 11/1994 | Giese | 514/538 |
| 5,470,705 A | 11/1995 | Grossman | 435/6 |
| 5,494,793 A | 2/1996 | Schindele | 435/6 |

(Continued)

FOREIGN PATENT DOCUMENTS

| WO | WO 99/42838 | 8/1999 |
|---|---|---|
| WO | WO 00/66607 | 11/2000 |

OTHER PUBLICATIONS

Rios et al., G-protein-coupled receptor dimerization: modulation of receptor function, Pharmacology & Therapeutics, vol. 92, (2000), pp. 71-87.*

(Continued)

*Primary Examiner*—Christopher R. Tate
*Assistant Examiner*—Deborah A. Davis
(74) *Attorney, Agent, or Firm*—Fenwick & West LLP

(57) ABSTRACT

The present invention is directed to methods and compositions for determining the presence, absence, and/or amounts of one or more membrane-associated analytes in a sample. In accordance with the invention, binding compounds derivatized with releasable molecular tags specifically bind to selected membrane-associated analytes, after which the molecular tags are released upon activation of cleavage moieties, or sensitizers, anchored in the same membrane as the membrane-associated analytes. The released molecular tags are then identified by their distinct separation and detection characteristics.

6 Claims, 50 Drawing Sheets

U.S. PATENT DOCUMENTS

| | | | | |
|---|---|---|---|---|
| 5,514,543 | A | 5/1996 | Grossman | 435/6 |
| 5,516,636 | A | 5/1996 | McCapra | 435/6 |
| 5,516,931 | A | 5/1996 | Giese | 560/59 |
| 5,532,171 | A | 7/1996 | Motsenbocker | 436/533 |
| 5,536,834 | A | 7/1996 | Singh | 544/98 |
| 5,565,324 | A | 10/1996 | Still | 435/6 |
| 5,578,498 | A | 11/1996 | Singh | 436/518 |
| 5,580,732 | A | 12/1996 | Grossman | 435/6 |
| 5,602,273 | A | 2/1997 | Giese | 560/60 |
| 5,604,104 | A | 2/1997 | Giese | 435/7.1 |
| 5,610,020 | A | 3/1997 | Giese | 435/7.1 |
| 5,616,719 | A | 4/1997 | Davalian | 546/334 |
| 5,622,929 | A | 4/1997 | Willner | 514/8 |
| 5,624,800 | A | 4/1997 | Grossman | 435/6 |
| 5,650,270 | A | 7/1997 | Giese | 435/6 |
| 5,703,222 | A | 12/1997 | Grossman | 536/24.3 |
| 5,705,622 | A | 1/1998 | McCapra | 536/23.1 |
| 5,709,994 | A | 1/1998 | Pease | 435/4 |
| 5,721,099 | A | 2/1998 | Still | 435/6 |
| 5,756,726 | A | 5/1998 | Hemmi | 540/474 |
| 5,766,481 | A | 6/1998 | Zambias | 210/656 |
| 5,777,096 | A | 7/1998 | Grossman | 536/24.3 |
| 5,789,172 | A | 8/1998 | Still | 435/6 |
| 5,800,999 | A | 9/1998 | Bronstein | 435/6 |
| 5,807,675 | A | 9/1998 | Davalian | 435/6 |
| 5,807,682 | A | 9/1998 | Grossman | 435/6 |
| 5,843,655 | A | 12/1998 | McGall | 435/6 |
| 5,843,666 | A | 12/1998 | Akhavan-Tafti | 435/6 |
| 5,846,839 | A | 12/1998 | Gallop | 436/518 |
| 5,898,005 | A | 4/1999 | Singh | 436/527 |
| 5,952,654 | A | 9/1999 | Giese | 250/288 |
| 5,989,871 | A | 11/1999 | Grossman | 435/91.1 |
| 6,001,579 | A | 12/1999 | Still | 435/7.1 |
| 6,004,530 | A | 12/1999 | Sanger | 424/1.65 |
| 6,027,890 | A | 2/2000 | Ness | 435/6 |
| 6,251,581 | B1 | 6/2001 | Ullman | 435/4 |
| 6,312,893 | B1 | 11/2001 | Van Ness | 435/6 |
| 6,322,980 | B1 | 11/2001 | Singh | 435/6 |
| 6,331,530 | B1 | 12/2001 | Breslow | 514/58 |
| 6,340,599 | B1 | 1/2002 | Singh | 436/534 |
| 6,346,384 | B1 | 2/2002 | Pollner | 435/6 |
| 6,346,529 | B1 | 2/2002 | Floyd | 514/226.2 |
| 6,375,930 | B2 | 4/2002 | Young | 424/9.362 |
| 6,545,102 | B1* | 4/2003 | Akhavan-Tafti et al. | 525/340 |
| 6,627,400 | B1* | 9/2003 | Singh et al. | 435/6 |
| 2002/0006378 | A1 | 1/2002 | Young | 424/1.11 |

OTHER PUBLICATIONS

Gomes et al., G protein coupled receptor dimerization: implications in modulating receptor function, J. Mol Medicine (2000), vol. 79, pp. 226-242.*

Bosse et al., "Principles of AlphaScreen Amplified Luminescent Proximity Homogeneous Assay", AlphaScreen Technology, Application Note ASC-001, Packard BioScience, BioSignal Packard Inc.

Giese, "Electrophoric Release Tags: Ultrasensitive Molecular Labels Providing Multiplicity", Trends in Analytical Chemistry, vol. 2, No. 7, 1983, pp. 166-168.

Gomer, "Preclinical Examination of First and Second Generation Photosensitizers Used in Photodynamic Therapy", Photochemistry and Photobiology, vol. 54, No. 6, 1991, pp. 1093-1107.

Lum et al., "Ability of Specific Monoclonal Antibodies and Conventional Antisera Conjugated to Hematoporphyrin to Label and Kill Selected Cell Lines Subsequent to Light Activation", Cancer Research, vol. 45, 1985, pp. 4380-4386.

Oseroff et al., "Antibody-Targeted Photolysis: Selective Photodestruction of Human T-Cell Leukemia Cells Using Monoclonal Antibody-Chlorin $e_6$ Conjugates", Proc. Natl. Acad. Sci. USA, vol. 83, 1986, pp. 8744-8748.

Pierlot, Christel et al., "Naphthalene Endoperoxides as Generators of Singlet Oxygen in Biological Media", Methods in Enzymology, vol. 319, 2000.

Rakestraw et al., "Antibody-Targeted Photolysis: In vitro Studies with Sn(IV) Chlorin $e_6$ Covalently Bound to Monoclonal Antibodies Using a Modified Dextran Carrier" Proc. Natl. Acad. Sci. USA, vol. 87, 1990, pp. 4217-4221.

Sharman et al., "Role of Activated Oxygen Species in Photodynamic Therapy", Methods in Enzymology, vol. 319, 2000, pp. 376-400.

Strong et al., "Antibody-Targeted Photolysis" Annals New York Academy of Sciences, vol. 745, 1994, pp. 297-320.

Ullman, Edwin F. et al., "Luminescent oxygen channeling immunoassay: Measurement of particle binding kinetics by chermiluminescence", Proc. Natl. Acad. Sci. USA, vol. 91, Jun. 1994, pp. 5426-5430.

Yarmush et al., "Antibody Targeted Photolysis", Critical Reviews in Theraputic Drug Carrier Systems, vol. 10, 1993, pp. 197-252.

Yemul et al., "Selective Killing of T Lymphocytes by Phototoxic Liposomes", Proc. Natl. Acad. Sci. USA, vol. 84, 1987, pp. 246-250.

Beaudet et al., "Homogeneous Assays for Single-Nucleotide Polymorphism Typing Using AlphaScreen", Genome Research, 11:600-608, 2001.

BioSignal, "Whole Cell camp Functional Assay", AlphaScreen, Technical Note AN002-Asc, Packard Instrument Company.

* cited by examiner

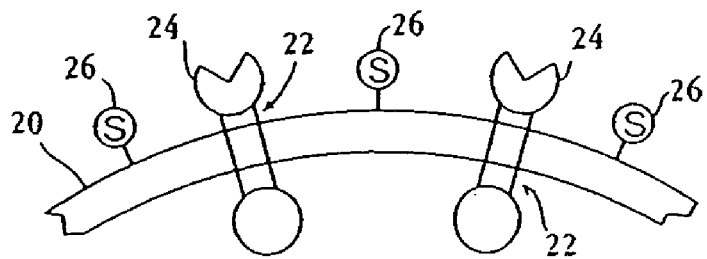
Fig. 1H
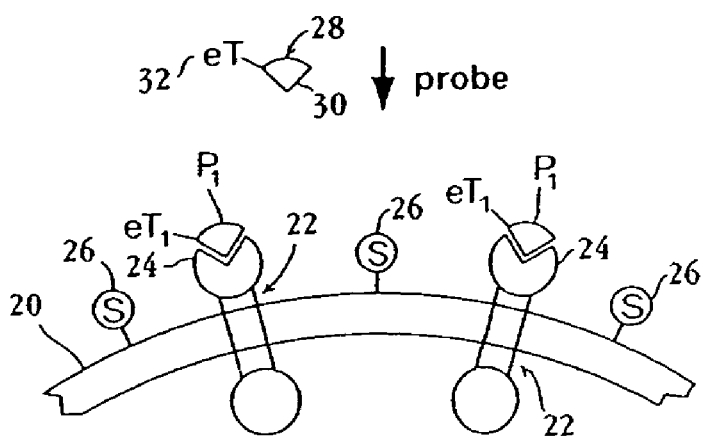
Fig. 1I
Fig. 1J
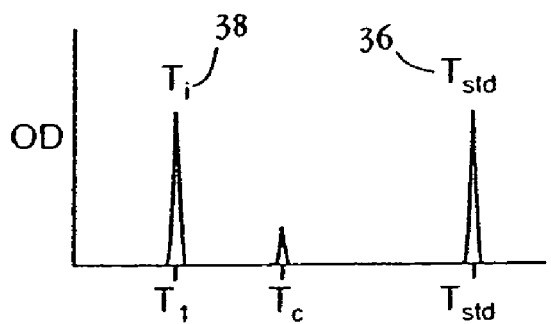
Fig. 1K

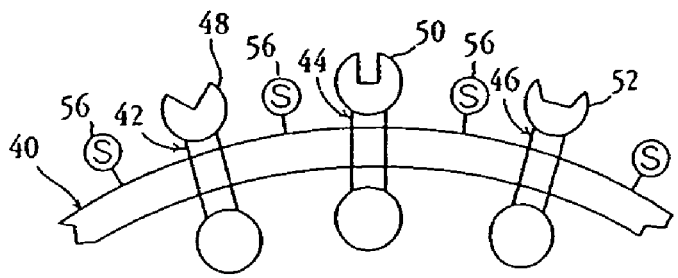
Fig. 1L
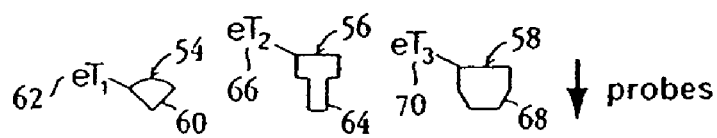
↓ probes
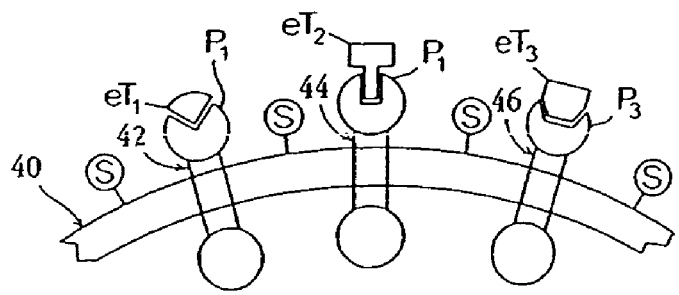
Fig. 1M
↓ hν
Fig. 1N
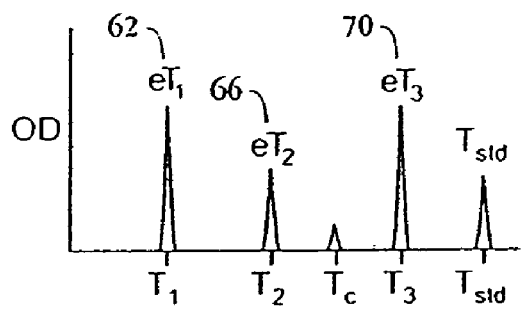
Fig. 1O Thiazole cleavable linkage Oxazole cleavable linkage

Olefin cleavable linkage

Thioether cleavable linkage

Synthesis of FAM-derived eTags

Pro1-NHS

Pro2-NHS

Pro3-NHS

Pro4-NHS

Pro5-NHS

Pro6-NHS

Pro7-NHS

Pro8-NHS

Pro9-NHS

Pro10-NHS

Pro11-NHS

Pro12-NHS

Pro13-NHS

Pro14-NHS

Pro15-NHS

Pro16-NHS

Pro17-NHS

Pro18-NHS

Pro19-NHS

Pro20-NHS

Pro21-NHS

Pro22-NHS

Pro23-biotin

Pro24-biotin

Pro25-biotin

Pro26-biotin

Pro27-biotin

Pro28-NHS

Pro28-biotin

Pro29-NHS

Pro29-biotin

Pro30-NHS

Pro30-biotin

Pro31-NHS

Pro32-NHS

Pro32-biotin

Pro33-NHS

Pro33-biotin

Synthesis of Pro28

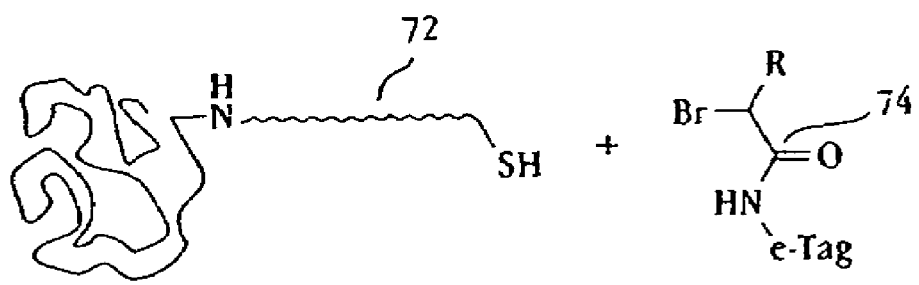
Fig. 11A
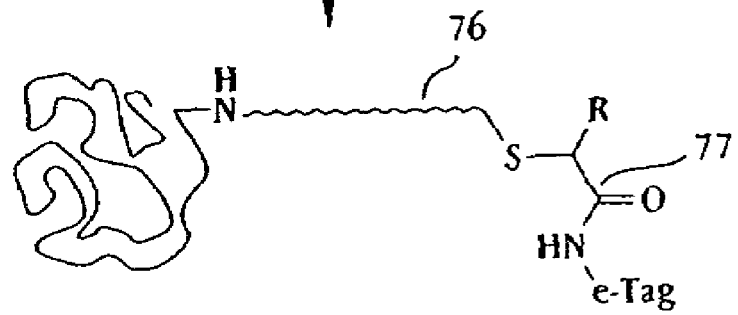
Fig. 11B
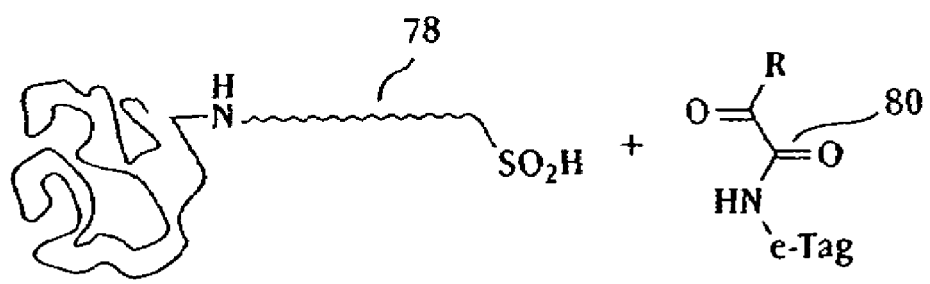
Fig. 11C
R=CONR$_2$, (R=H, Me)
R=Phenyl
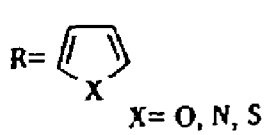
X= O, N, S
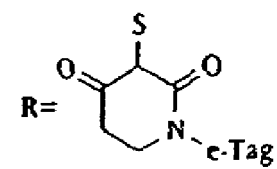

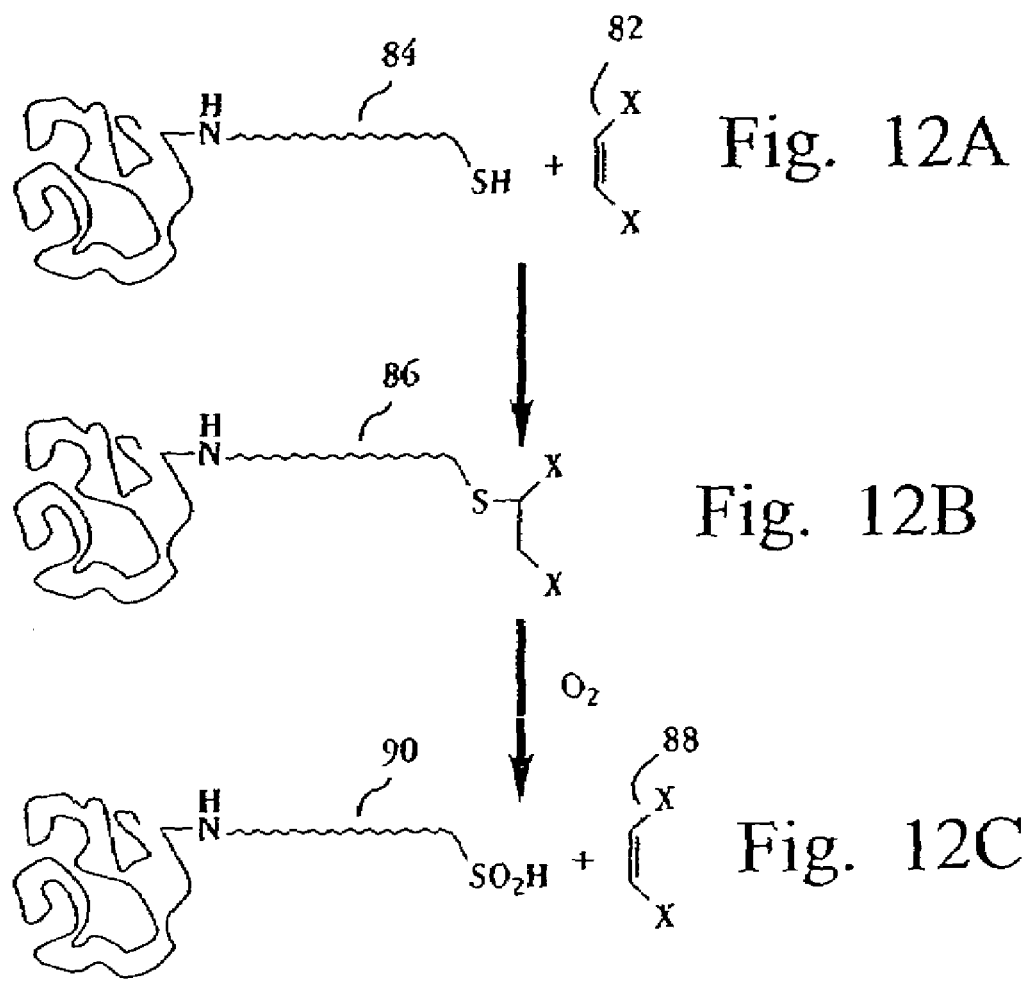
Fig. 12A
Fig. 12B
Fig. 12C
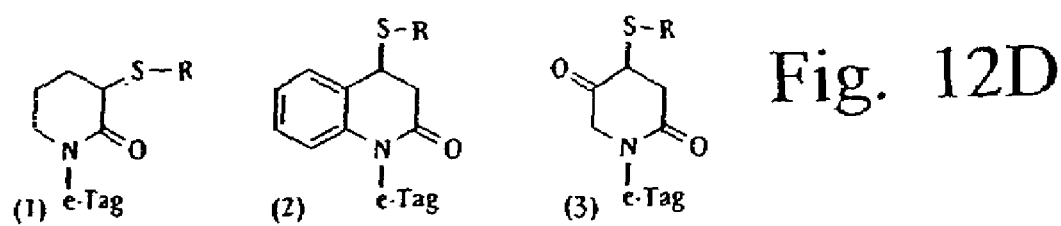
Fig. 12D

MULTIPLEX ANALYSIS USING MEMBRANE-BOUND SENSITIZERS

CROSS-REFERENCE TO RELATED APPLICATIONS AND PATENTS

This is a divisional of U.S. application Ser. No. 10/379,965 filed 04 Mar. 2003 (now U.S. Pat. No. 6,949,347), which claims priority from U.S. provisional applications Ser. No. 60/361,975 filed 5 Mar. 2002 and Ser. No. 60/440,838 filed 17 Jan. 2003, which applications are incorporated herein by reference in their entirety.

FIELD OF THE INVENTION

This invention relates to methods and compositions for detecting and/or measuring one or more analytes embedded in or associated with lipid membranes.

BACKGROUND OF THE INVENTION

Many crucial biological processes take place in or adjacent to cellular membranes including receptor oligomerization, endocytosis, ligand-receptor binding, phosphorylation and de-phosphorylation of membrane proteins, folding and transport of newly synthesized proteins, viral invasion, immune reactions, and so on. Malfunctions in such processes can have profound effects on an organism's health and disease, e.g. Bunn et al, Semin. Oncol., 29 (5 Suppl 14): 38–44 (2002); Baker, Oncogene, 17: 3261–3270 (1998); and the like. For example, in some diseases, such as cancer, relationships have been identified between disease states and aberrancies in membrane molecules, e.g. Yarden, Oncology, 61: Suppl. 2: 1–13 (2001); Ouyang et al, Lancet, 353: 1591–1592 (1999); and the like. Because of such observations, there has been a great deal of interest and research in the cellular and molecular processes at membrane interfaces that relate to disease states, e.g. George et al, Nature Reviews Drug Discovery, 1: 808–820 (2002); Howard et al, Trends in Pharmaceutical Sciences, 22: 132–140 (2001); Seymour, Current Drug Targets, 2: 117–133 (2001). However, studying such processes has been challenging since they are often characterized by a highly complex interaction of many molecular components, e.g. Gutkind, Science STKE: 1–13 (2000); Weng et al, Science, 284: 92–96 (1999). It has been suggested that a full understanding of such complex phenomena requires a systems approach in which "global" measurements are made after systematic perturbations, e.g. Ideker et al, Annu. Rev. Genomics Hum. Genet., 2: 343–372 (2001). This approach has become feasible for some phenomena, such as gene expression in simple organisms where routine measurement of all, or large sets of, expressed genes is possible through the use of microarray technology, e.g. Nature Genetics Supplement, 32: 465–552 (December, 2002). However, for other phenomena, such as signal transduction pathways and other membrane-mediated processes, that involve the interaction of several to many tens of proteins, no comparable technology is available for making global or system-wide measurements.

In view of the above, the availability of a convenient and cost effective technique for measuring the presence or absence or quantities of multiple membrane-associated analytes, such as cell surface receptors, in a single assay reaction would advance the art in many fields where such measurements are becoming increasingly important, including life science research, medical research and diagnostics, drug discovery, animal and plant science, and the like.

SUMMARY OF THE INVENTION

The present invention is directed to methods and compositions for determining the presence, absence, and/or amounts of one or more membrane-associated analytes in a sample. In accordance with the invention, binding compounds derivatized with releasable molecular tags specifically bind to selected membrane-associated analytes, after which the molecular tags are released upon activation of cleavage moieties, or sensitizers, anchored in the same membrane as the membrane-associated analytes. The released molecular tags are then identified by their distinct separation and detection characteristics.

In one aspect, the invention includes a method for determining receptor-specific binding of a molecule, such as a soluble protein, peptide, or other organic molecule, such as a drug candidate molecule. In one embodiment, such receptor-specific molecules are derivatized with releasable molecular tags that are released after binding to a cell surface receptor and activation of cleavage moieties, or sensitizers, anchored in the surface membrane. In another embodiment, underivatized receptor-specific molecules bind to cell surface receptors after which one or more binding compounds are added that specifically bind to the underivatized receptor-specific molecules that form complexes with cell surface receptors. The binding compounds are derivatized with releasable molecular tags that are released upon activation of cleavage moieties, or sensitizers, anchored in the surface membrane.

In another aspect, the present invention includes kits for performing the methods of the invention, such kits comprising lipophilic sensitizers for producing sensitizer-treated membranes and one or more of binding compounds each with one or more molecular tags attached. Such kits may further comprise appropriate buffers and wash solutions for cleaving the cleavable linkages between molecular tags and binding compounds and separation standards that aid in the quantitative determination of the separated molecular tags.

The present invention provides a method of detecting or measuring membrane-associated analytes that has several advantages over current techniques including, but not limited to, (1) the detection and/or measurement of molecular tags that are separated from an assay mixture provide greatly reduced background and a significant gain in sensitivity; and (2) the use of molecular tags that are specially designed for ease of separation and detection thereby providing convenient multiplexing capability.

BRIEF DESCRIPTION OF THE DRAWINGS

FIGS. 1H through 1K illustrate an embodiment of the invention for determining binding or a secreted protein to a cell-surface receptor, in accordance with the invention.

FIGS. 1L through 1O illustrate an embodiment of the invention for a multiplexed determination of binding of each of a plurality of secreted proteins to cell-surface receptors, in accordance with the invention.

FIGS. 11A–11C illustrate one method of forming protein probes for use in the assay of the invention, and the probe cleavage reaction in the presence of singlet oxygen.

FIGS. 12A–12C illustrate a second method of forming protein probes for use in the assay of the invention, and the probe cleavage reaction in the presence of singlet oxygen. FIG. 12D shows three exemplary molecular tag-linker structures for use in the method.

DEFINITIONS

Figure 1A:
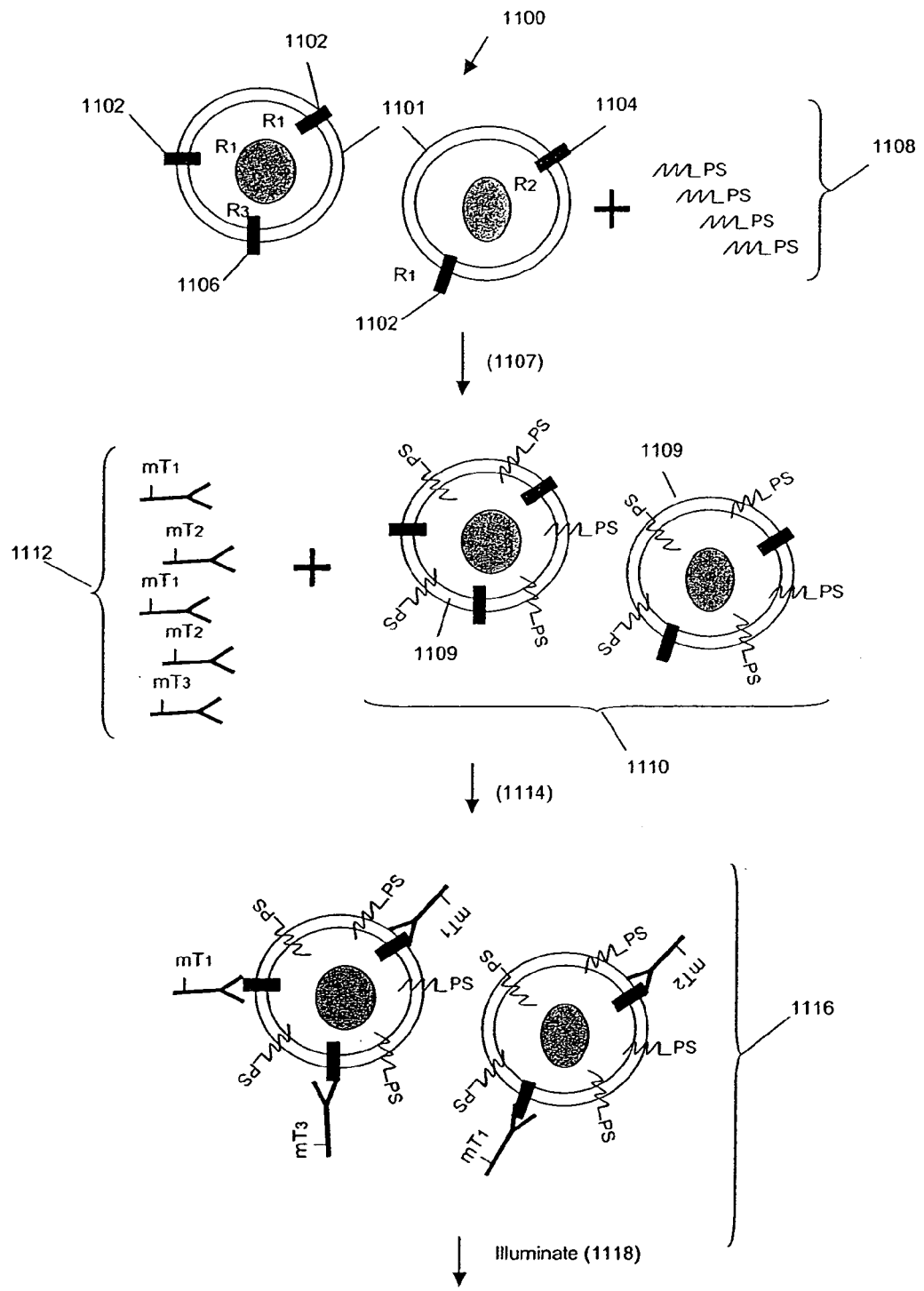
FIGS. 1A and 1B illustrates a method of using intact cells or tissue to detect membrane-associated analytes.

"Antibody" means an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular polypeptide is maintained.

"Antibody binding composition" means a molecule or a complex of molecules that comprise one or more antibodies and derives its binding specificity from an antibody. Antibody binding compositions include, but are not limited to, antibody pairs in which a first antibody binds specifically to a target molecule and a second antibody binds specifically to a constant region of the first antibody; a biotinylated antibody that binds specifically to a target molecule and streptavidin derivatized with moieties such as molecular tags or photosensitizers; antibodies specific for a target molecule and conjugated to a polymer, such as dextran, which, in turn, is derivatized with moieties such as molecular tags or photosensitizers; antibodies specific for a target molecule and conjugated to a bead, or microbead, or other solid phase support, which, in turn, is derivatized with moieties such as molecular tags or photosensitizers, or polymers containing the latter.

"Binding compound" means any molecule to which molecular tags can be directly or indirectly attached that is capable of specifically binding to a membrane-associated analyte. Binding compounds include, but are not limited to, antibodies, antibody binding compositions, peptides, proteins, particularly secreted proteins and orphan secreted proteins, nucleic acids, and organic molecules having a molecular weight of up to 1000 daltons and consisting of atoms selected from the group consisting of hydrogen, carbon, oxygen, nitrogen, sulfur, and phosphorus.

"Capillary-sized" in reference to a separation column means a capillary tube or channel in a plate or microfluidics device, where the diameter or largest dimension of the separation column is between about 25–500 microns, allowing efficient heat dissipation throughout the separation medium, with consequently low thermal convection within the medium.

"Chromatography" or "chromatographic separation" as used herein means or refers to a method of analysis in which the flow of a mobile phase, usually a liquid, containing a mixture of compounds, e.g. molecular tags, promotes the separation of such compounds based on one or more physical or chemical properties by a differential distribution between the mobile phase and a stationary phase, usually a solid. The one or more physical characteristics that form the basis for chromatographic separation of analytes, such as molecular tags, include but are not limited to molecular weight, shape, solubility, pKa, hydrophobicity, charge, polarity, and the like. In one aspect, as used herein, "high pressure (or performance) liquid chromatography" ("HPLC") refers to a liquid phase chromatographic separation that (i) employs a rigid cylindrical separation column having a length of up to 300 mm and an inside diameter of up to 5 mm, (ii) has a solid phase comprising rigid spherical particles (e.g. silica, alumina, or the like) having the same diameter of up to 5 µm packed into the separation column, (iii) takes place at a temperature in the range of from 35° C. to 80° C. and at column pressure up to 150 bars, and (iv) employs a flow rate in the range of from 1 µL/min to 4 mL/min. Preferably, solid phase particles for use in HPLC are further characterized in (i) having a narrow size distribution about the mean particle diameter, with substantially all particle diameters being within 10% of the mean, (ii) having the same pore size in the range of from 70 to 300 angstroms, (iii) having a surface area in the range of from 50 to 250 $m^2$/g, and (iv) having a bonding phase density (i.e. the number of retention ligands per unit area) in the range of from 1 to 5 per $nm^2$. Exemplary reversed phase chromatography media for separating molecular tags include particles, e.g. silica or alumina, having bonded to their surfaces retention ligands, such as phenyl groups, cyano groups, or aliphatic groups selected from the group including $C_8$ through $C_{18}$. Chromatography in reference to the invention includes "capillary electrochromatography" ("CEC"), and related techniques. CEC is a liquid phase chromatographic technique in which fluid is driven by electroosmotic flow through a capillary-sized column, e.g. with inside diameters in the range of from 30 to 100 µm. CEC is disclosed in Svec, Adv. Biochem. Eng. Biotechnol. 76: 1–47 (2002); Vanhoenacker et al, Electrophoresis, 22: 4064–4103 (2001); and like references. CEC column may use the same solid phase materials as used in conventional reverse phase HPLC and additionally may use so-called "monolithic" non-particular packings. In some forms of CEC, pressure as well as electroosmosis drives an analyte-containing solvent through a column.

As used herein, the term "kit" refers to any delivery system for delivering materials. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

The term "ligand" is also used herein to refer to a secreted protein or protein thereof which binds to a given receptor, through a ligand-receptor interaction.

"Membrane-associated analyte" means a substance, compound, molecule, or component or part of any of the foregoing that is directly or indirectly attached to a membrane, especially a biological membrane such as the cell surface membrane of a mammalian cell or tissue. The attachment may be direct, for example, when a membrane-associated analyte has a lipophilic moiety, or is attached to another molecule that has a lipophilic moiety, capable of anchoring it in a membrane. The attachment may also be indirect, for example, when a membrane-associated analyte is a soluble ligand that binds to, and forms a stable complex with, a cell surface receptor. A membrane-associated analyte may be, but is not limited to, a peptide, protein, polynucleotide, polypeptide, oligonucleotide, organic molecule, hapten, epitope, part of a biological cell, a posttranslational modification of a protein, a receptor, a complex sugar attached to a membrane component such as a receptor, a soluble compound forming a stable complex with a membrane such as a vitamin, a hormone, a cytokine, or the like, forming and the like. There may be more than one analyte associated with a single molecular entity, e.g. different phosphorylation sites on the same protein.

The term "orphan secreted protein" means a secreted protein (or ligand) which is uncharacterized as to one or more of (i) the cell type to which the protein binds, (ii) the receptor to which the protein binds, and (iii) the action produced by the binding of the protein to its receptor. Examples include cytokines and lymphokines, including those capable of stimulating production and/or proliferation of spleen cells, lymph node cells or thymocytes, proteins that exhibit immune stimulating or immune suppressing activity, proteins regulating hematopoisesis, tissue growth, cell chemotactic or chemokinetic events, such as cell adhesion molecules, or cell-recruitment ligands, proteins with anti-inflammatory activity and anti-tumor activity.

"Polypeptide" refers to a class of compounds composed of amino acid residues chemically bonded together by amide linkages with elimination of water between the carboxy group of one amino acid and the amino group of another amino acid. A polypeptide is a polymer of amino acid residues, which may contain a large number of such residues. Peptides are similar to polypeptides, except that, generally, they are comprised of a lesser number of amino acids. Peptides are sometimes referred to as oligopeptides. There is no clear-cut distinction between polypeptides and peptides. For convenience, in this disclosure and claims, the term "polypeptide" will be used to refer generally to peptides and polypeptides. The amino acid residues may be natural or synthetic.

"Protein" refers to a polypeptide, usually synthesized by a biological cell, folded into a defined three-dimensional structure. Proteins are generally from about 5,000 to about 5,000,000 or more in molecular weight, more usually from about 5,000 to about 1,000,000 molecular weight, and may include posttranslational modifications, such acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, phosphorylation, prenylation, racemization, selenoylation, sulfation, and ubiquitination, e.g. Wold, F., Post-translational Protein Modifications: Perspectives and Prospects, pgs. 1–12 in Post-translational Covalent Modification of Proteins, B. C. Johnson, Ed., Academic Press, New York, 1983. Proteins include, by way of illustration and not limitation, cytokines or interleukins, enzymes such as, e.g., kinases, proteases, galactosidases and so forth, protamines, histones, albumins, immunoglobulins, scleroproteins, phosphoproteins, mucoproteins, chromoproteins, lipoproteins, nucleoproteins, glycoproteins, T-cell receptors, proteoglycans, unclassified proteins, e.g., somatotropin, prolactin, insulin, pepsin, proteins found in human plasma, blood clotting factors, blood typing factors, protein hormones, cancer antigens, tissue specific antigens, peptide hormones, nutritional markers, tissue specific antigens, and synthetic peptides.

The term "sample" in the present specification and claims is used in a broad sense. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

A "separation profile" in reference to the separation of molecular tags means a chart, graph, curve, bar graph, or other representation of signal intensity data versus a parameter related to the molecular tags, such as retention time, mass, or the like, that provides a readout, or measure, of the number of molecular tags of each type produced in an assay. A separation profile may be an electropherogram, a chromatogram, an electrochromatogram, a mass spectrogram, or like graphical representation of data depending on the separation technique employed. A "peak" or a "band" or a "zone" in reference to a separation profile means a region where a separated compound is concentrated. There may be multiple separation profiles for a single assay if, for example, different molecular tags have different fluorescent labels having distinct emission spectra and data is collected and recorded at multiple wavelengths. In one aspect, released molecular tags are separated by differences in electrophoretic mobility to form an electropherogram wherein different molecular tags correspond to distinct peaks on the electropherogram. A measure of the distinctness, or lack of overlap, of adjacent peaks in an electropherogram is "electrophoretic resolution," which may be taken as the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of molecular tags whose members have electrophoretic mobilities that differ by at least a peak-resolving amount, such quantity depending on several factors well known to those of ordinary skill, including signal detection system, nature of the fluorescent moieties, the diffusion coefficients of the tags, the presence or absence of sieving matrices, nature of the electrophoretic apparatus, e.g. presence or absence of channels, length of separation channels, and the like.

"Specific" or "specificity" in reference to the binding of one molecule to another molecule, such as a binding compound, or probe, for a target analyte, means the recognition, contact, and formation of a stable complex between the probe and target, together with substantially less recognition, contact, or complex foundation of the probe with other molecules. In one aspect, "specific" in reference to the binding of a first molecule to a second molecule means that to the extent the first molecule recognizes and forms a complex with another molecules in a reaction or sample, it forms the largest number of the complexes with the second molecule. In one aspect, this largest number is at least fifty percent of all such complexes form by the first molecule. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, ionic and hydrophobic interactions, and the like, dominate the interaction of the molecules. As used herein, "stable complex" in reference to two or more molecules means that such molecules form noncovalently linked aggregates, e.g. by specific binding, that under assay conditions are thermodynamically more favorable than a non-aggregated state.

As used herein, the term "spectrally resolvable" in reference to a plurality of fluorescent labels means that the fluorescent emission bands of the labels are sufficiently distinct, i.e. sufficiently non-overlapping, that molecular tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558; 4,811,218, or the like, or in Wheeless et al, pgs. 21–76, in Flow Cytometry: Instrumentation and Data Analysis (Academic Press, New York, 1985).

The term "secreted protein," or "soluble protein," refers to proteins that are (i) expressed intracellularly, (ii) secreted from the cell into the extracellular medium, e.g., typically requiring a leader sequence that directs the expressed protein from the endoplasmic reticulum through the cell membrane, and (iii) act on a receptor, typically a cell-surface receptor, to effect or initiate some cellular event or activity, which may be an intracellular event, including cell proliferation or stimulation, a cell-surface event, or cell-cell interaction event.

DETAILED DESCRIPTION OF THE INVENTION

In one aspect, the present invention is directed to methods and compositions for determining the presence and/or amount of one or more membrane-associated analytes in a sample by releasing molecular tags from binding compounds as the result of specific binding reactions between the membrane-associated analytes and binding compounds. Activating a membrane-bound sensitizer, particularly a membrane-bound photosensitizer, generates released molecular tags.

Figure 1B:
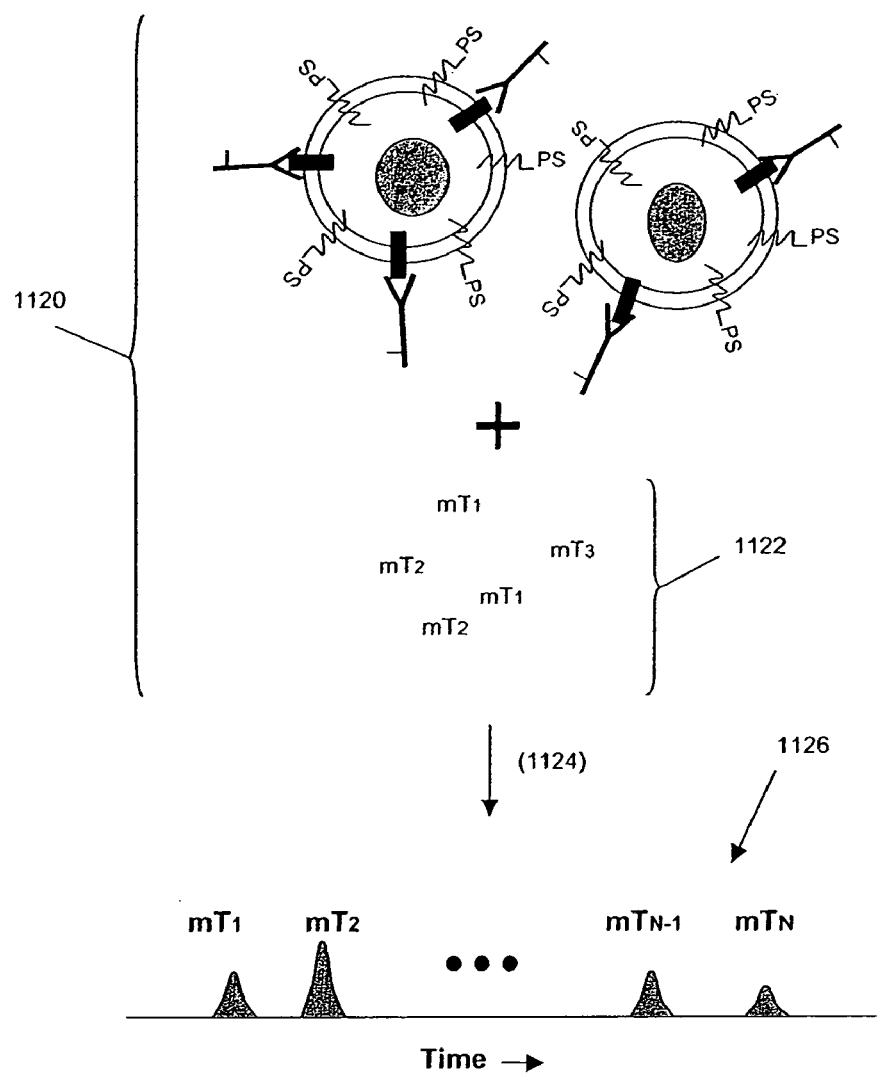

One embodiment of the invention is illustrated in FIGS. 1A and 1B. Cells (1100) having cell surface membrane (1101) and receptors (1102, "R1"), (1104, "R2"), and (1106, "R3")—the membrane-associated analytes—are incubated with lipophilic photosensitizers (1108) to form (1107) photosensitizer-treated membranes (1109), which are part of intact cells (1110). Binding compounds (1112) having molecular tags ("mT$_k$") attached are combined with photosensitizer-treated membranes (1109) under conditions that permit specific binding of binding compounds (1112) to their respective target membrane-associated analytes. Reaction mixture (1116) is then illuminated (1118) with a light of wavelength and intensity to excite the membrane-bound photosensitizers to generated singlet oxygen which, in turn, cleaves the molecular tags (1122) from the binding compounds, shown in FIG. 1B. Molecular tags (1122) are then separated (1124) from reaction mixture (1120) and identified in separation profile (1126).

Figure 1C:
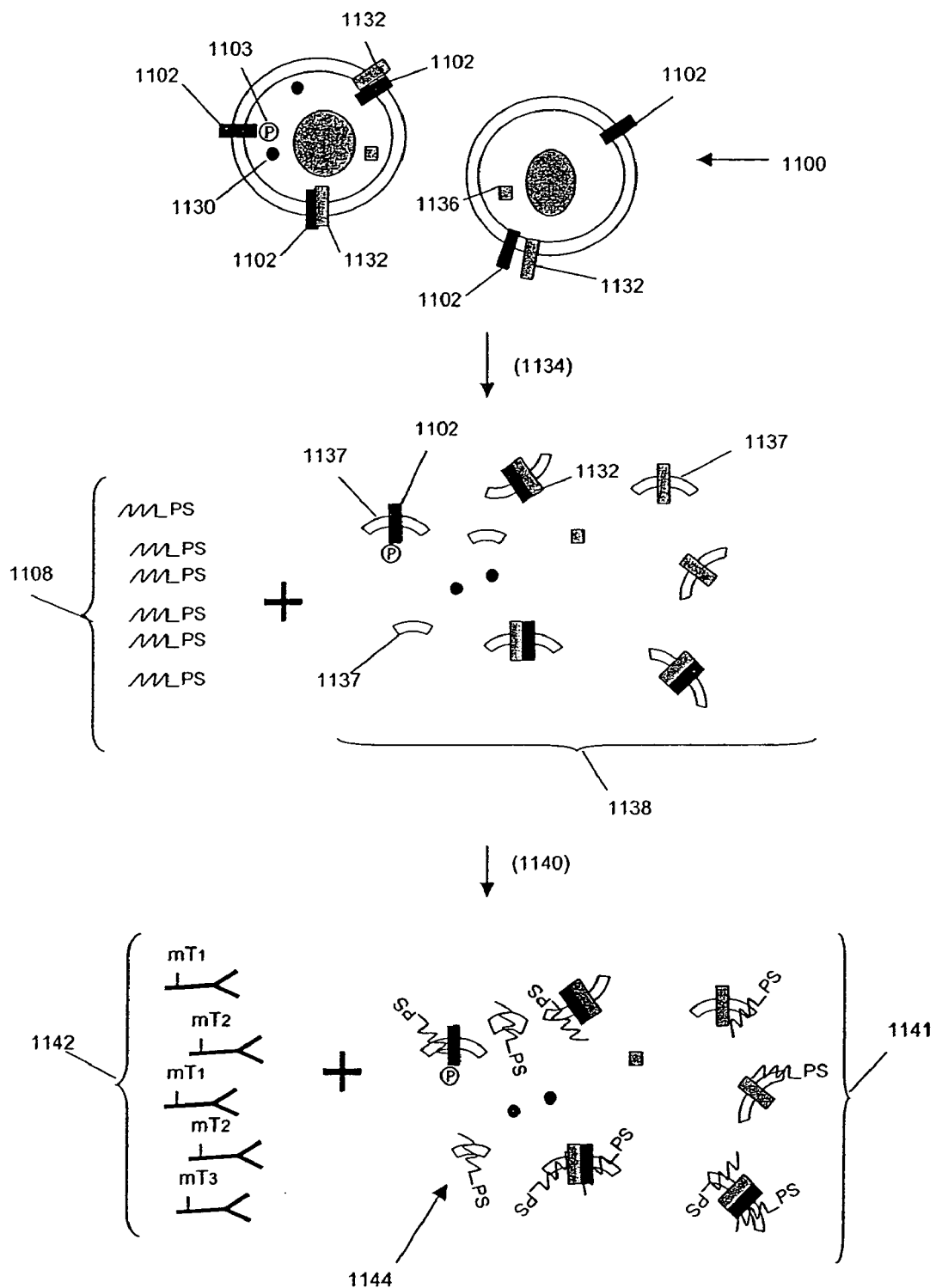
FIGS. 1C and 1D illustrate a method of using cell lysates to detect both intracellular and extracellular sites of membrane-associated analytes.
Figure 1D:
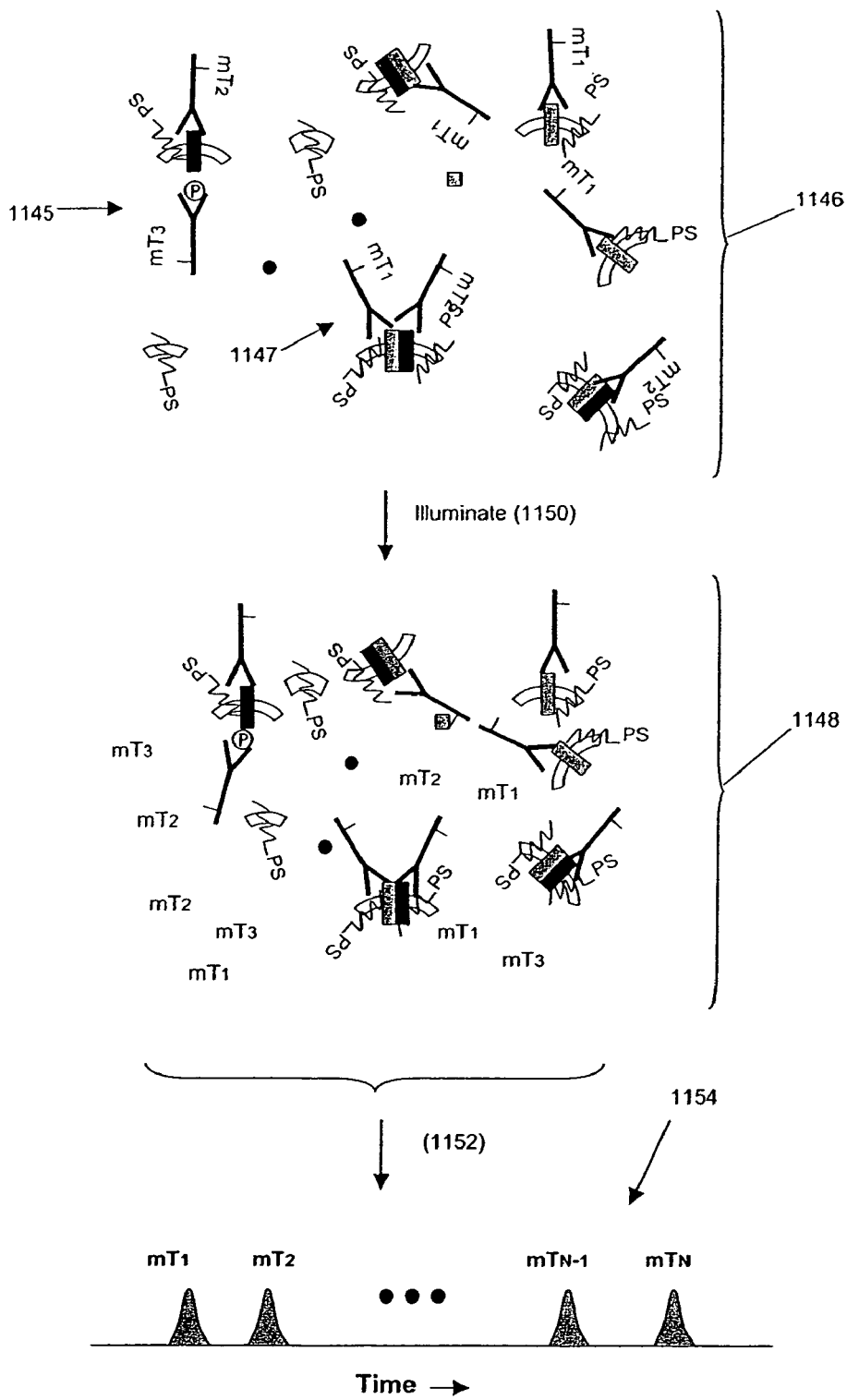

In another embodiment shown in FIGS. 1C and 1D, cells (1100) contain various extracellular and intracellular molecules, including receptor (1102) having phosphorylated intracellular portion (1103), receptor (1132) and intracellular proteins (1130) and (1136). After lysing cells (1100), lysate (1138) is formed containing various cell fragments including receptors (1102) and (1132) embedded in portions of membrane (1137). Lysate (1138) is combined with lipophilic photosensitizers (1108) to form photosensitizer-treated membranes, as exemplified by membrane fragment (1144). Photosensitizer-treated membranes (1141) are combined with binding compounds (1142) to form reaction mixture (1146), which may include complexes between binding compounds and intracellular membrane-associated analytes (1145) as well as extracellular cellular membrane-associated analytes (1147). After reaction mixture (1146) is illuminated (1150), photosensitzers generate singlet oxygen, which cleaves the cleavable linkages of the molecular tags, and the molecular tags (mT$_1$, mT$_2$, . . . mT$_N$) are released into reaction mixture (1148). Molecular tags are then separated (1152) from the other components of reaction mixture (1148) and identified in a separation profile (1154), such as an electropherogram.

Figure 1E:
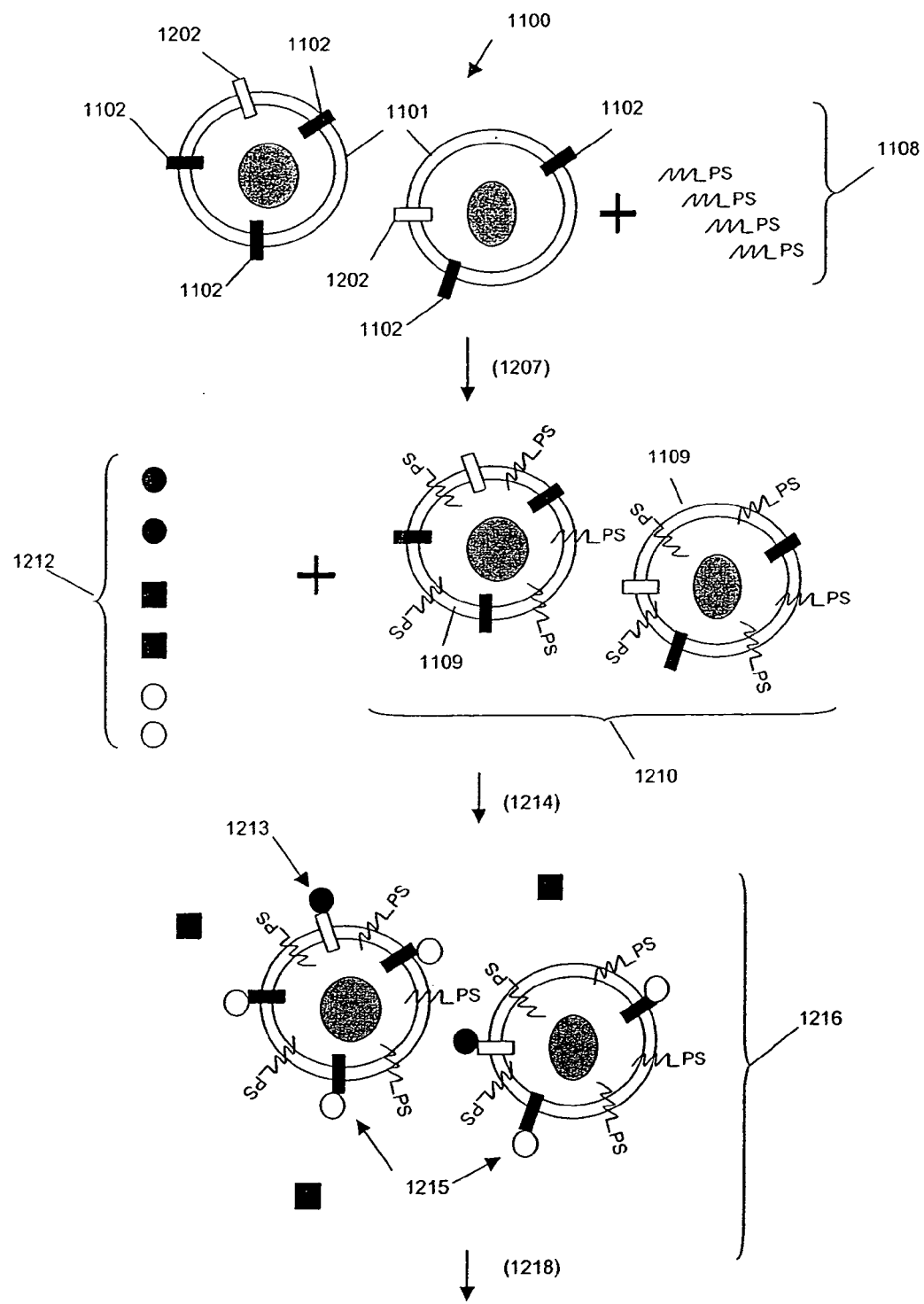
FIGS. 1E through 1G illustrate a method of using intact cells or tissue to determine the binding of receptor-specific molecules to receptors in a cell or tissue sample.
Figure 1F:
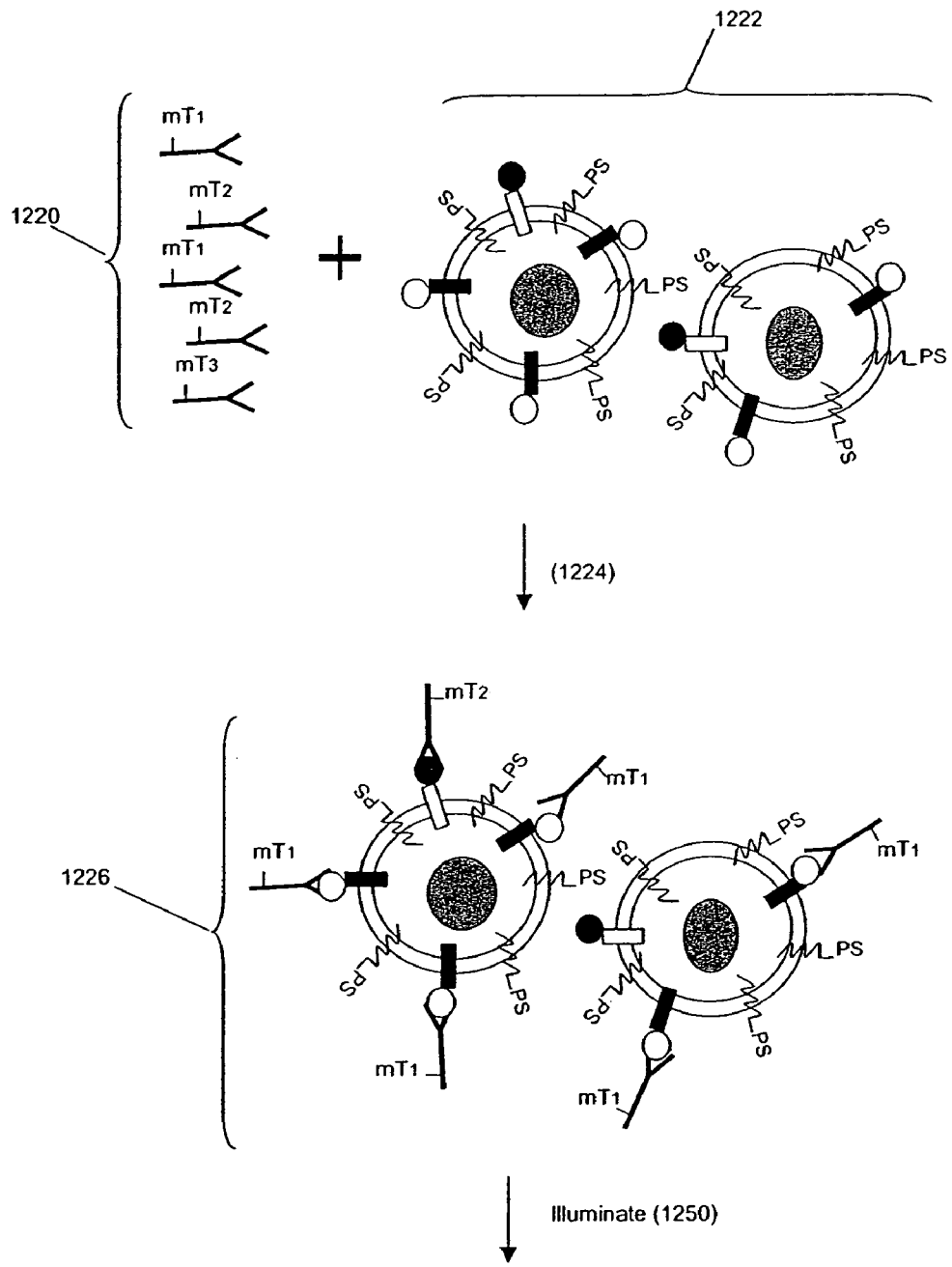
Figure 1G:
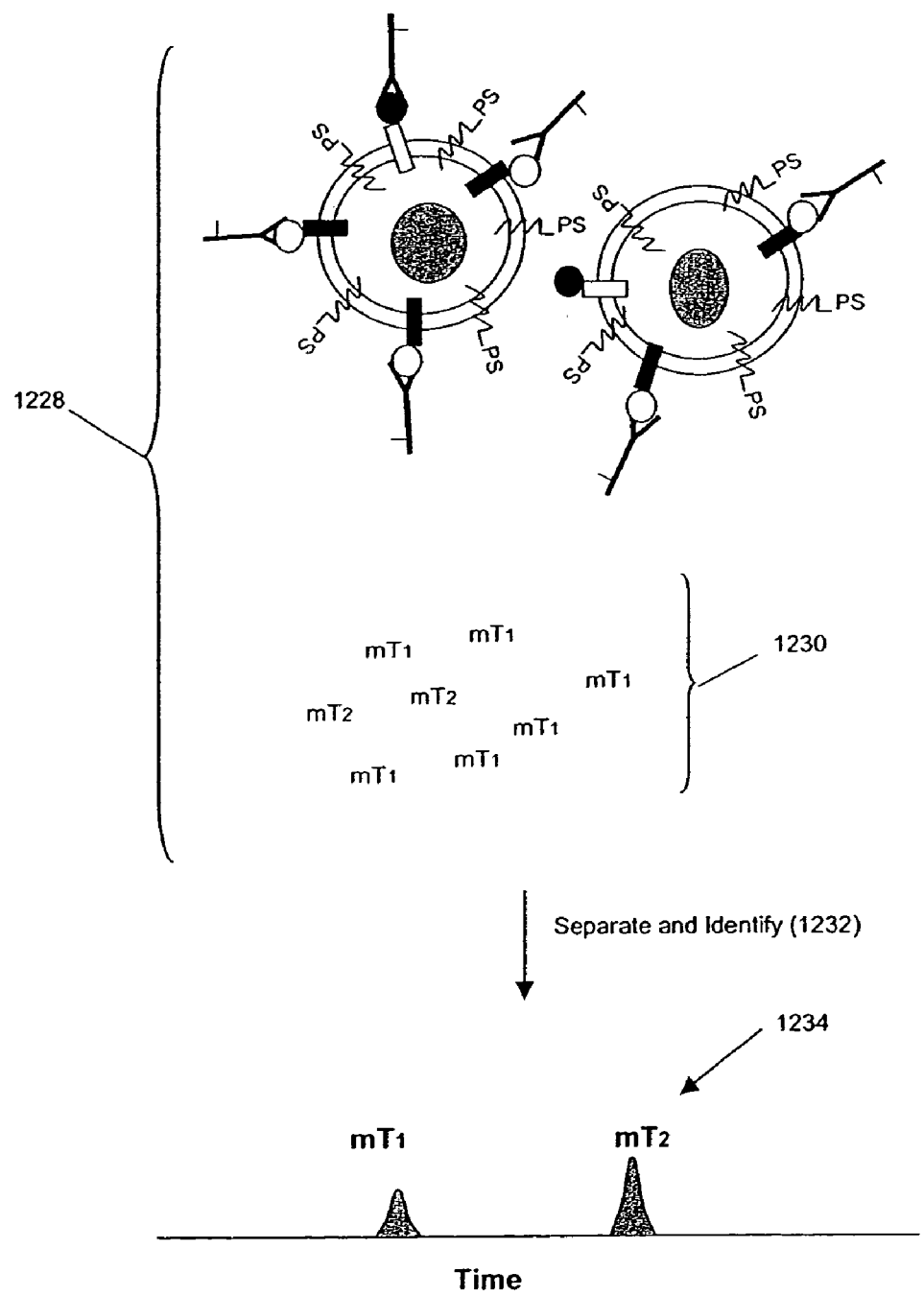

In another embodiment illustrated in FIGS. 1E–1G, a method is provide for determining the binding of candidate molecules, such as peptides, to cell surface receptors. A population of cells (1100) having surface membranes (1101) and surface receptors (1102) and (1202) are treated with lipophilic photosensitizers (1108) to form a population of cells (1210) having sensitizer-treated membranes (1109). This population is combined and incubated (1214) with candidate molecules (1212) so that such molecules specifically bind to receptors to form (1216) complexes, such as (1213) and (1215). After removing (1218), e.g. by washing, unbound candidate molecules, population (1222) containing the candidate molecule-receptor complexes are combined with binding compounds, such as antibodies (1220), specific for the candidate molecules that are derivatized with molecular tags (illustrated as "mT$_1$," "mT$_2$", and "mT$_3$" in the figure). As a result, a population of cells (1226) is formed (1224) that contains complexes comprising (i) a binding compound (ii) a candidate molecule, and (iii) a receptor. After removal of free, or unbound, binding compound, the population is illuminated (1250) to activate the photosensitizers in the cell surface membrane so that singlet oxygen is generated releasing (1228) the molecular tags (1230). The released molecular tags are then separated and identified (1232) in electropherogram (1234).

FIGS. 1H and 1I show a portion of an outer membrane region 20 of the target cell, showing a pair of transmembrane receptors 22, each having an external binding moiety 24. The cells have been modified, as will be described below, to contain surface-attached sensitizer groups 26 that are capable of generating a short-lived active chemical species, such as singlet oxygen, under selected activation conditions, e.g., photo-illumination.

In practicing the method of this embodiment, the cell or cells, are mixed with a protein probe 28 composed of the secreted protein of interest, indicated at 30 and "P$_1$," and a molecular tag 32 (indicated as "eT$_1$" in the figure) which is attached to the protein through a cleavable linker. The probe may have a single molecular tag, or multiple molecular tags, each coupled to the protein through a cleavable linker.

FIG. 1I illustrates the binding of the protein probe to its receptor. The relatively small size of the molecular tag attached to the protein has the advantage of producing little or oily a modest effect on the binding characteristics between the protein and its receptor, as will be shown. At the same time, the relatively small change in size of a mobility modifiers required for electrophoretic separation of the corresponding tags, allows for a large number of separable tags, e.g., up to 50 tags, that all have about the same perturbation effect on protein binding to the target receptor, in a multiplexed assay.

As can be appreciated from FIG. 1I, probe binding to a cell-surface receptor places the probe's linker in proximity with the cell surface, that is, the linker is attached through the protein to the cell surface. Once this binding has occurred, the reaction mixture containing the cell(s) and probe(s) is reacted under conditions effective to selectively cleave only those probe linkers in proximity to the cell surface. This is done, in the embodiment shown, by illuminating the reaction mixture, generating singlet oxygen at the surface region of the cells. The singlet oxygen is sufficiently short-lived that it can cleave surface-bound probes, but not reach unbound, solution-phase probe. The reaction thus selectively cleaves bound probe linkers, releasing molecular tags, such as molecular tag 34 (FIG. 1J).

Although not shown here, the assay typically involves a control reaction containing cells, e.g., non-mammalian cells, that do not include a target receptor for the protein, but which are modified, as above, to include a sensitizer for generating a short-term cleaving species. The probe employed in the control may be the same one used in the test mixture; preferably, however, the control probe includes a different mobility modifier or a different detectable label, allowing both test and control probes to be detected in a single separation medium, i.e., with multiplexed separation and detection. In addition, a known amount of a "standard" molecular tag may be added to the test assay to provide a standard for calibrating the mobility and peak characteristics of the released molecular tag(s).

Molecular tags from the test and control mixtures thus include molecular tag 34 released from probe binding to a target cell receptor, any molecular tag released in the control assay, due to non-specific binding of the control probe to the control cell, and the molecular tag standard. The mixtures containing these molecular tags are combined and the molecular tags are separated, in this embodiment, by electrophoretic separation. The separated peaks are detected, for example by a fluorescence emission detection of fluorescent labels (R) in the molecular tags. FIG. 1K shows an exemplary electropherogram of the combined tags. The molecular tag standard peak at 36 provides a peak for calibrating mobility. From this the migration positions of the control molecular tag and test molecular tag can be determined or confirmed. Similarly, the measured peak height or area under the curve (AUC) of the standard molecular tag, relative to the known amount of standard molecular tag added, can be used to calculate the amount of test and control molecular tags from the measured peak heights or AUC in the electropherogram. Alternatively, where the released tag(s) can be detected in the absence of electrophoretic separation, e.g., where there is only one tag, or the test and control tags have different fluorescence emission properties, it may be sufficient merely to separate the tag(s) from uncleaved probes for detection purposes.

From the peaks identified as the test and control peaks in FIG. 1K, it can be determined that the test probe binds specifically to a receptor on the surface of the target cells, and that non-specific binding accounts for relatively little of the total amount of released molecular tag. The method can be extended, as described, to confirm the presence of specific binding, and to determine the binding affinity of the probe for the receptor.

FIGS. 1L to 1O illustrate the same assay carried out in a multiplexed format, for assaying the binding of a plurality of orphan secreted proteins $P_1-P_n$ to receptors contained on the surface of one or more target cells or groups of cells. FIG. 1L shows a portion of a cell having three different cell-surface receptors, 42, 44, 46, each having an external binding portion 48, 50, 52, respectively. It is recognized that the cell may in actuality have hundreds or thousands of different surface receptors, and the number of any receptor type on a cell may range from a few hundred or less to several thousand per cell.

To the cell(s) is added a set of probes of the form $P_i-(L-E_i)_k$, where Pi represents one of a plurality of different orphan secreted proteins to be assayed, L is a cleavable linkage, $E_i$ is a molecular tag, and k is an integer greater than or equal to one, as described below. In the illustration, three such probes, 54, 56, 58, each composed of a different secreted protein 60, 64, 68, respectively, and attached through a cleavable linkage L attached to a unique molecular tag 62, 66, 70, respectively.

FIG. 1M illustrates the binding of the three probes 54, 58, 58 to their respective receptors 42, 44, 46 on the target cell. Once this binding has occurred, the reaction mixture containing the cell(s) and probe(s) is reacted under conditions, e.g., by photo-illumination, effective to selectively release molecular tags from cell-bound probes, such as molecular tags 62, 66, 70 indicated in FIG. 1N.

Separation and detection of the molecular tags, as above, yields an electropherogram (FIG. 1O) whose peaks correspond to those of all molecular tags released in the test mixture (along with an molecular tag standard, if include), and a control molecular tag from a separate control assay, as above. From the results, one can readily determine the identity of those molecular tags which bound to target cell(s)—in this case, probes 54, 56, and 58—and the relative amounts of probe bound, which in turn, reflects the relative numbers of each of the different receptors carried on the cells.

Samples containing target membrane-associated analytes may come from a wide variety of sources including cell cultures, animal or plant tissues, microorganisms, or the like. Samples are prepared for assays of the invention using conventional techniques, which may depend on the source from which a sample is taken. Guidance for sample preparation techniques can be found in standard treatises, such as Sambrook et al, Molecular Cloning, Second Edition (Cold Spring Harbor Laboratory Press, New York, 1989); Innis et al, editors, PCR Protocols (Academic Press, New York, 1990); Berger and Kimmel, "Guide to Molecular Cloning Techniques," Vol. 152, Methods in Enzymology (Academic Press, New York, 1987); Ohlendieck, K. (1996). Protein Purification Protocols; Methods in Molecular Biology, Humana Press Inc., Totowa, N.J. Vol 59: 293–304; Method Booklet 5, "Signal Transduction" (Biosource International, Camarillo, Calif., 2002); or the like. For mammalian tissue culture cells, or like sources, samples of target membrane-associated analytes may be prepared by conventional cell lysis techniques (e.g. 0.14 M NaCl, 1.5 mM $MgCl_2$, 10 mM Tris-Cl (pH 8.6), 0.5% Nonidet P-40, and protease and/or phosphatase inhibitors as required).

As described more fully below, target membrane-associated analytes are determined by separation and identification of the released molecular tags. A wide variety of separation techniques may be employed that can distinguish molecules based on one or more physical, chemical, or optical differences among molecules being separated including but not limited to electrophoretic mobility, molecular weight, shape, solubility, pKa, hydrophobicity, charge, charge/mass ratio, polarity, or the like. In one aspect, molecular tags in a plurality differ in electrophoretic mobility and optical detection characteristics and are separated by electrophoresis. In another aspect, molecular tags in a plurality differ in molecular weight, shape, solubility, pKa, hydrophobicity, charge, polarity, and are separated by normal phase or reverse phase HPLC, ion exchange HPLC, capillary electrochromatography, mass spectroscopy, gas phase chromatography, or like technique.

Another aspect of the present invention is providing sets of molecular tags that may be separated into distinct bands or peaks by the separation technique employed after they are released from binding compounds. Molecular tags within a set may be chemically diverse; however, for convenience, sets of molecular tags are usually chemically related. For example, they may all be peptides, or they may consist of different combinations of the same basic building blocks or monomers, or they may be synthesized using the same basic scaffold with different substituent groups for imparting different separation characteristics, as described more fully below. The number of molecular tags in a plurality may vary depending on several factors including the mode of separation employed, the labels used on the molecular tags for detection, the sensitivity of the binding moieties, the efficiency with which the cleavable linkages are cleaved, and the like. In one aspect, the number of molecular tags in a plurality ranges from 2 to several tens, e.g. 50. In other aspects, the size of the plurality may be in the range of from 2 to 40, 2 to 20, 2 to 10, 3 to 50, 3 to 20, 3 to 10, 4 to 50, 4 to 10, 5 to 20, or 5 to 10.

Membranes

The membranes containing analytes to be determined by the invention can be obtained from biological cells. Such membranes include cell surface membranes, nuclear membranes, mitochondrial membranes, or other intracellular membranes. Alternatively, analytes may be associated with artificially created membranes, as exemplified by micelles and liposomes. The cell(s) used in the methods described herein can be of any origin, including from prokaryotes, eukaryotes, or archeons, but preferably contain membranes that are lipophilic. The cell(s) may be living or dead. If obtained from a multicellular organism, the cell may be of any cell type. Thus, the cell(s) may be a cultured cell line or a primary isolate, the cell(s) may be mammalian, amphibian, reptilian, plant, yeast, bacterium, spirochetes, or protozoan. The cell(s) may be, for example, human, murine, rat, hamster, chicken, quail, goat or dog. The cell may be a normal cell, a mutated cell, a genetically manipulated cell, a tumor cell, hybridomas that are positive for secretion of selected antibodies, and the like. Of particular interest are membranes obtained from the type of cell that differentially expresses (over-expresses or under-expresses) a disease-causing gene. As is apparent to one skilled in the art, various cell lines, such as CHO, for example, may be obtained from public or private repositories. The largest depository agent is American Type Culture Collection (http://www.atcc.org), which offers a diverse collection of well-characterized cell lines derived from a vast number of organisms and tissue samples.

Exemplary cell types from multicellular organisms include acidophils, acinar cells, pinealocytes, adipocytes, ameloblasts, astrocytes, basal (stem) cells, basophils, hepatocytes, neurons, bulging surface cells, C cells, cardiac muscle cells, centroacinar cells, chief cells, chondrocytes, Clara cells, columnar epithelial cells, corpus luteal cells, decidual cells, dendrites, endrocrine cells, endothelial cells, enteroendocrine cells, eosinophils, erythrocytes, extraglomerular mesangial cells, fetal fibroblasts, fetal red blood cells, fibroblasts, follicular cells, ganglion cells, giant Betz cells, goblet cells, hair cells, inner hair cells, type I hair cells, hepatocytes, endothelial cells, Leydig cells, lipocytes, liver parenchymal cells, lymphocytes, lysozyme-secreting cells, macrophages, mast cells, megakaryocytes, melanocytes, mesangial cells, monocytes, myoepithelial cells, myoid cells, neck mucous cells, nerve cells, neutrophils, oligodendrocytes, oocytes, osteoblasts, osteochondroclasts, osteoclasts, osteocytes, pillar cells, sulcal cells, parathyroid cells, parietal cells, pepsinogen-secreting cells, pericytes, pinealocytes, pituicytes, plasma cells, platelets, podocytes, spermatocytes, Purkinje cells, pyramidal cells, red blood cells, reticulocytes, Schwann cells, Sertoli cells, columnar cells, skeletal muscle cells, smooth muscle cells, somatostatin cells, enteroendocrine cells, spermatids, spermatogonias, spermatozoas, stellate cells, supporting Deiter cells, support Hansen cells, surface cells, surface epithelial cells, surface mucous cells, sweat gland cells, T lymphocytes, theca lutein cells, thymocytes, thymus epithelial cell, thyroid cells, transitional epithelial cells, type I pneumonocytes, and type II pneumonocytes.

Cell membranes can also be obtained from cell type that is associated with a particular disease or with a specific disease stage. The association with a particular disease or disease stage may be established by the cell's aberrant behavior in one or more biological processes such as cell cycle regulation, cell differentiation, apoptosis, chemotaxis, cell motility and cytoskeletal rearrangement. A disease cell may also be confirmed by the presence of a pathogen causing the disease of concern (e.g. HIV for AIDS and HBV for hepatitis B). The types of diseases involving abnormal functioning of specific types of cells may include but are not limited to autoimmune diseases, cancer, obesity, hypertension, diabetes, neuronal and/or muscular degenerative diseases, cardiac diseases, endocrine disorders, and any combinations thereof. Exemplary types of tumor cells include adenomas, carcinomas, adenocarcinomas, fibroadenomas, ameloblastomas, astrocytomas, mesotheliomas, cholangiocarcinomas, cholangiofibromas, cholangiomas, chondromas, chondrosarcomas, chordomas, choriocarcinomas, craniopharyngiomas, cystadenocarcinomas, cystadenomas, dysgerminomas, ependymomas, epitheliomas, erythroid leukemias, fibroadenomas, fibromas, fibrosarcomas, gangliogliomas, ganglioneuromas, ganglioneuroblastomas, gliomas, granulocytic leukemias, hemangiomas, hemangiopericytomas, hemangiosarcomas, hibernomas, histiocytomas, keratoacanthomas, leiomyomas, leiomyosarcomas, lipomas, liposarcomas, luteomas, lympliangiomas, lymphangiosarcomas, lymphomas, medulloblastomas, melanomas, meningiomas, mesotheliomas, myelolipomas, nephroblastomas, neuroblastomas, neuromyoblastomas, odontomas, oligodendrogliomas, osteochondromas, osteomas, osteosarcomas, papillomas, paragangliomas, pheochromocytomas, pinealomas, pituicytomas, retinoblastomas, rhabdomyosarcomas, sarcomas, schwannomas, seminomas, teratomas, thecomas and thymomas.

Molecular Tags and Cleavable Linkages

In one embodiment, molecular tags are cleaved from a binding compound by reaction of a cleavable linkage with an active species, such as singlet oxygen, generated by a cleavage-inducing moiety, e.g. Singh et al, International patent publication WO 01/83502 and WO 02/95356.

An aspect of the invention includes providing mixtures of pluralities of different binding compounds, wherein each different binding compound has one or more molecular tags attached through cleavable linkages. The nature of the binding compound, cleavable linkage and molecular tag may vary widely. A binding compound may comprise an antibody binding composition, an antibody, a peptide, a peptide or non-peptide ligand for a cell surface receptor, a protein, an oligonucleotide, an oligonucleotide analog, such as a peptide nucleic acid, a lectin, or any other molecular entity that is capable of specific binding or complex formation with a membrane-associated analyte of interest. In one aspect, a binding compound, which can be represented by the formula below, comprises one or more molecular tags attached to an analyte-specific binding moiety.

$$B\text{-}(L\text{-}E)_k$$

wherein B is a binding moiety; L is a cleavable linkage; and E is a molecular tag. Preferably, in homogeneous assays for non-polynucleotide analytes, cleavable linkage, L, is an oxidation-labile linkage, and more preferably, it is a linkage that may be cleaved by singlet oxygen. The moiety "-$(L\text{-}E)_k$" indicates that a single binding compound may have multiple molecular tags attached via cleavable linkages. In one aspect, k is an integer greater than or equal to one, but in other embodiments, k may be greater than several hundred, e.g. 100 to 500, or k is greater than several hundred to as many as several thousand, e.g. 500 to 5000. Within a composition of the invention, usually each of the plurality of different types of binding compound has a different molecular tag, E. Cleavable linkages, e.g. oxidation-labile linkages, and molecular tags, E, are attached to B by way of conventional chemistries.

Preferably, B is an antibody binding composition. Such compositions are readily formed from a wide variety of commercially available antibodies, both monoclonal and polyclonal, specific for membrane-associated analytes. Exemplary monoclonal antibodies specific for membrane-associated analytes include, but are not limited to, phosphate-specific monoclonal antibodies, e.g. described in the following references: Epstein et al, U.S. Pat. No. 5,599,681, Blaydes et al, Methods in Molecular Biology, 99: 177–189 (2000); Nagata et al, Genes Cells, 6: 653–664 (2001).

When L is oxidation labile, L is preferably a thioether or its selenium analog; or an olefin, which contains carbon-carbon double bonds, wherein cleavage of a double bond to an oxo group, releases the molecular tag, E. Illustrative thioether bonds are disclosed in Willner et al, U.S. Pat. No. 5,622,929 which is incorporated by reference. Illustrative olefins include vinyl sulfides, vinyl ethers, enamines, imines substituted at the carbon atoms with an α-methane (CH, a carbon atom having at least one hydrogen atom), where the vinyl group may be in a ring, the heteroatom may be in a ring, or substituted on the cyclic olefinic carbon atom, and there will be at least one and up to four heteroatoms bonded to the olefinic carbon atoms. The resulting dioxetane may decompose spontaneously, by heating above ambient temperature, usually below about 75° C., by reaction with acid or base, or by photo-activation in the absence or presence of a photosensitizer. Such reactions are described in the following exemplary references: Adam and Liu, J. Amer. Chem. Soc. 94, 1206–1209, 1972, Ando, et al., J.C.S. Chem. Comm. 1972, 477–8, Ando, et al., Tetrahedron 29, 1507–13, 1973, Ando, et al., J. Amer. Chem. Soc. 96, 6766–8, 1974, Ando and Migita, ibid. 97, 5028–9, 1975, Wasserman and Terao, Tetra. Lett. 21, 1735–38, 1975, Ando and Watanabe, ibid. 47, 4127–30, 1975, Zaklika, et al., Photochemistry and Photobiology 30, 35–44, 1979, and Adam, et al., Tetra. Lett. 36, 7853–4, 1995. See also, U.S. Pat. No. 5,756,726.

The formation of dioxetanes is obtained by the reaction of singlet oxygen with an activated olefin substituted with an molecular tag at one carbon atom and the binding moiety at the other carbon atom of the olefin. See, for example, U.S. Pat. No. 5,807,675. These cleavable linkages may be depicted by the following formula:

$$-W-(X)_n C_\alpha = C_\beta (Y)(Z)-$$

wherein:

W may be a bond, a heteroatom, e.g., O, S, N, P, M (intending a metal that forms a stable covalent bond), or a functionality, such as carbonyl, imino, etc., and may be bonded to X or $C_\alpha$;

at least one X will be aliphatic, aromatic, alicyclic or heterocyclic and bonded to $C_\alpha$ through a hetero atom, e.g., N, O, or S and the other X may be the same or different and may in addition be hydrogen, aliphatic, aromatic, alicyclic or heterocyclic, usually being aromatic or aromatic heterocyclic wherein one X may be taken together with Y to form a ring, usually a heterocyclic ring, with the carbon atoms to which they are attached, generally when other than hydrogen being from about 1 to 20, usually 1 to 12, more usually 1 to 8 carbon atoms and one X will have 0 to 6, usually 0 to 4 heteroatoms, while the other X will have at least one heteroatom and up to 6 heteroatoms, usually 1 to 4 heteroatoms;

Y will come within the definition of X, usually being bonded to $C_\beta$ through a heteroatom and as indicated may be taken together with X to form a heterocyclic ring;

Z will usually be aromatic, including heterocyclic aromatic, of from about 4 to 12, usually 4 to 10 carbon atoms and 0 to 4 heteroatoms, as described above, being bonded directly to $C_\beta$ or through a heteroatom, as described above;

n is 1 or 2, depending upon whether the molecular tag is bonded to $C_\alpha$ or X;

wherein one of Y and Z will have a functionality for binding to the binding moiety, or be bound to the binding moiety, e.g. by serving as, or including a linkage group, to a binding moiety, T.

Preferably, W, X, Y, and Z are selected so that upon cleavage molecular tag, E, is within the size limits described below.

Illustrative cleavable linkages include S(molecular tag)-3-thiolacrylic acid, N(molecular tag), N-methyl 4-amino-4-butenoic acid, 3-hydroxyacrolein, N-(4-carboxyphenyl)-2-(molecular tag)-imidazole, oxazole, and thiazole.

Also of interest are N-alkyl acridinyl derivatives, substituted at the 9 position with a divalent group of the formula:

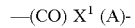

$$-(CO) X^1 (A)-$$

wherein:

$X^1$ is a heteroatom selected from the group consisting of O, S, N, and Se, usually one of the first three; and A is a chain of at least 2 carbon atoms and usually not more than 6 carbon atoms substituted with an molecular tag, where preferably the other valences of A are satisfied by hydrogen, although the chain may be substituted with other groups, such as alkyl, aryl, heterocyclic groups, etc., A generally being not more than 10 carbon atoms.

Also of interest are heterocyclic compounds, such as diheterocyclopentadienes, as exemplified by substituted imidazoles, thiazoles, oxazoles, etc., where the rings will usually be substituted with at least one aromatic group and in some instances hydrolysis will be necessary to release the molecular tag.

Also of interest are tellurium (Te) derivatives, where the Te is bonded to an ethylene group having a hydrogen atom β to the Te atom, wherein the ethylene group is part of an alicyclic or heterocyclic ring, that may have an oxo group, preferably fused to an aromatic ring and the other valence of the Te is bonded to the molecular tag. The rings may be coumarin, benzoxazine, tetralin, etc.

Figure 4:
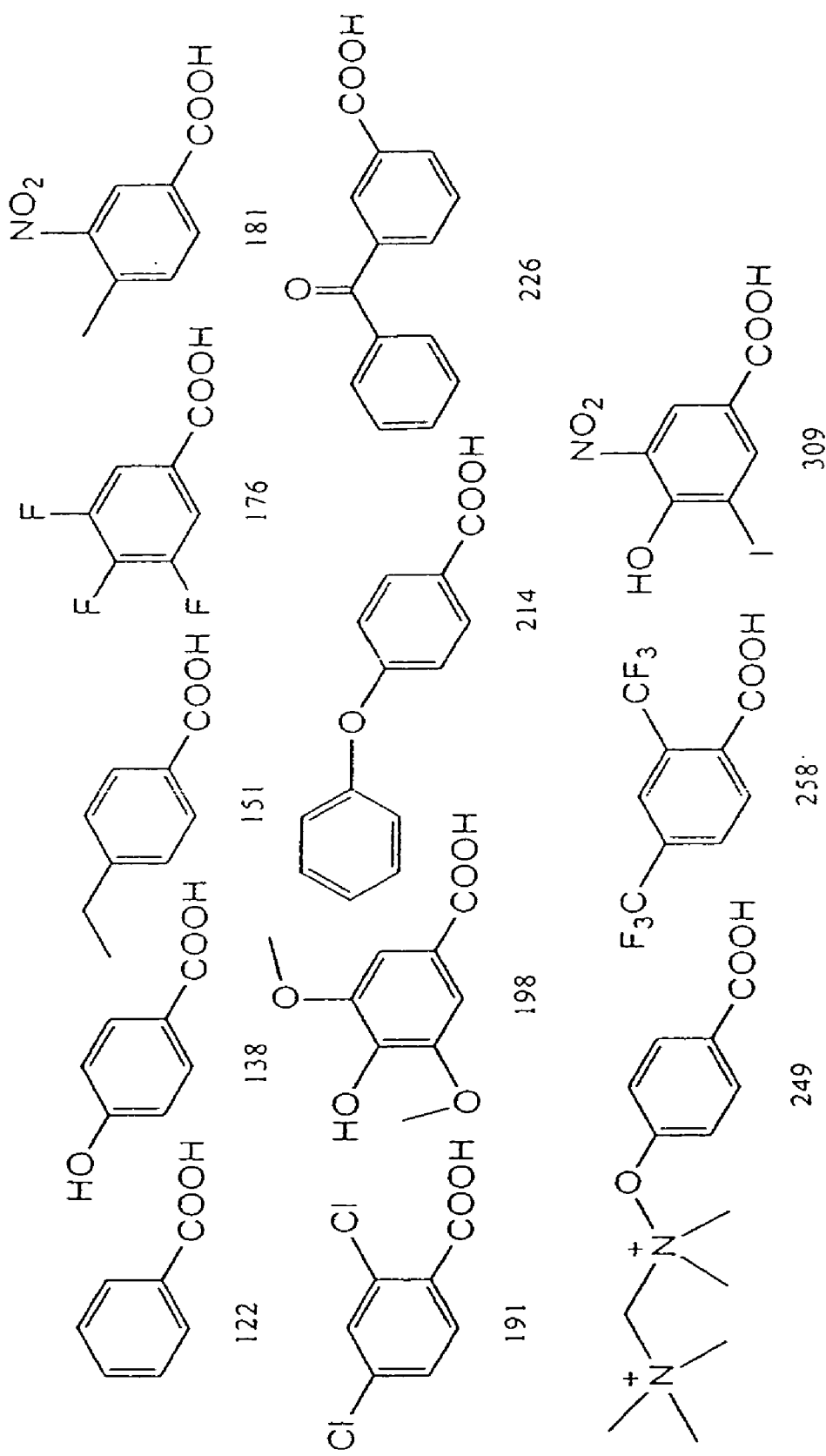
FIG. 4 shows the structure of several benzoic acid derivatives that can serve as mobility modifiers.
Figure 6:
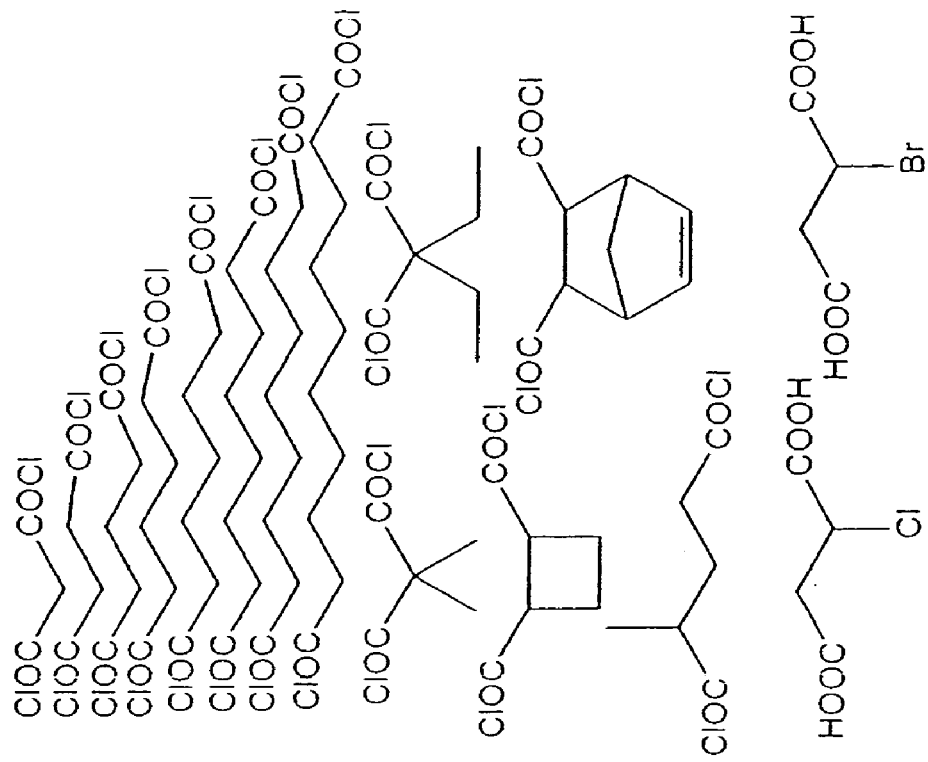
FIG. 6 illustrates several amino alcohols and diacid dichlorides that can be assembled into mobility modifiers in the synthesis of molecular tags.
Figure 6:
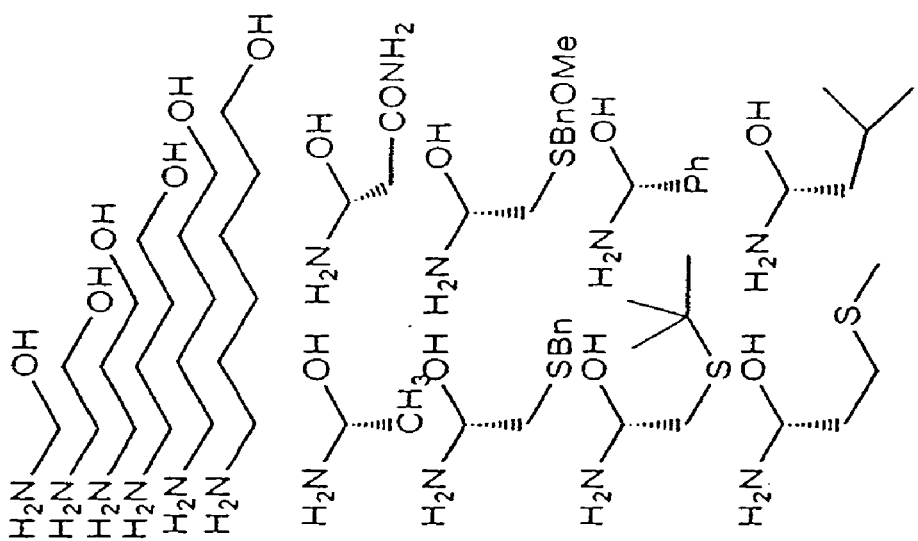
Figure 7A:
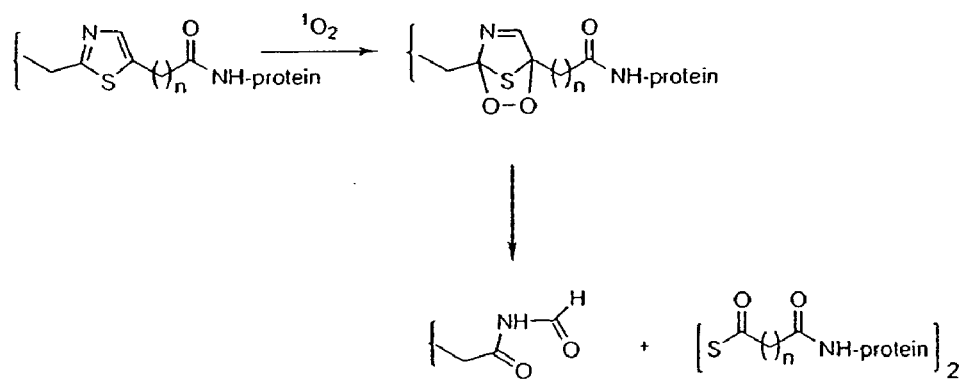
FIGS. 7A–F illustrate oxidation-labile linkages and their respective cleavage reactions mediated by singlet oxygen.
Figure 7B:
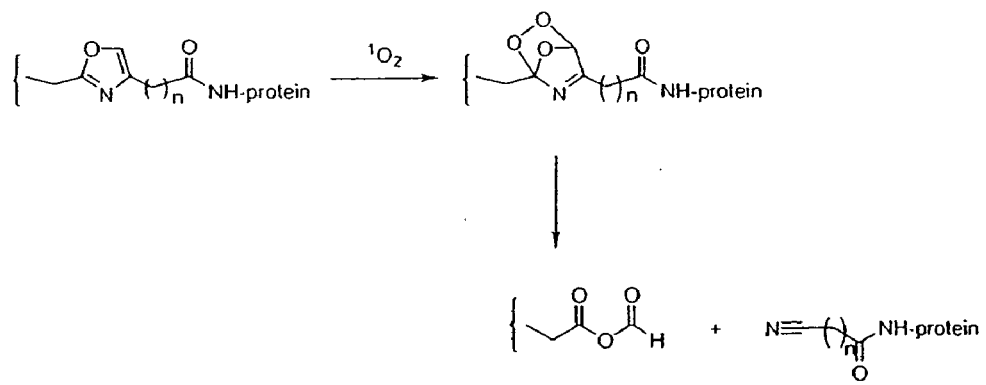
Figure 7C:
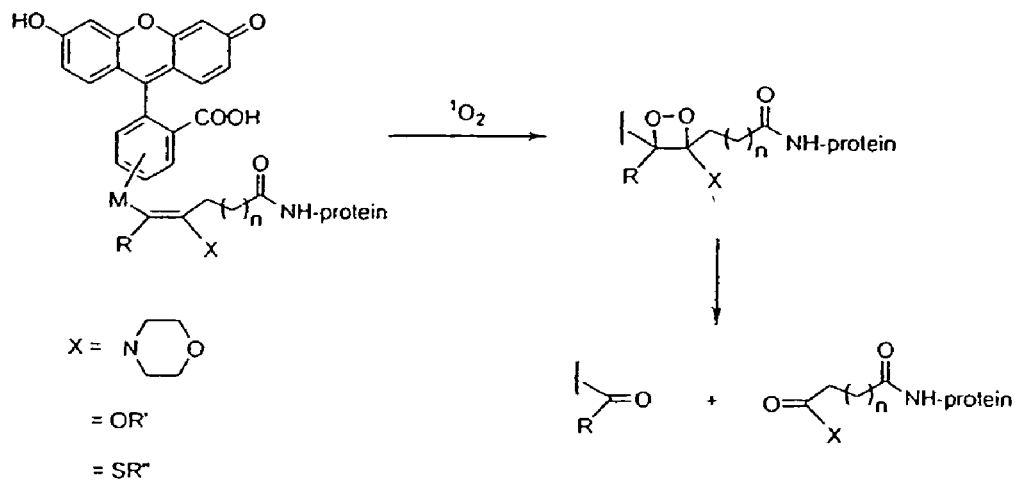
Figure 7D:
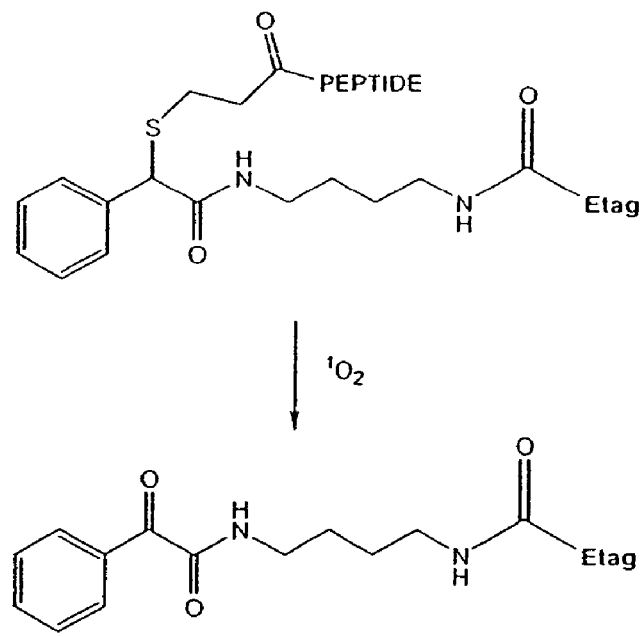
Figure 7E:
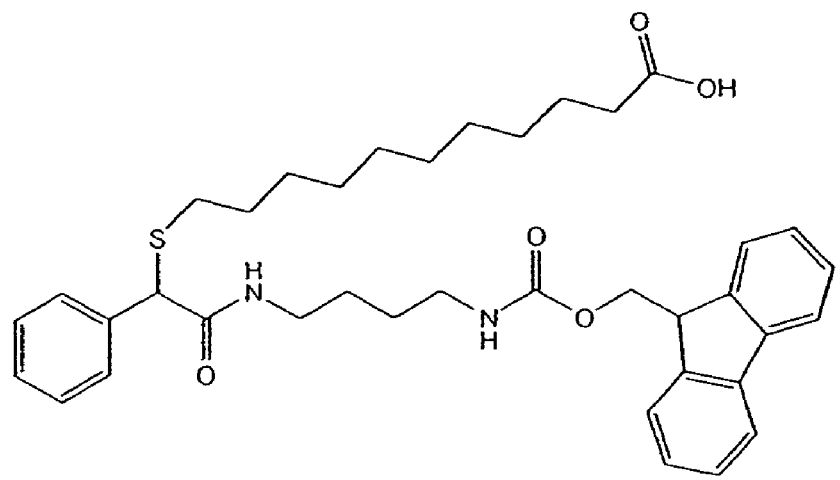
Figure 7F:
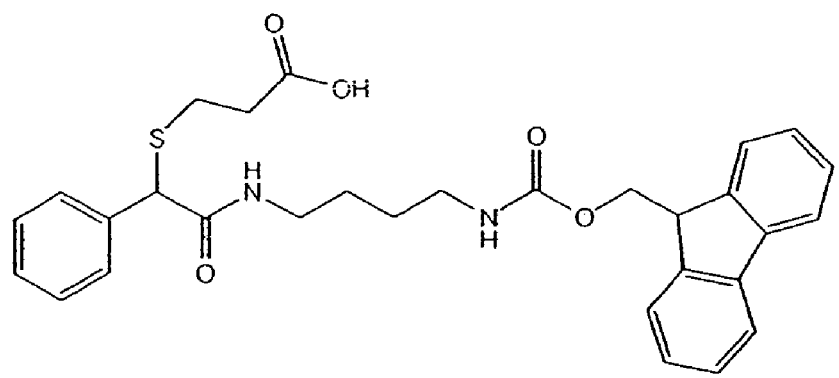
Figure 8A:
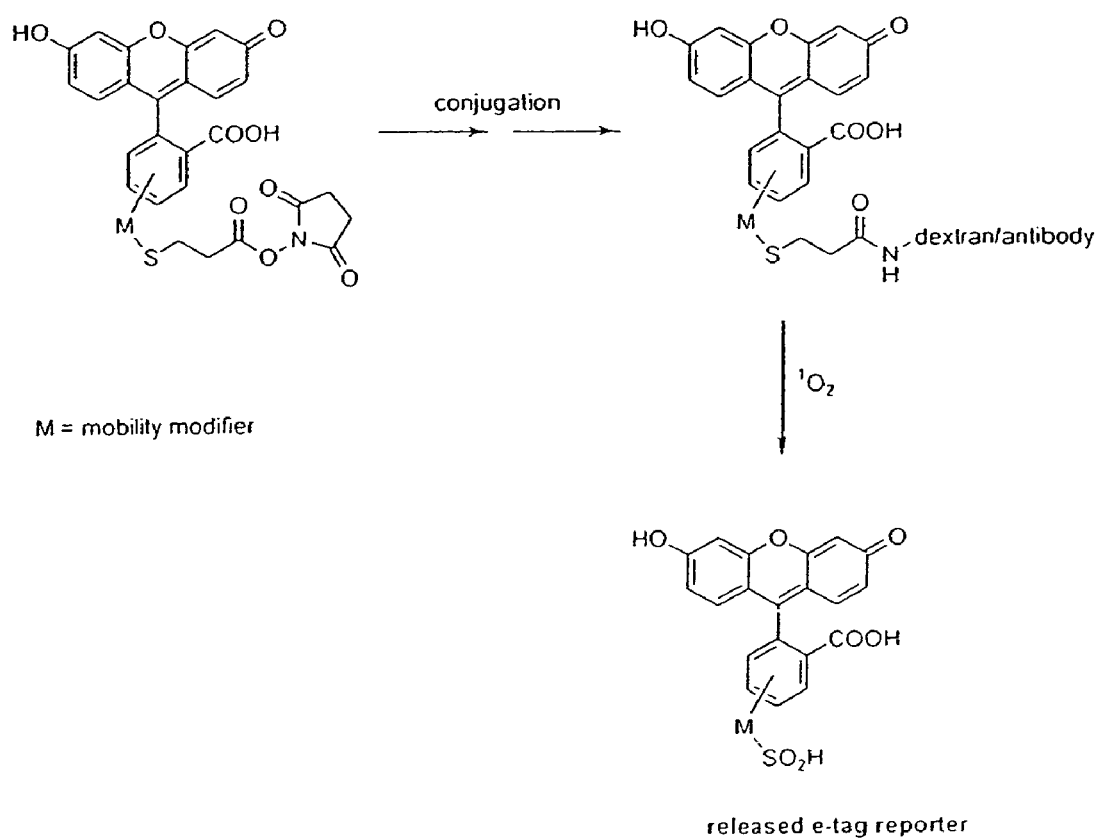
FIGS. 8A–B illustrate the general methodology for conjugation of an e-tag moiety to an antibody to form an e-tag probe, and the reaction of the resulting probe with singlet oxygen to produce a sulfinic acid moiety as the released molecular tag.
Figure 8B:
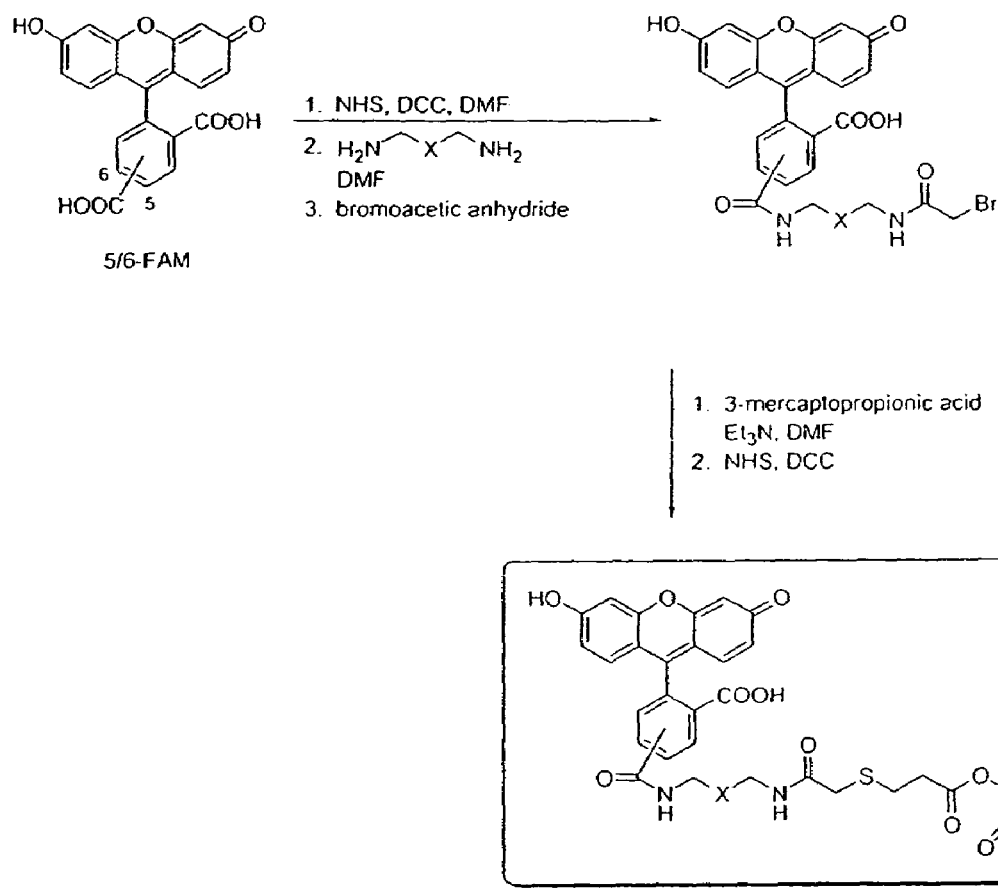

Several preferred cleavable linkages and their cleavage products are illustrated in FIGS. 7A–F. The thiazole cleavable linkage, "—$CH_2$-thiazole-$(CH2)_n$—C(=O)—NH-protein," shown in FIG. 7A, results in an molecular tag with the moiety "—$CH_2$—C(=O)—NH—CHO." Preferably, n is in the range of from 1 to 12, and more preferably, from 1 to 6. The oxazole cleavable linkage, "—$CH_2$-oxazole-$(CH2)_n$—C(=O)—NH-protein," shown in FIG. 7B, results in an molecular tag with the moiety "—$CH_2$—C(=O)O—CHO." An olefin cleavable linkage (FIG. 7C) is shown in connection with the binding compound embodiment "B-L-M-D," described above and with D being a fluorescein dye. The olefin cleavable linkage may be employed in other embodiments also. Cleavage of the illustrated olefin linkage results in an molecular tag of the form: "R—(C=O)-M-D," where "R" may be any substituent within the general description of the molecular tags, E, provided above. Preferably, R is an electron-donating group, e.g. Ullman et al, U.S. Pat. No. 6,251,581; Smith and March, March's Advanced Organic Chemistry: Reactions, Mechanisms, and Structure, $5^{th}$ Edition (Wiley-Interscience, New York, 2001); and the like. More preferably, R is an electron-donating group having from 1–8 carbon atoms and from 0 to 4 heteroatoms selected from the group consisting of O, S, and N. In further preference, R is —N(Q)$_2$, —OQ, p-[C$_6$H$_4$N(Q)$_2$], furanyl, n-alkylpyrrolyl, 2-indolyl, or the like, where Q is alkyl or aryl. In further reference to the olefin cleavable linkage of FIG. 7C, substituents "X" and "R" are equivalent to substituents "X" and "Y" of the above formula describing cleavable linkage, L. In particular, X in FIG. 7C is preferably morpholino, —OR', or —SR", where R' and R" are aliphatic, aromatic, alicyclic or heterocyclic having from 1 to 8 carbon atoms and 0 to 4 heteroatoms selected from the group consisting of O, S. and N. A preferred thioether cleavable linkage is illustrated in FIG. 6D having the form "—(CH$_2$)$_2$—S—CH(C$_6$H$_5$)C(=O)NH—(CH$_2$)$_n$—NH—," wherein n is in the range of from 2 to 12, and more preferably, in the range of from 2 to 6. Thioether cleavable linkages of the type shown in FIG. 7D may be attached to binding moieties, T, and molecular tags, E, by way of precursor compounds shown in FIGS. 7E and 7F. To attach to an amino group of a binding moiety, T, the terminal hydroxyl is converted to an NHS ester by conventional chemistry. After reaction with the amino group and attachment, the Fmoc protection group is removed to produce a free amine which is then reacted with an NHS ester of the molecular tag, such as compounds produced by the schemes of FIGS. 1, 2, and 4, with the exception that the last reaction step is the addition of an NHS ester, instead of a phosphoramidite group.

Molecular tag, E, in the present invention may comprise an electrophoric tag as described in the following references when separation of pluralities of molecular tags are carried out by gas chromatography or mass spectrometry: Zhang et al, Bioconjugate Chem., 13: 1002–1012 (2002); Giese, Anal. Chem., 2: 165–168 (1983); and U.S. Pat. Nos. 4,650,750; 5,360,819; 5,516,931; 5,602,273; and the like.

Molecular tag, E, is preferably a water-soluble organic compound that is stable with respect to the active species, especially singlet oxygen, and that includes a detection or reporter group. Otherwise, E may vary widely in size and structure. In one aspect, E has a molecular weight in the range of from about 50 to about 2500 daltons, more preferably, from about 50 to about 1500 daltons. Preferred structures of E are described more fully below. E may comprise a detection group for generating an electrochemical, fluorescent, or chromogenic signal. In embodiments employing detection by mass, E may not have a separate moiety for detection purposes. Preferably, the detection group generates a fluorescent signal.

Molecular tags within a plurality are selected so that each has a unique separation characteristic and/or a unique optical property with respect to the other members of the same plurality. In one aspect, the chromatographic or electrophoretic separation characteristic is retention time under set of standard separation conditions conventional in the art, e.g. voltage, column pressure, column type, mobile phase, electrophoretic separation medium, or the like. In another aspect, the optical property is a fluorescence property, such as emission spectrum, fluorescence lifetime, fluorescence intensity at a given wavelength or band of wavelengths, or the like. Preferably, the fluorescence property is fluorescence intensity. For example, each molecular tag of a plurality may have the same fluorescent emission properties, but each will differ from one another by virtue of a unique retention time. On the other hand, or two or more of the molecular tags of a plurality may have identical retention times, but they will have unique fluorescent properties, e.g. spectrally resolvable emission spectra, so that all the members of the plurality are distinguishable by the combination of molecular separation and fluorescence measurement.

Preferably, released molecular tags are detected by electrophoretic separation and the fluorescence of a detection group. In such embodiments, molecular tags having substantially identical fluorescence properties have different electrophoretic mobilities so that distinct peaks in an electropherogram are formed under separation conditions. Preferably, pluralities of molecular tags of the invention are separated by conventional capillary electrophoresis apparatus, either in the presence or absence of a conventional sieving matrix. Exemplary capillary electrophoresis apparatus include Applied Biosystems (Foster City, Calif.) models 310, 3100 and 3700; Beckman (Fullerton, Calif.) model P/ACE MDQ; Amersham Biosciences (Sunnyvale, Calif.) MegaBACE 1000 or 4000; SpectruMedix genetic analysis system; and the like. Electrophoretic mobility is proportional to $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more. Preferably, in such conventional apparatus, the electrophoretic mobilities of molecular tags of a plurality differ by at least one percent, and more preferably, by at least a percentage in the range of from 1 to 10 percent.

In one aspect, molecular tag, E, is (M, D), where M is a mobility-modifying moiety, and D is a detection moiety. The notation "(M, D)" is used to indicate that the ordering of the M and D moieties may be such that either moiety can be adjacent to the cleavable linkage, L. That is, "B-L-(M, D)" designates binding compound of either of two forms: "B-L-M-D" or "B-L-D-M."

Detection moiety, D, may be a fluorescent label or dye, a chromogenic label or dye, an electrochemical label, or the like. Preferably, D is a fluorescent dye. Exemplary fluorescent dyes for use with the invention include water-soluble rhodamine dyes, fluoresceins, 4,7-dichlorofluoresceins, benzoxanthene dyes, and energy transfer dyes, disclosed in the following references: Handbook of Molecular Probes and Research Reagents, 8th ed., (Molecular Probes, Eugene, 2002); Lee et al, U.S. Pat. No. 6,191,278; Lee et al, U.S. Pat. No. 6,372,907; Menchen et al, U.S. Pat. No. 6,096,723; Lee et al, U.S. Pat. No. 5,945,526; Lee et al, Nucleic Acids Research, 25: 2816–2822 (1997); Hobb, Jr., U.S. Pat. No. 4,997,928; Khanna et al., U.S. Pat. No. 4,318,846; Reynolds, U.S. Pat. No. 3,932,415; Eckert et al, U.S. Pat. No. 2,153,059; Eckert et al, U.S. Pat. No. 2,242,572; Taing et al, International patent publication WO 02/30944; and the like. Further specific exemplary fluorescent dyes include 5- and 6-carboxyrhodamine 6G; 5- and 6-carboxy-X-rhodamine, 5- and 6-carboxytetramethylrhodamine, 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7',8'-dibenzo-4',5'-dichloro-5- and 6-carboxy-4,7-dichlorofluorescein, 2',7'-dichloro-5- and 6-carboxy-4,7-dichlorofluorescein, and 2',4',5',7'-tetrachloro-5- and 6-carboxy-4,7-dichlorofluorescein. Most preferably, D is a fluorescein or a fluorescein derivative.

The size and composition of mobility-modifying moiety, M, can vary from a bond to about 100 atoms in a chain, usually not more than about 60 atoms, more usually not more than about 30 atoms, where the atoms are carbon, oxygen, nitrogen, phosphorous, boron and sulfur. Generally, when other than a bond, the mobility-modifying moiety has from about 0 to about 40, more usually from about 0 to about 30 heteroatoms, which in addition to the heteroatoms indicated above may include halogen or other heteroatom. The total number of atoms other than hydrogen is generally fewer than about 200 atoms, usually fewer than about 100 atoms. Where acid groups are present, depending upon the pH of the medium in which the mobility-modifying moiety is present, various cations may be associated with the acid group. The acids may be organic or inorganic, including carboxyl, thionocarboxyl, thiocarboxyl, hydroxamic, phosphate, phosphite, phosphonate, phosphinate, sulfonate, sulfinate, boronic, nitric, nitrous, etc. For positive charges, substituents include amino (includes ammonium), phosphonium, sulfonium, oxonium, etc., where substituents are generally aliphatic of from about 1–6 carbon atoms, the total number of carbon atoms per heteroatom, usually be less than about 12, usually less than about 9. The side chains include amines, ammonium salts, hydroxyl groups, including phenolic groups, carboxyl groups, esters, amides, phosphates, heterocycles. M may be a homo-oligomer or a hetero-oligomer, having different monomers of the same or different chemical characteristics, e.g., nucleotides and amino acids.

In another aspect, (M,D) moieties are constructed from chemical scaffolds used in the generation of combinatorial libraries. For example, the following references describe scaffold compound useful in generating diverse mobility modifying moieties: peptoids (PCT Publication No WO 91/19735, Dec. 26, 1991), encoded peptides (PCT Publication WO 93/20242, Oct. 14 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. U.S.A. 90: 6909–6913 (1993), vinylogous polypeptides (Hagihara et al. J. Amer. Chem. Soc. 114: 6568 (1992)), nonpeptidal peptidomimetics with a Beta-D-Glucose scaffolding (Hirschmann, R. et al., J. Amer. Chem. Soc. 114: 9217–9218 (1992)), analogous organic syntheses of small compound libraries (Chen, C. et al. J.Amer. Chem. Soc. 116: 2661(1994)), oligocarbamates (Cho, C. Y. et al. Science 261: 1303(1993)), peptidyl phosphonates (Campbell, D. A. et al., J. Org. Chem. 59:658 (1994)); Cheng et al, U.S. Pat. No. 6,245,937; Heizmam et al, "Xanthines as a scaffold for molecular diversity," Mol. Divers. 2: 171–174 (1997); Pavia et al, Bioorg. Med. Chem., 4: 659–666 (1996); Ostresh et al, U.S. Pat. No. 5,856,107; Gordon, E. M. et al., J. Med. Chem. 37: 1385 (1994); and the like. Preferably, in this aspect, D is a substituent on a scaffold and M is the rest of the scaffold.

In yet another aspect, (M, D) moieties are constructed from one or more of the same or different common or commercially available linking, cross-linking, and labeling reagents that permit facile assembly, especially using a commercial DNA or peptide synthesizer for all or part of the synthesis. In this aspect, (M, D) moieties are made up of subunits usually connected by phosphodiester and amide bonds. Exemplary, precursors include, but are not limited to, dimethoxytrityl (DMT)-protected hexaethylene glycol phosphoramidite, 6-(4-Monomethoxytritylamino)hexyl-(2-cyanoethyl)-(N,N-diisopropyl)-phosphoramidite, 12-(4-Monomethoxytritylamino)dodecyl-(2-cyanoethyl)-(N,N-diisopropyl)-phosphoramidite, 2-[2-(4-Monomethoxytrityl)aminoethoxy]ethyl-(2-cyanoethyl), N,N-diisopropyl)-phosphoramidite, (S-Trityl-6-mercaptohexyl)-(2-cyanoethyl)-(N,N-diisopropyl)-phosphoramidite, 5'-Fluorescein phosphoramidite, 5'-Hexachloro-Fluorescein Phosphoramidite, 5'-Tetrachloro-Fluorescein Phosphoramidite, 9-O-Dimethoxytrityl-triethylene glycol, 1-[(2-cyanoethyl)-(N,N-diisopropyl)]-phosphoramidite, 3(4,4'Dimethoxytrityloxy)propyl-1-[(2-cyanoethyl)-(N,N-diisopropyl)]-phosphoramidite, 5'-O-Dimethoxytrityl-1',2'-Dideoxyribose-3'-[(2-cyanoethyl)-(N,N-diisopropyl)]-phosphoramidite, 18-O Dimethoxytritylhexaethyleneglycol, 1-[(2-cyanoethyl)-(N,N-diisopropyl)]-phosphoramidite, 12-(4,4'-Dimethoxytrityloxy)dodecyl-1-[(2-cyanoethyl)-(N,N-diisopropyl)]-phosphoramidite, 1,3-bis-[5-(4,4'-dimethoxytrityloxy)pentylamido]propyl-2-[(2-cyanoethyl)-(N,N-diisopropyl)]-phosphoramidite, 1-[5-(4,4'-dimethoxytrityloxy)pentylamido]-3-[5-fluorenomethoxycarbonyloxy pentylamido]-propyl-2-[(2-cyanoethyl)-(N,N-diisopropyl)]-phosphoramidite, Tris-2,2,2-[3-(4,4'-dimethoxytrityloxy)propyloxymethyl]ethyl-[(2-cyanoethyl)-(N,N-diisopropyl)]-phosphoramidite, succinimidyl trans-4-(maleimidylmethyl) cyclohexane-1-carboxylate (SMCC), succinimidyl 3-(2-pyridyldithio)propionate (SPDP), succinimidyl acetylthioacetate, Texas Red-X-succinimidyl ester, 5- and 6-carboxytetramethylrhodamine succinimidyl ester, bis-(4-carboxypiperidinyl)sulfonerhodamine di(succinimidyl ester), 5- and 6-((N-(5-aminopentyl)aminocarbonyl)tetramethylrhodamine, succinimidyl 4-(p-maleimidophenyl)butyrate (SMPB); N-γ-maleimidobutyryl-oxysuccinimide ester (GMBS); p-nitrophenyl iodoacetate (NPIA); 4-(4-N-maleimidophenyl)butyric acid hydrazide (MPBH); and like reagents. The above reagents are commercially available, e.g. from Glen Research (Sterling, Va.), Molecular Probes (Eugene, Oreg.), Pierce Chemical, and like reagent providers. Use of the above reagents in conventional synthetic schemes is well known in the art, e.g. Hermanson, Bioconjugate Techniques (Academic Press, New York, 1996). In particular, M may be constructed from the following reagents: dimethoxytrityl (DMT)-protected hexaethylene glycol phosphoramidite, 6-(4-Monomethoxytritylamino) hexyl-(2-cyanoethyl)-(N,N-diisopropyl)-phosphoramidite, 12-(4-Monomethoxytritylamino)dodecyl-(2-cyanoethyl)-(N,N-diisopropyl)-phosphoramidite, 2-[2-(4-Monomethoxytrityl)aminoethoxy]ethyl-(2-cyanoethyl), N,N-diisopropyl)-phosphoramidite, (S-Trityl-6-mercaptohexyl)-(2-cyanoethyl)-(N,N-diisopropyl)-phosphoramidite, 9-O-Dimethoxytrityl-triethylene glycol,1-[(2-cyanoethyl)-(N,N-diisopropyl)]-phosphoramidite, 3(4,4'Dimethoxytrityloxy) propyl-1-[(2-cyanoethyl)-(N,N-diisopropyl)]-phosphoramidite, 5'-O-Dimethoxytrityl-1',2'-Dideoxyribose-3'-[(2-cyanoethyl)-(N,N-diisopropyl)]-phosphoramidite, 18-O Dimethoxytritylhexaethyleneglycol, 1-[(2-cyanoethyl)-(N,N-diisopropyl)]-phosphoramidite, 12-(4,4'-Dimethoxytrityloxy)dodecyl-1-[(2-cyanoethyl)-(N,N-diisopropyl)]-phosphoramidite, 1,3-bis-[5-(4,4'-dimethoxytrityloxy)pentylamido]propyl-2-[(2-cyanoethyl)-(N,N-diisopropyl)]-phosphoramidite, 1-[5-(4,4'-dimethoxytrityloxy)pentylamido]-3-[5-fluorenomethoxycarbonyloxy pentylamido]-propyl-2-[(2-cyanoethyl)-(N,N-diisopropyl)]-phosphoramidite, Tris-2,2,2-[3-(4,4'-dimethoxytrityloxy)propyloxymethyl]ethyl-[(2-cyanoethyl)-(N,N-diisopropyl)]-phosphoramidite, succinimidyl trans-4-(maleimidylmethyl) cyclohexane-1-carboxylate (SMCC), succinimidyl 3-(2-pyridyldithio)propionate (SPDP), succinimidyl acetylthioacetate, succinimidyl 4-(p-maleimidophenyl)butyrate (SMPB); N-γ-maleimidobutyryl-oxysuccinimide ester (GMBS);

p-nitrophenyl iodoacetate (NPIA); and 4-(4-N-maleimidophenyl)butyric acid hydrazide (MPBH).

M may also comprise polymer chains prepared by known polymer subunit synthesis methods. Methods of forming selected-length polyethylene oxide-containing chains are well known, e.g. Grossman et al, U.S. Pat. No. 5,777,096. It can be appreciated that these methods, which involve coupling of defined-size, multi-subunit polymer units to one another, directly or via linking groups, are applicable to a wide variety of polymers, such as polyethers (e.g., polyethylene oxide and polypropylene oxide), polyesters (e.g., polyglycolic acid, polylactic acid), polypeptides, oligosaccharides, polyurethanes, polyamides, polysulfonamides, polysulfoxides, polyphosphonates, and block copolymers thereof, including polymers composed of units of multiple subunits linked by charged or uncharged linking groups. In addition to homopolymers, the polymer chains used in accordance with the invention include selected-length copolymers, e.g., copolymers of polyethylene oxide units alternating with polypropylene units. As another example, polypeptides of selected lengths and amino acid composition (i.e., containing naturally occurring or man-made amino acid residues), as hiomopolymers or mixed polymers.

In another aspect, after release, molecular tag, E, is defined by the formula:

A-M-D wherein:

A is —C(=O)R, where R is aliphatic, aromatic, alicyclic or heterocyclic having from 1 to 8 carbon atoms and 0 to 4 heteroatoms selected from the group consisting of O, S, and N; —$CH_2$—C(=O)—NH—CHO; —$SO_2$H;—$CH_2$—C(=O)O—CHO;—C(=O)NH—$(CH_2)_n$—NH—C(=O)C(=O)—$(C_6H_5)$, where n is in the range of from 2 to 12;

D is a detection group, preferably a fluorescent dye; and

M is as described above, with the proviso that the total molecular weight of A-M-D be within the range of from about 100 to about 2500 daltons.

In another aspect, D is a fluorescein and the total molecular weight of A-M-D is in the range of from about 100 to about 1500 daltons.

In another aspect, M may be synthesized from smaller molecules that have functional groups that provide for linking of the molecules to one another, usually in a linear chain. Such functional groups include carboxylic acids, amines, and hydroxy- or thiol-groups. In accordance with the present invention the charge-imparting moiety may have one or more side groups pending from the core chain. The side groups have a functionality to provide for linking to a label or to another molecule of the charge-imparting moiety. Common functionalities resulting from the reaction of the functional groups employed are exemplified by forming a covalent bond between the molecules to be conjugated. Such functionalities are disulfide, amide, thioamide, dithiol, ether, urea, thiourea, guanidine, azo, thioether, carboxylate and esters and amides containing sulfur and phosphorus such as, e.g., sulfonate, phosphate esters, sulfonamides, thioesters, etc., and the like.

Attaching Molecular Tags to Binding Moieties

Extensive guidance can be found in the literature for covalently linking molecular tags to binding compounds, such as antibodies, e.g. Hermanson, Bioconjugate Techniques, (Academic Press, New York, 1996), and the like. In one aspect of the invention, one or more molecular tags are attached directly or indirectly to common reactive groups on a binding compound. Common reactive groups include amine, thiol, carboxylate, hydroxyl, aldehyde, ketone, and the like, and may be coupled to molecular tags by commercially available cross-linking agents, e.g. Hermanson (cited above); Haugland, Handbook of Fluorescent Probes and Research Products, Ninth Edition (Molecular Probes, Eugene, Oreg., 2002). In one embodiment, an NHS-ester of a molecular tag is reacted with a free amine on the binding compound.

Figure 1P:
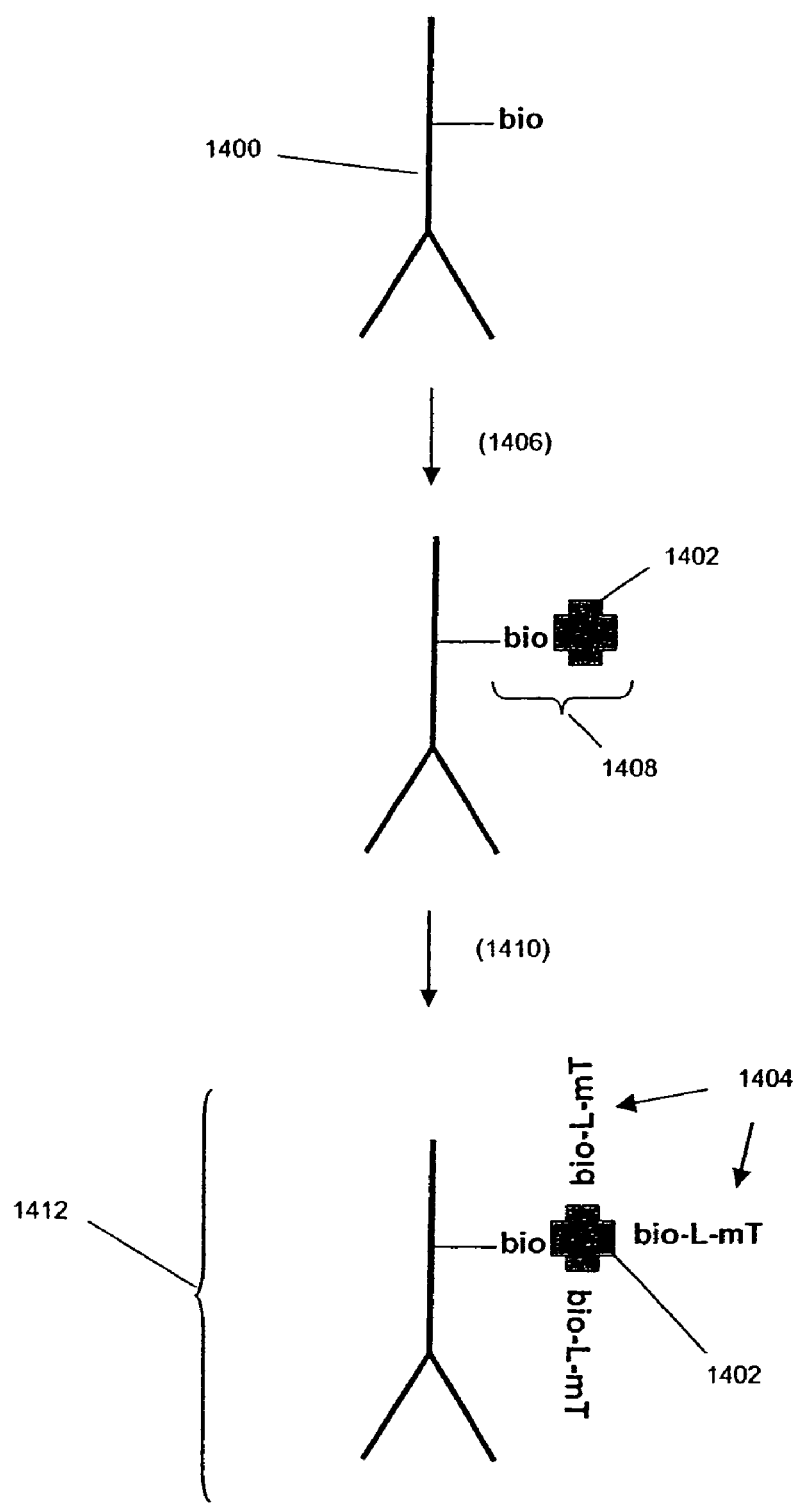
FIG. 1P illustrates a method for generating a sensitizer-treated membrane for use with the invention that employs an avidin or streptavidin bridge between a biotinylated lipophilic moiety and a biotinylated sensitizer.

In a preferred embodiment illustrated in FIG. 1P, binding compounds comprise a biotinylated antibody (1400) as a binding moiety. Molecular tags (1404) are attached to binding moiety (1400) by way of avidin or streptavidin bridge (1402). Preferably, in operation, binding moiety (1400) is first reacted with membrane-bound analytes, after which avidin or streptavidin is added (1406) to form complex (1408). To complexes (1408) are added (1410) biotinylated molecular tags to form binding compound (1412).

Once each of the binding compounds is separately derivatized by a different molecular tag, it is pooled with other binding compounds to form a plurality of binding compounds. Usually, each different kind of binding compound is present in a composition in the same proportion; however, proportions may be varied as a design choice so that one or a subset of particular binding compounds are present in greater or lower proportion depending on the desirability or requirements for a particular embodiment or assay. Factors that may affect such design choices include, but are not limited to, antibody affinity and avidity for a particular target, relative prevalence of a target, fluorescent characteristics of a detection moiety of a molecular tag, and the like.

Lipophilic Sensitizers for Producing Active Species

A sensitizer is a chemical compound that can be induced, or activated, to produce an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background because beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide, and the like. Illustrative quenchers for active species that cause oxidation include polyenes, carotenoids, vitamin E, vitamin C, amino acid-pyrrole N-conjugates of tyrosine, histidine, and glutathione, and the like, e.g. Beutner et al, Meth. Enzymol., 319: 226–241 (2000).

In accordance with the invention, membranes in a sample are combined with a lipophilic sensitizer to form a sensitizer-treated membrane. A lipophilic sensitizer is formed by derivatizing a sensitizer either directly or indirectly with a lipophilic moiety that allows a sensitizer to be stably anchored in a biological membrane. A lipophilic compound with a reactive functionality may be reacted with a complementary functionality on a sensitizer or a cross-linking agent to produce a sensitizer having a covalently attached lipophilic group for anchoring it in a membrane.

An important consideration for a lipophilic sensitizer and cleavable linkage is that they not be so far from one another that when a binding compound is bound to a membrane-associated analyte the active species generated by the sensitizer diffuses and loses its activity before it can interact with the cleavable linkage. Accordingly, during a cleavage step, a sensitizer preferably is within 1000 nm, preferably 20–100 nm of a bound cleavage-inducing moiety. This effective range of a cleavage-inducing moiety is referred to herein as its "effective proximity."

Sensitizers for generating active species include enzymes, such as oxidases, such as glucose oxidase, xanthene oxidase, D-amino acid oxidase, NADH-FMN oxidoreductase, galactose oxidase, glyceryl phosphate oxidase, sarcosine oxidase, choline oxidase and alcohol oxidase, that produce hydrogen peroxide, horse radish peroxidase, that produces hydroxyl radical, various dehydrogenases that produce NADH or NADPH, urease that produces ammonia to create a high local pH.

A preferred sensitizer for use with the invention is a photosensitizer that generates singlet oxygen from molecular oxygen in response to photoexcitation. As used herein, "photosensitizer" refers to a light-adsorbing molecule that when activated by light converts molecular oxygen into singlet oxygen. Suitable photosensitizers having lipophilic moieties are disclosed in the following references: Young et al, U.S. Pat. No. 6,375,930; and Young et al, U.S. patent application Ser. No. 2002/0006378, which are incorporated by reference. Additional photosensitizers that may be derivatized with lipophilic groups or capture moieties, such as biotin, and used with the invention are disclosed in the following references: Sessler et al, U.S. Pat. No. 5,292,414; Masuya et al, U.S. Pat. No. 5,344,928; McCapra, U.S. Pat. No. 5,705,622; Levy et al, U.S. Pat. No. 4,883,790; Meunier et al, U.S. Pat. No. 5,141,911; and the like, which are incorporated by reference. The following references disclose the use of conjugates between biotin and lipophilic moieties to anchor biotinylated molecules to membranes via an avidin or streptavidin: Plant et al, Anal. Biochem., 176: 420–426 (1989); Bayer et al, Biochim. Biophys. Acta, 550: 464–473 (1979); Ramirez et al, J. Chromatogr. A, 971: 117–127 (2002); and the like, which are incorporated by reference.

Photosensitizers include dyes and aromatic compounds, and are usually compounds comprised of covalently bonded atoms, usually with multiple conjugated double or triple bonds. The compounds typically absorb light in the wavelength range of about 200 to about 1,100 nm, usually, about 300 to about 1,000 nm, preferably, about 450 to about 950 nm, with an extinction coefficient at its absorbance maximum greater than about 500 $M^{-1}$ $cm^{-1}$, preferably, about 5,000 $M^{-1}$ $cm^{-1}$, more preferably, about 50,000 $M^{-1}$ $cm^{-1}$, at the excitation wavelength. The lifetime of an excited state produced following absorption of light in the absence of oxygen will usually be at least about 100 nanoseconds, preferably, at least about 1 millisecond. In general, the lifetime must be sufficiently long to permit cleavage of a linkage in a reagent in accordance with the present invention. Such a reagent is normally present at concentrations as discussed below. The photosensitizer excited state usually has a different spin quantum number (S) than its ground state and is usually a triplet (S=1) when the ground state, as is usually the case, is a singlet (S=0). Preferably, the photosensitizer has a high intersystem crossing yield. That is, photoexcitation of a photosensitizer usually produces a triplet state with an efficiency of at least about 10%, desirably at least about 40%, preferably greater than about 80%.

Photosensitizers chosen are relatively photostable and, preferably, do not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3–6 of the periodic table, especially iodine or bromine, or they may have extended aromatic structures.

A large variety of light sources are available to activate photosensitizers to generate singlet oxygen. Both polychromatic and monochromatic sources may be used as long as the source is sufficiently intense to produce enough singlet oxygen in a practical time duration. The length of the irradiation is dependent on the nature of the photosensitizer, the nature of the cleavable linkage, the power of the source of irradiation, and its distance from the sample, and so forth. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include, by way of illustration and not limitation, lasers such as, e.g., helium-neon lasers, argon lasers, YAG lasers, He/Cd lasers, and ruby lasers; photodiodes; mercury, sodium and xenon vapor lamps; incandescent lamps such as, e.g., tungsten and tungsten/halogen; flash lamps; and the like.

Examples of photosensitizers that may be utilized in the present invention are those that have the above properties and are enumerated in the following references: Turro, Modern Molecular Photochemistry (cited above); Singh and Ullman, U.S. Pat. No. 5,536,834; Li et al, U.S. Pat. No. 5,763,602; Ullman, et al., Proc. Natl. Acad. Sci. USA 91, 5426–5430 (1994); Strong et al, Ann. New York Acad. Sci., 745: 297–320 (1994); Martin et al, Methods Enzymol., 186: 635–645 (1990);Yarmush et al, Crit. Rev. Therapeutic Drug Carrier Syst., 10: 197–252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516, 636; Wohrle, Chimia, 45: 307–310 (1991); Thetford, European patent publ. 0484027; Sessler et al, SPIE, 1426: 318–329 (1991); Madison et al, Brain Research, 522: 90–98 (1990); Polo et al, Inorganica Chimica Acta, 192: 1–3 (1992); Demas et al, J. Macromol. Sci., A25: 1189–1214 (1988); and the like. In one embodiment, photosensitizers used in the invention are porphyrins, e.g. as described in Roelant, U.S. Pat. No. 6,001,573, which is incorporated by reference. Many porphyrins suitable for use with the invention are available commercially, e.g. Frontier Scientific, Inc. (Logan, Utah); Molecular Probes, Inc. (Eugene, Oreg.); and the like. Exemplary photosensitizers are listed in Table 1b.

TABLE 1b

Exemplary Photosensitizers

| | |
|---|---|
| Hypocrellin A | Tetraphenylporphyrin |
| Hypocrellin B | Halogenated derivatives of rhodamine dyes |
| Hypericin | metallo-Porphyrins |
| Halogenated derivatives of fluorescein dyes | Phthalocyanines |
| Rose bengal | Naphthalocyanines |
| Merocyanine 540 | Texaphyrin-type macrocycles |
| Methylene blue | Hematophorphyrin |
| 9-Thioxanthone | 9,10-Dibromoanthracene |
| Chlorophylls | Benzophenone |
| Phenaleone | Chlorin e6 |
| Protoporphyrin | Perylene |
| Benzoporphryin A monacid | Benzoporphyrin B monacid |

Treating Membranes with Lipophilic Sensitizers

Lipophilic sensitizers can be incorporated into lipid membranes in an orientation and manner similar to that of phospholipids where the hydrophobic moiety comprising of the hydrocarbon chains can orient inward and the more hydrophilic entities can orient outwards. Thus, as in the usual cellular membranes, the hydrocarbon portion of the lipophilic sensitizer can be incorporated into the lipid environment whereas the hydrophilic sensitizer portion can be exposed to the aqueous interface at the membrane surface.

Where intact cellular structures are required, the methods used to incorporate lipophilic sensitizers into the cells preferably cause minimal disruption of the cell and of the integrity of membranes. In addition, the cells can be fixed and treated with routine histochemical or cytochemical procedures, where the procedure preferably does not affect the incorporation.

The membranes can be labeled with lipophilic sensitizers according to the method described in Barak and Webb (1981) J. Cell Biol. 90:595–604. Typically, the membrane, such as the intact cell, is contacted with the compounds of the invention, preferably in an aqueous media. The aqueous media can be water, water and organic solvent, such as DMSO, DMF, DMA, or a mixture thereof, and can contain buffers such as phosphate, acetate, tris, and the like. The membranes and lipophilic sensitizer are contacted for between 1 min. to about 1 week, preferably about 1 h to 76 h, more preferably about 2 h to about 48 h, or any integer in between. The formulations may additionally be subjected to chemical or mechanical treatment, such as the addition of a surfactant (Tween 80, for example), shaking, stirring, electroporation, and the like. Alternatively, the formulation can be heated to about 30° C. to 50° C., preferably about 35° C. to about 40° C., until labeling is achieved. After labeling, the unbound components can be removed by washing, or by centrifugation, for example, and the sensitizer-labeled cells or membranes isolated.

Figure 1Q:
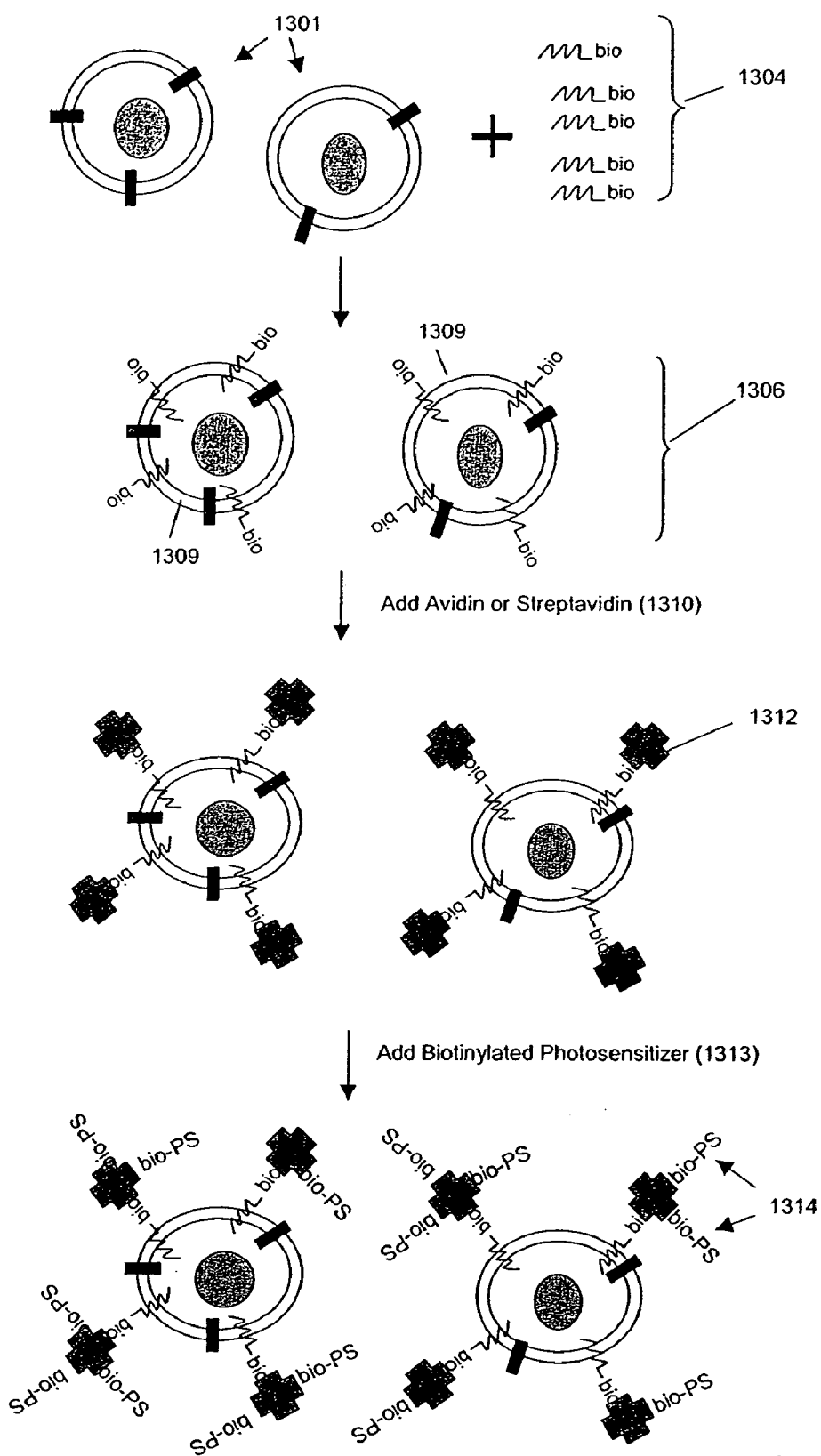
FIG. 1Q illustrates a method of generating binding compounds derivatized with releasable molecular tags through an avidin or streptavidin bridge between a biotinylated binding moiety and a biotinylated molecular tag precursor compound.

Alternatively, a capture moiety, such as biotin, having a lipophilic group may be anchored in a membrane followed by conjugation to avidin or streptavidin and finally by attachment of a biotinylated sensitizer via the avidin or streptavidin, as illustrated in FIG. 1Q. Cells (1301) are combined with biotin having a lipophilic moiety (1304) (referred to below as biotin-G) to form a population of cells (1306) having membranes containing free biotin. To this population is added avidin or streptavidin (1310) to form biotin-avidin or biotin-streptavidin complexes (1312) on the cell surfaces. These cells are then combined (1313) with biotinylated photosensitizers to form complexes (1312) on the cell surfaces that comprise sensitizer-treated membranes.

Separation of Released Molecular Tags

As mentioned above, molecular tags are designed for separation by a separation technique that can distinguish molecular tags based on one or more physical, chemical, and/or optical characteristics. As also mentioned above, separation techniques that may be used with the various embodiments of the invention include normal phase or reverse phase HPLC, ion exchange HPLC, capillary electrochromatography, mass spectroscopy, gas phase chromatography, and the like. Preferably, the separation technique selected is capable of providing quantitative information as well as qualitative information about the presence or absence of molecular tags (and therefore, corresponding analytes). In one aspect, a liquid phase separation technique is employed so that a solution, e.g. buffer solution, reaction solvent, or the like, containing a mixture of molecular tags is processed to bring about separation of individual kinds of molecular tags. Usually, such separation is accompanied by the differential movement of molecular tags from such a starting mixture along a path until discernable peaks or bands form that correspond to regions of increased concentration of the respective molecular tags. Such a path may be defined by a fluid flow, electric field, magnetic field, or the like. The selection of a particular separation technique depends on several factors including the expense and convenience of using the technique, the resolving power of the technique given the chemical nature of the molecular tags, the number of molecular tags to be separated, the type of detection mode employed, and the like. Preferably, molecular tags are electrophoretically separated to form an electropherogram in which the separated molecular tags are represented by distinct peaks.

A. Electrophoretic Separation

Methods for electrophoresis of are well known and there is abundant guidance for one of ordinary skill in the art to make design choices for forming and separating particular pluralities of molecular tags. The following are exemplary references on electrophoresis: Krylov et al, Anal. Chem., 72: 111R–128R (2000); P. D. Grossman and J. C. Colburn, Capillary Electrophoresis: Theory and Practice, Academic Press, Inc., NY (1992); U.S. Pat. Nos. 5,374,527; 5,624,800; 5,552,028; ABI PRISM 377 DNA Sequencer User's Manual, Rev. A, January 1995, Chapter 2 (Applied Biosystems, Foster City, Calif.); and the like. In one aspect, molecular tags are separated by capillary electrophoresis. Design choices within the purview of those of ordinary skill include but are not limited to selection of instrumentation from several commercially available models, selection of operating conditions including separation media type and concentration, pH, desired separation time, temperature, voltage, capillary type and dimensions, detection mode, the number of molecular tags to be separated, and the like.

In one aspect of the invention, during or after electrophoretic separation, the molecular tags are detected or identified by recording fluorescence signals and migration times (or migration distances) of the separated compounds, or by constructing a chart of relative fluorescent and order of migration of the molecular tags (e.g., as an electropherogram). To perform such detection, the molecular tags can be illuminated by standard means, e.g. a high intensity mercury vapor lamp, a laser, or the like. Typically, the molecular tags are illuminated by laser light generated by a He—Ne gas laser or a solid-state diode laser. The fluorescence signals can then be detected by a light-sensitive detector, e.g., a photomultiplier tube, a charged-coupled device, or the like. Exemplary electrophoresis detection systems are described elsewhere, e.g., U.S. Pat. Nos. 5,543,026; 5,274,240; 4,879,012; 5,091,652; 6,142,162; or the like. In another aspect, molecular tags may be detected electrochemically detected, e.g. as described in U.S. Pat. No. 6,045,676.

Electrophoretic separation involves the migration and separation of molecules in an electric field based on differences in mobility. Various forms of electrophoretic separation include, by way of example and not limitation, free zone electrophoresis, gel electrophoresis, isoelectric focusing, isotachophoresis, capillary electrochromatography, and micellar electrokinetic chromatography. Capillary electrophoresis involves electroseparation, preferably by electrokinetic flow, including electrophoretic, dielectrophoretic and/or electroosmotic flow, conducted in a tube or channel of from about 1 to about 200 micrometers, usually, from about 10 to about 100 micrometers cross-sectional dimensions. The capillary may be a long independent capillary tube or a channel in a wafer or film comprised of silicon, quartz, glass or plastic.

In capillary electroseparation, an aliquot of the reaction mixture containing the molecular tags is subjected to electroseparation by introducing the aliquot into an electroseparation channel that may be part of, or linked to, a capillary device in which the amplification and other reactions are performed. An electric potential is then applied to the electrically conductive medium contained within the channel to effectuate migration of the components within the combination. Generally, the electric potential applied is sufficient to achieve electroseparation of the desired components according to practices well known in the art. One skilled in the art will be capable of determining the suitable electric potentials for a given set of reagents used in the present invention and/or the nature of the cleaved labels, the nature of the reaction medium and so forth. The parameters for the electroseparation including those for the medium and the electric potential are usually optimized to achieve maximum separation of the desired components. This may be achieved empirically and is well within the purview of the skilled artisan.

Detection may be by any of the known methods associated with the analysis of capillary electrophoresis columns including the methods shown in U.S. Pat. No. 5,560,811 (column 11, lines 19–30), U.S. Pat. Nos. 4,675,300, 4,274,240 and 5,324,401, the relevant disclosures of which are incorporated herein by reference. Those skilled in the electrophoresis arts will recognize a wide range of electric potentials or field strengths may be used, for example, fields of 10 to 1000 V/cm are used with about 200 to about 600 V/cm being more typical. The upper voltage limit for commercial systems is about 30 kV, with a capillary length of about 40 to about 60 cm, giving a maximum field of about 600 V/cm. For DNA, typically the capillary is coated to reduce electroosmotic flow, and the injection end of the capillary is maintained at a negative potential.

For ease of detection, the entire apparatus may be fabricated from a plastic material that is optically transparent, which generally allows light of wavelengths ranging from about 180 to about 1500 run, usually about 220 to about 800 nm, more usually about 450 to about 700 nm, to have low transmission losses. Suitable materials include fused silica, plastics, quartz, glass, and so forth.

Figure 16A:
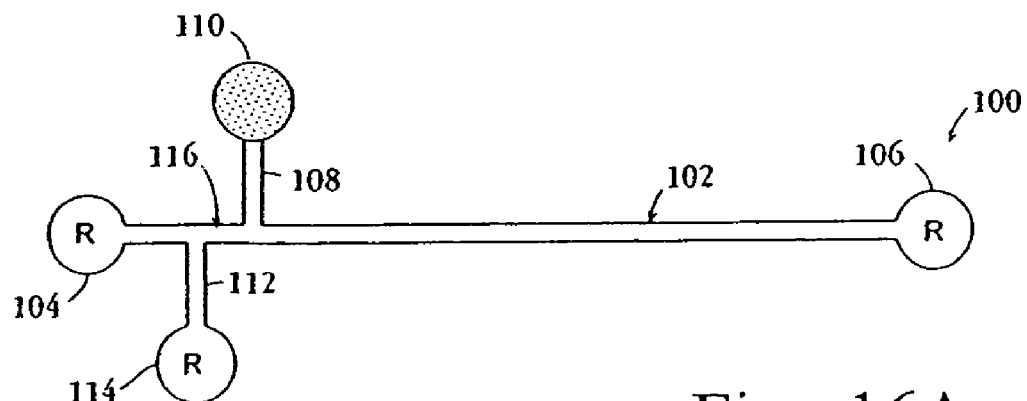
FIGS. 16A–16C illustrate steps in practicing the method of the invention using a microfluidics/CE device.
Figure 16B:
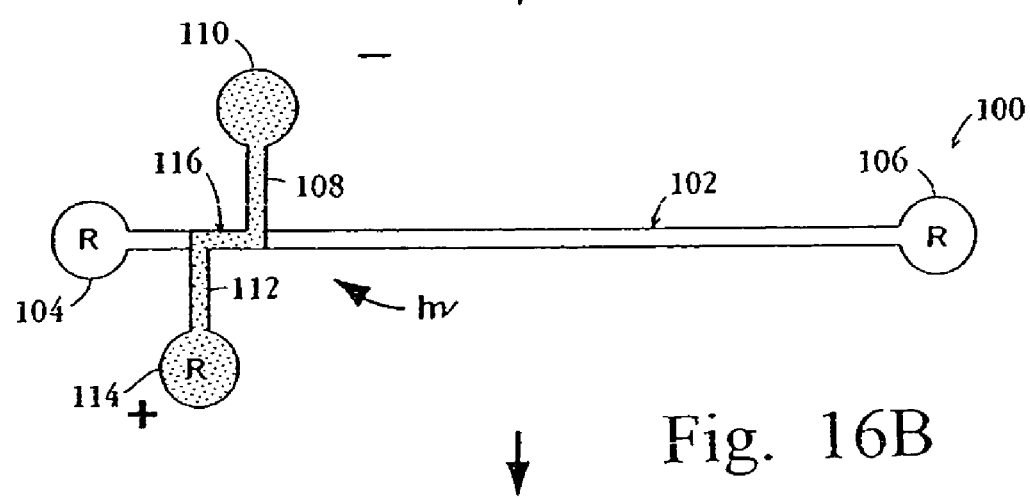
Figure 16C:
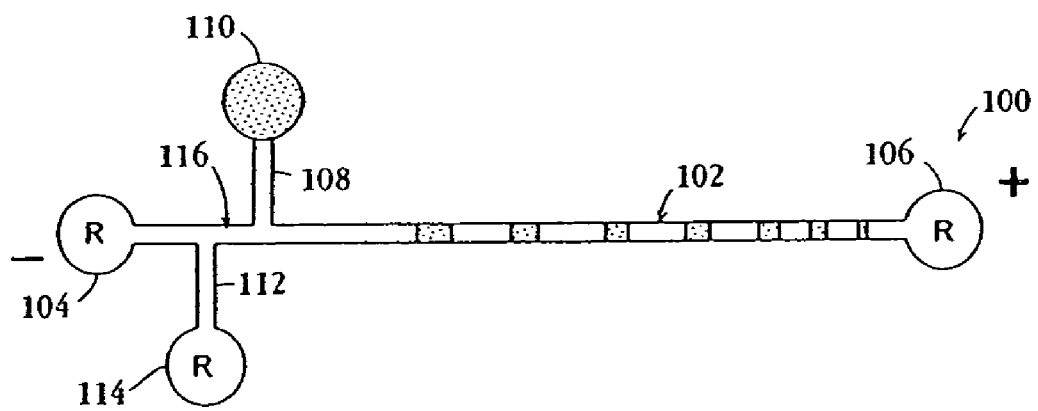

In one aspect of the invention, molecular tags are separated by electrophoresis in a microfluidics device, as illustrated diagrammatically in FIGS. 16A–16C. Microfluidics devices are described in a number of domestic and foreign Letters Patent and published patent applications. See, for example, U.S. Pat. Nos. 5,750,015; 5,900,130; 6,007,690; and WO 98/45693; WO 99/19717 and WO 99/15876. Conveniently, an aliquot, generally not more than about 5 µl, is transferred to the sample reservoir of a microfluidics device, either directly tlrough electrophoretic or pneumatic injection into an integrated system or by syringe, capillary or the like. The conditions under which the separation is performed are conventional and will vary with the nature of the products.

By way of illustration, FIGS. 16A–16C show a microchannel network 100 in a microfluidics device of the type detailed in the application noted above, for sample loading and electrophoretic separation of a sample of probes and tags produced in the assay above. Briefly, the network includes a main separation channel 102 terminating at upstream and downstream reservoirs 104, 106, respectively. The main channel is intersected at offset axial positions by a side channel 108 that terminates at a reservoir 110, and a side channel 112 that terminates at a reservoir 114. The offset between the two-side channels forms a sample loading zone 116 within the main channel.

In operation, an assay mixture is placed in sample reservoir 110, illustrated in FIG. 16. As noted, the assay mixture contains one or more target cells with surface-bound cleaving agent, one or more protein probes, and optionally, molecular tag standard. The assay reaction, involving initial probe binding to target cell(s), followed by cleavage of probe linkers in probe-bound cells, may be carried out in sample reservoir 110, or alternatively, the assay reactions can be carried out in another reaction vessel, with the reacted sample components the added to the sample reservoir.

To load released molecular tags into the sample-loading zone, an electric field is applied across reservoirs 110, 114, in the direction indicated in FIG. 16B, wherein negatively charged released molecular tags are drawn from reservoir 110 into loading zone 116, while uncharged or positively charged sample components remain in the sample reservoir. The released tags in the loading zone can now be separated by conventional capillary electrophoresis, by applying an electric filed across reservoirs 104, 106, in the direction indicated in FIG. 16C.

From the resulting electrophoretic pattern, the molecular tags, and corresponding analytes, can be identified. This is typically done by placing a fluorescence detector near the downstream end of the separation channel, and constructing a electropherogram of the separated molecular tags, first to determine the separation characteristic (in this case, electrophoretic mobility) as above, and secondly, to measure signal intensity, e.g., peak height or peak area, as a measure of the relative amount of tag associated with each probe. Methods for detecting and quantifying levels of a detectable probe are well known. In one preferred method, the molecular tags are fluorescent labeled. A standard fluorescence-emission source is directed against a detection zone in a downstream portion of the separation medium, and fluorescence emission of the zone is measured by a standard light detector. The signal height or area recorded provides a measure of product and substrate concentration in the sample.

With the above detection information, it is now possible to assign each detected molecular tag to a particular probe in the probe set, and to compare the relative levels of each detectable probe, as a measure of its relatively substrate conversion or ligand binding.

B. Chromatographic Separation

In one aspect of the invention, pluralities of molecular tags are designed for separation by chromatography based on one or more physical characteristics that include but are not limited to molecular weight, shape, solubility, pKa, hydrophobicity, charge, polarity, or the like. A chromatographic separation technique is selected based on parameters such as column type, solid phase, mobile phase, and the like, followed by selection of a plurality of molecular tags that may be separated to form distinct peaks or bands in a single operation. Several factors determine which HPLC technique is selected for use in the invention, including the number of molecular tags to be detected (i.e. the size of the plurality), the estimated quantities of each molecular tag that will be generated in the assays, the availability and ease of synthesizing molecular tags that are candidates for a set to be used in multiplexed assays, the detection modality employed. and the availability, robustness, cost, and ease of operation of HPLC instrumentation, columns, and solvents. Generally, columns and techniques are favored that are suitable for analyzing limited amounts of sample and that provide the highest resolution separations. Guidance for making such selections can be found in the literature, e.g. Snyder et al, Practical HPLC Method Development, (John Wiley & Sons, New York, 1988); Millner, "High Resolution Chromatography: A Practical Approach", Oxford University Press, New York (1999), Chi-San Wu, "Column Handbook for Size Exclusion Chromatography", Academic Press, San Diego (1999), and Oliver, "HPLC of Macromolecules: A Practical Approach, Oxford University Press", Oxford, England (1989). In particular, procedures are available for systematic development and optimization of chromatographic separations given conditions, such as column type, solid phase, and the like, e.g. Haber et al, J. Chromatogr. Sci., 38: 386–392 (2000); Outinen et al, Eur. J. Pharm. Sci., 6: 197–205 (1998); Lewis et al, J. Chromatogr., 592: 183–195 and 197–208 (1992); and the like.

In one aspect, initial selections of molecular tag candidates are governed by the physiochemical properties of molecules typically separated by the selected column and stationary phase. The initial selections are then improved empirically by following conventional optimization procedure, as described in the above reference, and by substituting more suitable candidate molecular tags for the separation objectives of a particular embodiment. In one aspect, separation objectives of the invention include (i) separation of the molecular tags of a plurality into distinguishable peaks or bands in a separation time of less than 60 minutes, and more preferably in less than 40 minutes, and still more preferably in a range of between 10 to 40 minutes, (ii) the formation of peaks or bands such that any pair has a resolution of at least 1.0, more preferably at least 1.25, and still more preferably, at least 1.50, (iii) column pressure during separation of less than 150 bar, (iv) separation temperature in the range of from 25° C. to 90° C., preferably in the range of from 35° C. to 80° C., and (v) the plurality of distinguishable peaks is in the range of from 5 to 30 and all of the peaks in the same chromatogram. As used herein, "resolution" in reference to two peaks or bands is the distance between the two peak or band centers divided by the average base width of the peaks, e.g. Snyder et al (cited above).

A chromatographic method is used to separate molecular tags based on their chromatographic properties. A chromatographic property can be, for example, a retention time of a molecular tag on a specific chromatographic medium under defined conditions, or a specific condition under which a molecular tag is eluted from a specific chromatographic medium. A chromatographic property of a molecular tag can also be an order of elution, or pattern of elution, of a molecular tag contained in a group or set of molecular tags being chromatographically separated using a specific chromatographic medium under defined conditions. A chromatographic property of a molecular tag is determined by the physical properties of the molecular tag and its interactions with a chromatographic medium and mobile phase. Defined conditions for chromatography include particular mobile phase solutions, column geometry, including column diameter and length, pH, flow rate, pressure and temperature of column operation, and other parameters that can be varied to obtain the desired separation of molecular tags. A molecular tag, or chromatographic property of a molecular tag, can be detected using a variety of chromatography methods.

Sets of molecular tags detected in a single experiment generally are a group of chemically related molecules that differ by mass, charge, mass-charge ratio, detectable tag, such as differing fluorophores or isotopic labels, or other unique characteristic. Therefore, both the chemical nature of the molecular tag and the particular differences among molecular tags in a group of molecular tags can be considered when selecting a suitable chromatographic medium for separating molecular tags in a sample.

Separation of molecular tags by liquid chromatography can be based on physical characteristics of molecular tags such as charge, size and hydrophobicity of molecular tags, or functional characteristics such as the ability of molecular tags to bind to molecules such as dyes, lectins, drugs, peptides and other ligands on an affinity matrix. A wide variety of chromatographic media are suitable for separation of molecular tag based on charge, size, hydrophobicity and other chromatographic properties of molecular tags. Selection of a particular chromatographic medium will depend upon the properties of molecular tags employed.

Separated molecular tags can be detected using a variety of analytical methods, including detection of intrinsic properties of molecular tags, such as absorbance, fluorescence or electrochemical properties, as well as detection of a detection group or moiety attached to a molecular tag. Although not required, a variety of detection groups or moieties can be attached to molecular tags to facilitate detection after chromatographic separation.

Detection methods for use with liquid chromatography are well known, commercially available, and adaptable to automated and high-throughput sampling. The detection method selected for analysis of molecular tags will depend upon whether the molecular tags contain a detectable group or moiety, the type of detectable group used, and the physicochemical properties of the molecular tag and detectable group, if used. Detection methods based on fluorescence, electrolytic conductivity, refractive index, and evaporative light scattering can be used to detect various types of molecular tags.

A variety of optical detectors can be used to detect a molecular tag separated by liquid chromatography. Methods for detecting nucleic acids, polypeptides, peptides, and other macromolecules and small molecules using ultraviolet (UV)/visible spectroscopic detectors are well known, making UV/visible detection the most widely used detection method for HPLC analysis. Infrared spectrophotometers also can be used to detect macromolecules and small molecules when used with a mobile phase that is a transparent polar liquid.

Variable wavelength and diode-array detectors represent two commercially available types of UV/visible spectrophotometers. A useful feature of some variable wavelength UV detectors is the ability to perform spectroscopic scanning and precise absorbance readings at a variety of wavelengths while the peak is passing through the flowcell. Diode array technology provides the additional advantage of allowing absorbance measurements at two or more wavelengths, which permits the calculation of ratios of such absorbance measurements. Such absorbance rationing at multiple wavelengths is particularly helpful in determining whether a peak represents one or more than one molecular tag.

Fluorescence detectors can also be used to detect fluorescent molecular tags, such as those containing a fluorescent detection group and those that are intrinsically fluorescent. Typically, fluorescence sensitivity is relatively high, providing an advantage over other spectroscopic detection methods when molecular tags contain a fluorophore. Although molecular tags can have detectable intrinsic fluorescence, when a molecular tag contains a suitable fluorescent detection group, it can be possible to detect a single molecular tag in a sample.

Electrochemical detection methods are also useful for detecting molecular tags separated by HPLC. Electrochemical detection is based on the measurement of current resulting from oxidation or reduction reaction of the molecular tags at a suitable electrode. Since the level of current is directly proportional to molecular tag concentration, electrochemical detection can be used quantitatively, if desired.

Evaporative light scattering detection is based on the ability of particles to cause photon scattering when they traverse the path of a polychromatic beam of light. The liquid effluent from an HPLC is first nebulized and the resultant aerosol mist, containing the molecular tags, is directed through a light beam. A signal is generated that is proportional to the amount of the molecular tag present in a sample, and is independent of the presence or absence of detectable groups such as chromophores, fluorophores or electroactive groups. Therefore, the presence of a detection group or moiety on a molecular tag is not required for evaporative light scattering detection.

Mass spectrometry methods also can be used to detect molecular tags separated by HPLC. Mass spectrometers can resolve ions with small mass differences and measure the mass of ions with a high degree of accuracy and sensitivity. Mass spectrometry methods are well known in the art (see Burlingame et al. *Anal. Chem.* 70:647R-716R (1998); Kinter and Sherman, Protein Sequencing and Identification Using Tandem Mass Spectrometry Wiley-Interscience, New York (2000)).

Analysis of data obtained using any detection method, such as spectral deconvolution and quantitative analysis can be manual or computer-assisted, and can be performed using automated methods. A variety of computer programs can be used to determine peak integration, peak area, height and retention time. Such computer programs can be used for convenience to determine the presence of a molecular tag qualitatively or quantitatively. Computer programs for use with HPLC and corresponding detectors are well known to those skilled in the art and generally are provided with commercially available HPLC and detector systems.

A variety of commercially available systems are well-suited for high tlrougliput analysis of molecular tags. Those skilled in the art can determine appropriate equipment, such as automated sample preparation systems and autoinjection systems, useful for automating HPLC analysis of molecular tags. Automated methods can be used for high-throughput analysis of molecular tags, for example, when a large number of samples are being processes or for multiplexed application of the methods of the invention for detecting target analytes. An exemplary HPLC instrumentation system suitable for use with the present invention is the Agilent 1100 Series HPLC system (Agilent Technologies, Palo Alto, Calif).

Those skilled in the art will be aware of quality control measures useful for obtaining reliable analysis of molecular tags, particular when analysis is performed in a high-throughput format. Such quality control measures include the use of external and internal reference standards, analysis of chromatograph peak shape, assessment of instrument performance, validation of the experimental method, for example, by determining a range of linearity, recovery of sample, solution stability of sample, and accuracy of measurement.

C. Separation by Mass Spectrometry

Mass spectrometry methods are well known in the art (see Burlingame et al. Anal. Chem. 70:647R-716R (1998); Kinter and Sherman, Protein Sequencing and Identification Using Tandem Mass Spectrometry Wiley-Interscience, New York (2000)). The basic processes associated with a mass spectrometry method are the generation of gas-phase ions derived from the sample, and the measurement of their mass.

The movement of gas-phase ions can be precisely controlled using electromagnetic fields generated in the mass spectrometer. The movement of ions in these electromagnetic fields is proportional to the m/z of the ion and this forms the basis of measuring the n/z and therefore the mass of a sample. The movement of ions in these electromagnetic fields allows the ions to be contained and focused which accounts for the high sensitivity of mass spectrometry. During the course of m/z measurement, ions are transmitted with high efficiency to particle detectors that record the arrival of these ions. The quantity of ions at each m/z is demonstrated by peaks on a graph where the x axis is m/z and the y axis is relative abundance. Different mass spectrometers have different levels of resolution, that is, the ability to resolve peaks between ions closely related in mass. The resolution is defined as R=m/delta m, where m is the ion mass and delta m is the difference in mass between two peaks in a mass spectrum. For example, a mass spectrometer with a resolution of 1000 can resolve an ion with a m/z of 100.0 from an ion with a m/z of 100.1.

Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nano-spray and microspray or matrix-assisted laser desorption. Exemplary mass analyzers include a quadrupole mass filter, ion trap mass analyzer and time-of-flight mass analyzer.

The ion formation process is a starting point for mass spectrum analysis. Several ionization methods are available and the choice of ionization method depends on the sample to be analyzed. For example, for the analysis of polypeptides a relatively gentle ionization procedure such as electrospray ionization (ESI) can be desirable. For ESI, a solution containing the sample is passed through a fine needle at high potential, which creates a strong electrical field resulting in a fine spray of highly charged droplets that is directed into the mass spectrometer. Other ionization procedures include, for example, fast-atom bombardment (FAB), which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix. Other ionization procedures known in the art include, for example, plasma and glow discharge, plasma desorption ionization, resonance ionization, and secondary ionization. A tag reporter can become ionized prior to, during, or after cleavage from the tagged probe.

Electrospray ionization (ESI) has several properties that are useful for the invention described herein. For example, ESI can be used for biological molecules such as polypeptides that are difficult to ionize or vaporize. In addition, the efficiency of ESI can be very high which provides the basis for highly sensitive measurements. Furthermore, ESI produces charged molecules from solution, which is convenient for analyzing tag reporters that are in solution. In contrast, ionization procedures such as MALDI require crystallization of the sample prior to ionization.

Since ESI can produce charged molecules directly from solution, it is compatible with samples from liquid chromatography systems. For example, a mass spectrometer can have an inlet for a liquid chromatography system, such as an HPLC, so that fractions flow from the chromatography column into the mass spectrometer. This in-line arrangement of a liquid chromatography system and mass spectrometer is sometimes referred to as LC-MS. A LC-MS system can be used, for example, to separate un-cleaved or partially cleaved tag reporters from cleaved tag reporters before mass spectrometry analysis. In addition, chromatography can be used to remove salts or other buffer components from the tag reporter sample before mass spectrometry analysis. For example, desalting of a sample using a reversed-phase HPLC column, in-line or off-line, can be used to increase the efficiency of the ionization process and thus improve sensitivity of detection by mass spectrometry.

A variety of mass analyzers are available that can be paired with different ion sources. Different mass analyzers have different advantages as known to one skilled in the art and as described herein. The mass spectrometer and methods chosen for detection depends on the particular assay, for example, a more sensitive mass analyzer can be used when a small amount of ions are generated for detection. Several types of mass analyzers and mass spectrometry methods are described below.

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to function as a lens or focusing system in regions of the mass spectrometer where ion transmission is needed without mass filtering. This will be of use in tandem mass spectrometry as described further below.

A quadrupole mass analyzer, as well as the other mass analyzers described herein, can be programmed to analyze a defined m/z or mass range. This property of mass spectrometers is useful for the invention described herein. Since the mass range of cleaved tag reporters will be known prior to an assay, a mass spectrometer can be programmed to transmit ions of the projected correct mass range while excluding ions of a higher or lower mass range. The ability to select a mass range can decrease the background noise in the assay and thus increase the signal-to-noise ratio. In addition, a defined mass range can be used to exclude analysis of any un-cleaved or partially-cleaved tagged probes, which would be of higher mass than the mass of the fully-cleaved tagged probes (tag reporters). Therfore, the mass spectrometer can accomplish an inherent separation step as well as detection and identification of the tag reporters.

Ion trap mass spectrometry utilizes an ion trap mass analyzer. In these mass analyzers, fields are applied so that ions of all m/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis is accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected m/z. One advantage to ion traps is that they have very high sensitivity, as long as one is careful to limit the number of ions being tapped at one time. Control of the number of ions can be accomplished by varying the time over which ions are injected into the trap. The mass resolution of ion traps is similar to that of quadrupole mass filters, although ion traps do have low m/z limitations.

Time-of-flight mass spectrometry utilizes a time-of-flight mass analyzer. For this method of m/z analysis, an ion is first given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

One consideration in this type of mass analysis is that the set of ions being studied be introduced into the analyzer at the same time. For example, this type of mass analysis is well suited to ionization techniques like MALDI which produces ions in short well-defined pulses. Another consideration is to control velocity spread produced by ions that have variations in their amounts of kinetic energy. The use of longer flight tubes, ion reflectors, or higher accelerating voltages can help minimize the effects of velocity spread. Time-of-flight mass analyzers have a high level of sensitivity and a wider m/z range than quadrupole or ion trap mass analyzers. Also data can be acquired quickly with this type of mass analyzer because no scanning of the mass analyzer is necessary.

Synthesis of Molecular Tags and Binding Compounds

The chemistry for performing the types of syntheses to form the charge-imparting moiety or mobility modifier as a peptide chain is well known in the art. See, for example, Marglin, et al., Ann. Rev. Biochem. (1970) 39:841–866. In general, such syntheses involve blocking, with an appropriate protecting group, those functional groups that are not to be involved in the reaction. The free functional groups are then reacted to form the desired linkages. The peptide can be produced on a resin as in the Merrifield synthesis (Merrifield, J. Am. Chem. Soc. (1980) 85:2149–2154 and Houghten et al., Int. J. Pep. Prot. Res. (1980) 16:311–320. The peptide is then removed from the resin according to known techniques.

A summary of the many techniques available for the synthesis of peptides may be found in J. M. Stewart, et al., "Solid Phase Peptide Synthesis, W. H. Freeman Co, San Francisco (1969); and J. Meienhofer, "Hormonal Proteins and Peptides", (1973), vol. 2, p. 46, Academic Press (New York), for solid phase peptide synthesis; and E. Schroder, et al., "The Peptides", vol. 1, Academic Press (New York), 1965 for solution synthesis.

In general, these methods comprise the sequential addition of one or more amino acids, or suitably protected amino acids, to a growing peptide chain. Normally, a suitable protecting group protects either the amino or carboxyl group of the first amino acid. The protected or derivatized amino acid can then be either attached to an inert solid support or utilized in solution by adding the next amino acid in the sequence having the complementary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide. The protecting groups are removed, as desired, according to known methods depending on the particular protecting group utilized. For example, the protecting group may be removed by reduction with hydrogen and palladium on charcoal, sodium in liquid ammonia, etc.; hydrolysis with trifluoroacetic acid, hydrofluoric acid, and the like.

For synthesis of binding compounds employing phosphoramidite, or related, chemistry many guides are available in the literature: Handbook of Molecular Probes and Research Products, 8$^{th}$ edition (Molecular Probes, Inc., Eugene, Oreg., 2002); Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Many of these chemistries allow components of the binding compound to be conveniently synthesized on an automated DNA synthesizer, e.g. an Applied Biosystems, Inc. (Foster City, Calif.) model 392 or 394 DNA/RNA Synthesizer, or the like.

Synthesis of molecular tag reagents comprising nucleotides as part of the mobility-modifying moiety can be easily and effectively achieved via assembly on a solid phase support using standard phosphoramidite chemistries. The resulting mobility modifying moiety may be linked to the label and/or polypeptide-binding moiety as discussed above.

Exemplary Synthetic Approaches for Molecular Tags

Figure 2:
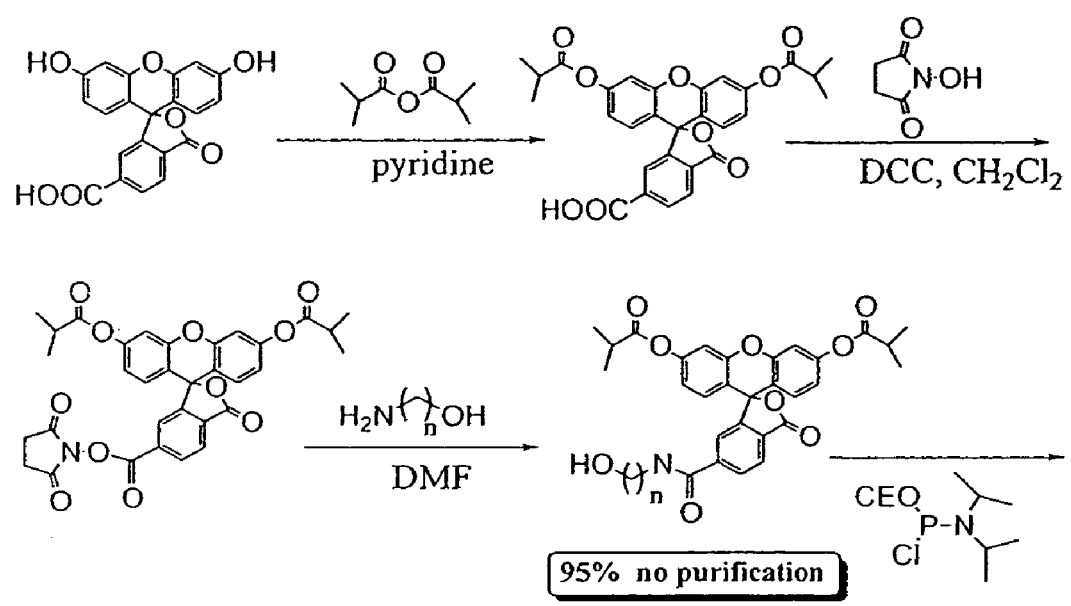
FIG. 2 illustrates one exemplary synthetic approach starting with commercially available 6-carboxy fluorescein, where the phenolic hydroxyl groups are protected using an anhydride. Upon standard extractive workup, a 95% yield of product is obtained. This material is phosphitylated to generate the phosphoramidite monomer.
Figure 3:
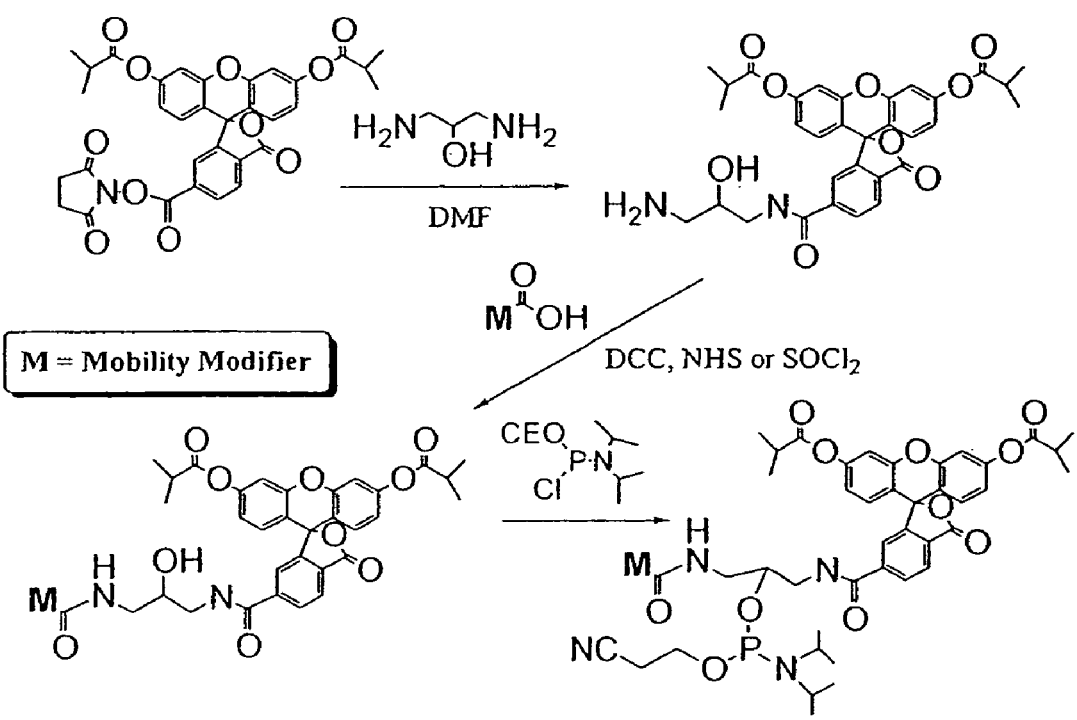
FIG. 3 illustrates the use of a symmetrical bis-amino alcohol linker as the amino alcohol with the second amine then coupled with a multitude of carboxylic acid derivatives.

One exemplary synthetic approach is outlined in FIG. 2. Starting with commercially available 6-carboxy fluorescein, the phenolic hydroxyl groups are protected using an anhydride. Isobutyric anhydride in pyridine was employed but other variants are equally suitable. It is important to note the significance of choosing an ester functionality as the protecting group. This species remains intact throughout the phosphoramidite monomer synthesis as well as during oligonucleotide construction. These groups are not removed until the synthesized oligonucleotide is deprotected using ammonia. After protection the crude material is then activated in situ via formation of an N-hydroxysuccinimide ester (NHS-ester) using DCC as a coupling agent. The DCU by product is filtered away and an amino alcohol is added. Many amino alcohols are commercially available some of which are derived from reduction of amino acids. When the amino alcohol is of the form "$H_2N-(CH_2)_n-OH$," n is in the range of from 2 to 12, and more preferably, from 2 to 6. Only the amine is reactive enough to displace N-hydroxysuccinimide. Upon standard extractive workup, a 95% yield of product is obtained. This material may be phosphitylated to generate the phosphoramidite monomer. For the synthesis of additional molecular tags, a symmetrical bis-amino alcohol linker is used as the amino alcohol (FIG. 3). As such, the second amine is then coupled with a multitude of carboxylic acid derivatives (exemplified by several possible benzoic acid derivatives shown in FIG. 4).

Figure 5:
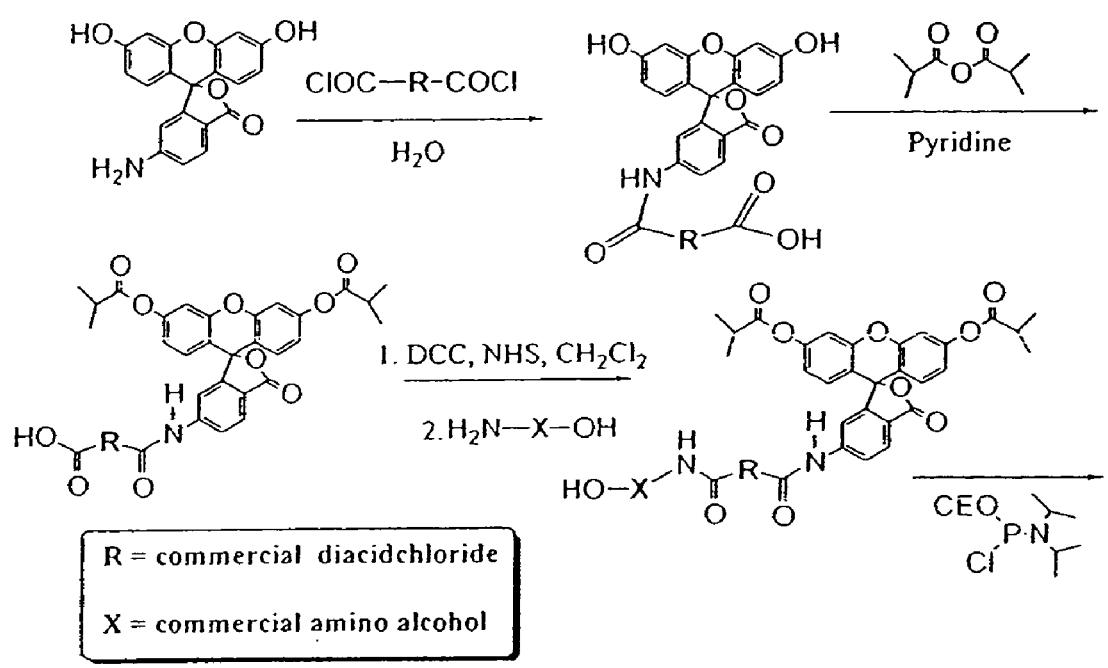
FIG. 5 illustrates the use of an alternative strategy that uses 5-aminofluorescein as starting material and the same series of steps to convert it to its protected phosphoramidite monomer.

Alternatively, molecular tags may be made by an alternative strategy that uses 5-aminofluorescein as starting material (FIG. 5). Addition of 5-aminofluorescein to a great excess of a diacid dichloride in a large volume of solvent allows for the predominant formation of the nionoacylated product over dimer formation. The phenolic groups are not reactive under these conditions. Aqueous workup converts the terminal acid chloride to a carboxylic acid. This product is analogous to 6-carboxyfluorescein, and using the same series of steps is converted to its protected phosphoramidite monomer. There are many commercially available diacid dichlorides and diacids, which can be converted to diacid dichlorides using $SOCl_2$ or acetyl chloride. There are many commercial diacid dichlorides and amino alcohols (FIG. 6). These synthetic approaches are ideally suited for combinatorial chemistry.

The molecular tag may be assembled having an appropriate functionality at one end for linking to the polypeptide-binding moieties. A variety of functionalities can be employed. Thus. the functionalities normally present in a peptide, such as carboxy, amino, hydroxy and thiol may be the targets of a reactive functionality for forming a covalent bond. The molecular tag is linked in accordance with the chemistry of the linking group and the availability of functionalities on the polypeptide-binding moiety. For example, as discussed above for antibodies, and fragments thereof such as Fab' fragments, specific for a polypeptide, a thiol group will be available for using an active olefin, e.g., maleimide, for thioether formation. Where lysines are available, one may use activated esters capable of reacting in water, such as nitrophenyl esters or pentafluorophenyl esters, or mixed anhydrides as with carbodiimide and half-ester carbonic acid. There is ample chemistry for conjugation in the literature, so that for each specific situation, there is ample precedent in the literature for the conjugation.

In an illustrative synthesis a diol is employed. Examples of such diols include an alkylene diol, polyalkylene diol, with alkylene of from 2 to 3 carbon atoms, alkylene amine or poly(alkylene amine) diol, where the alkylenes are of from 2 to 3 carbon atoms and the nitrogens are substituted, for example, with blocking groups or alkyl groups of from 1–6 carbon atoms, where one diol is blocked with a conventional protecting group, such as a dimethyltrityl group. This group can serve as the mass-modifying region and with the amino groups as the charge-modifying region as well. If desired, the mass modifier can be assembled by using building blocks that are joined through phosphoramidite chemistry. In this way the charge modifier can be interspersed between the mass modifier. For example, a series of polyethylene oxide molecules having 1, 2, 3, n units may be prepared. To introduce a number of negative charges, a small polyethylene oxide unit may be employed. The mass and charge-modifying region may be built up by having a plurality of the polyethylene oxide units joined by phosphate units. Alternatively, by employing a large spacer, fewer phosphate groups would be present, so that without large mass differences, large differences in mass-to- charge ratios may be realized.

The chemistry that is employed is the conventional chemistry used in oligonucleotide synthesis, where building blocks other than nucleotides are used, but the reaction is the conventional phosphoramidite chemistry and the blocking group is the conventional dimethoxytrityl group. Of course, other chemistries compatible with automated synthesizers can also be used. However, it is desirable to minimize the complexity of the process.

As mentioned above, in one embodiment the hub nucleus is a hydrophilic polymer, generally, an addition or condensation polymer with multiple functionality to permit the attachment of multiple moieties. One class of polymers that is useful for the reagents of the present invention comprises the polysaccharide polymers such as dextrans, sepharose, polyribose, polyxylose, and the like. For example, the hub may be dextran to which multiple molecular tags may be attached in a cleavable manner consistent with the present invention. A few of the aldehyde moieties of the dextran remain and may be used to attach the dextran molecules to amine groups on an oligonucleotide by reductive amination. In another example using dextran as the hub nucleus, the dextran may be capped with succinic anhydride and the resulting material may be linked to amine-containing oligonucleotides by means of amide formation.

Besides the nature of the linker and mobility-modifying moiety, as already indicated, diversity can be achieved by the chemical and optical characteristics of the fluoresce, the use of energy transfer complexes, variation in the chemical nature of the linker, which affects mobility, such as folding, interaction with the solvent and ions in the solvent, and the like. As already suggested, in one embodiment the linker is an oligomer, where the linker may be synthesized on a support or produced by cloning or expression in an appropriate host. Conveniently, polypeptides can be produced where there is only one cysteine or serine/threonine/tyrosine, aspartic/glutamic acid, or lysine/arginine/histidine, other than an end group, so that there is a unique functionality, which may be differentially functionalized. By using protective groups, one can distinguish a side-chain functionality from a terminal amino acid functionality. Also, by appropriate design, one may provide for preferential reaction between the same functionalities present at different sites on the linking group. Whether one uses synthesis or cloning for preparation of oligopeptides, will to a substantial degree depend on the length of the linker.

Methods of Using Compositions of the Invention

In one aspect, the invention provides a method for detecting or measuring one or more target analytes from biological sources. Conventional methodologies are employed to prepare samples for analysis. For example, for protein analytes guidance in sample preparation can be found in Scopes, Protein Purification, chapter 2 (Springer-Verlag, New York), where a range of procedures are disclosed for preparing protein extracts from different sources. Preparative techniques include mild cell lysis by osmotic disruption of cellular membranes, to enzymatic digestion of connective tissue followed by osmotic-based lysis, to mechanical homogenization, to ultrasonication.

In some embodiments, a sample containing membrane-associated analytes of interest is treated with a lipophilic sensitizer as described above to form sensitizer-treated membranes. After such preparation, a reagent containing a plurality of binding compounds are added. The amounts of binding compounds are usually determined empirically. Such components are combined under binding conditions, usually in an aqueous medium, generally at a pH in the range of about 5 to about 10, with buffer at a concentration in the range of about 10 to about 200 mM. These conditions are conventional, where conventional buffers may be used, such as phosphate, carbonate, HEPES, MOPS, Tris, borate, etc., as well as other conventional additives, such as salts, stabilizers, organic solvents, etc. The aqueous medium may be solely water or may include from 0.01 to 80 or more volume percent of a co-solvent.

The reagents are incubated for a time and at a temperature that permit a substantial number of binding events to occur. The time for incubation after combination of the reagents varies depending on the (i) nature and expected concentration of the analyte being detected, (ii) the mechanism by which the binding compounds for complexes with analytes, and (iii) the affinities of the specific reagents employed. Moderate temperatures are normally employed for the incubation and usually constant temperature. Incubation temperatures will normally range from about 5° to 99° C., usually from about 15° to 85° C., more usually 35° to 75° C.

Generally, the concentrations of the various agents involved with an assay of the invention will vary with the concentration range of the individual analytes in the samples to be analyzed, generally being in the range of about 10 nM to about 10 mM. Buffers will ordinarily be employed at a concentration in the range of about 10 to about 200 mM. The concentration of each analyte will generally be in the range of about 1 pM to about 100 µM, more usually in the range of about 100 pM to about 10 µM. In specific situations the concentrations may be higher or lower, depending on the nature of the analyte, the affinity of the binding compounds, the efficiency of release of the molecular tags, the sensitivity with which the molecular tags are detected, and the number of analytes to be determined in the assay, as well as other considerations.

In some embodiments, where components of the assay mixture interfere with a chromatographic analysis, the molecular tags may be required to be separated from the assay mixture prior to chromatographic analysis, or certain components of the assay mixture, e.g. binding moieties with unreleased molecular tags, may be required to be excluded from the chromatographic analysis. Depending on the nature of the molecular tags and the components of the assay mixture, one may sequester or adsorb or exclude such binding moieties by using guard column, and the like. Alternatively, one may have a capture ligand attached to binding compounds for the purpose of removing such interfering components in the mixture.

An additional degree of flexibility can be conferred on an assay by the stage at which the molecular tags are labeled. A molecular tag may contain a functionality allowing it to bind to a label after reaction with the sample is complete. In this embodiment, a molecular tag comprising a functionality for binding to a detectable label is combined with a sample. After a binding reaction takes place and molecular tags are released, additional reagents are combined in a sample vessel with the products of the first reaction, which react with the released molecular tags to add a detectable label.

For quantitation, one may choose to use controls, which provide a signal in relation to the amount of the target that is present or is introduced. A control to allow conversion of relative fluorescent signals into absolute quantities is accomplished by addition of a known quantity of a fluorophore to each sample before separation of the molecular tags. Any fluorophore that does not interfere with detection of the molecular tag signals can be used for normalizing the fluorescent signal. Such standards preferably have separation properties that are different from those of any of the molecular tags in the sample, and could have the same or a different emission wavelength. Exemplary fluorescent molecules for standards include ROX, FAM, and fluorescein and derivatives thereof.

Identification of Orphan Secreted Proteins

Orphan secreted protein candidates can be identified in gene sequence databases in public domain or private sector based on the following criteria:

(1) The presence of predicted signal peptide sequence of 22 amino acids in average at the amino-terminus containing a positively charged n-region, followed by a hydrophobic h-region and a neutral but polar c-region and the absence of predicted alpha-helical transmembrane domain sequence of 20–30 hydrophobic amino acids closely followed by a few charged amino acids anywhere else in the open reading frame of the gene, conforming to the prediction of secreted proteins.

(2) The presence of conserved proteolytic cleavage sites in the upstream region proximal to the predicted transmembrane domain which can potentially lead to the release of soluble receptors from the cell surface under physiologic conditions;

(3) The presence of predicted splice junction sites in the gene sequence resulting in splice variants of mRNAs that possess the above criteria.

The genetic materials of putative orphan soluble ligands in the form of mRNA, cDNA, or cloning vector containing the gene insert can be converted into polypeptides by in vitro coupled transcription and translation or by in vivo recombinant expression in prokaryotic, e.g., bacteria, or eukaryotic, e.g., yeast, mammalian cell lines host cells when the gene insert is placed under the control of an appropriate promoter. Methods for obtaining nucleic acid material for use in vitro or in vivo recombinant production of secreted proteins will now be discussed.

The present invention may utilize methods and reagents for isolating a gene encoding a protein having a signal peptide, by isolating an RNA molecule from microsomes or other endoplasmic reticulum (ER) preparation. In a preferred embodiment, the protein having a signal peptide is a secreted protein. The protein can also be an integral, ER, Golgi, plasma-membrane protein, a glycoprotein, or a lysosome protein. In another embodiment, a population of RNA molecules is isolated from microsomes and used to prepare a library of nucleic acids encoding proteins having a signal peptide. In a preferred method, the library is a cDNA library, where individual members of the library are cDNAs encoding secreted proteins.

In another method, the RNA molecule or the population of RNA molecules isolated from microsomes and the microsomes are heterologous, i.e., originate from different sources. For example, a population of RNA molecules being translated can first be contacted with heterologous microsomes and one or more RNA molecule associating with the microsomes can be isolated. In one embodiment, the RNA is first incubated with an in vitro transcription system and then microsomes are added to the in vitro transcription reactions. Alternatively, the RNA is added to a mixture containing an in vitro translation system and microsomes.

The RNA can also be extracted from a specific cellular compartment, e.g., nucleus or the cytoplasm. In such methods, the nucleus is either isolated for purification of RNA therefrom, or the nucleus is discarded for purification of cytoplasmic RNA. Further details regarding these and other RNA extraction protocols are set forth, e.g., in Molecular Cloning A Laboratory Manual, $2^{nd}$ Ed., ed. By Sambrook, Fritsch and Maniatis (Cold Spring Harbor Laboratory Press: 1989).

The protein probes in this aspect of the invention are formed by linking a secreted protein $P_i$ to a distinctive molecular tag through a cleavable linker.

To facilitate extraction or purification of an expressed protein from an expression system, a gene sequence encoding a defined affinity peptide tag (e.g. 6×His, HA, myc, etc.) can also be inserted to the amino or carboxy-terminus of the orphan-protein gene sequence. While captured on immobilized affinity reagent (e.g. immobilized Nickel ions, antibodies), chemical conjugation of the expressed polypeptide to molecular tag can take place via primary amino groups (e.g. on lysines) following addition of NHS-molecular tag conjugate under appropriate buffer conditions. The chemical conjugation can be conducted under non-reducing conditions that favor a low NHS-molecular tag to protein ratio such that the receptor binding activity of the expressed protein is preserved. Following affinity binding and chemical conjugation, the polypeptide-molecular tag conjugate can be eluted from the immobilized affinity binding reagent.

In a preferred approach, where site-specific conjugation of the expressed polypeptide with a molecular tag is enabled, gene codons for amino acids with reactive side chains (e.g. amino group on lysine, thiol group on cysteine) can be inserted terminal to the gene sequence encoding the affinity peptide tag. These amino acids inserted next to the affinity tag provide preferred reactive groups for chemical conjugation of the molecular tag as opposed to the reactive groups in other parts of the expressed polypeptide due to proximity effect following the binding of the expressed polypeptide to the affinity reagents. Alternatively, site-specific conjugation can occur at the lysines within the n-region of the signal peptide. The reactive derivatives (e.g. NHS, maleimide) of molecular tag can be co-immobilized with the affinity reagents to achieve the close juxtaposition. Or preferably the reactive derivatives of molecular tag can be directly linked to the affinity reagent so that conjugation of the molecular tag to the reactive amino acid can occur in solution without co-immobilization on solid phase. Certain orphan secreted or soluble ligands are short peptides. They are usually generated upon proteolytic cleavage of a pro-polypeptide by itself or by another enzyme following physiologic interaction. Many of the sites of such cleavage are conserved and predictable from the gene sequence, particularly based on known cleavage pattern of members from the same gene family. From non-mammalian sources, orphan secreted ligands (e.g., conopeptides from marine cone snails) that exhibit biologic activity or cellular toxicity towards human cells following binding to specific cell surface receptors represent targets for receptor screening and their amino acid sequences have been determined biochemically. Short orphan peptide ligand can be prepared synthetically and a unique molecular tag, either as single molecule (peptide-linker-cleavable linker-molecular tag)or in a chemical cluster on a polymeric scaffold, can be attached to the peptide via a linker (e.g. polyethylene glycol). The synthetic peptide-molecular tag conjugate can then be used directly in ligand-receptor interaction assay.

FIGS. 11A–11C illustrate one method for coupling molecular tag precursor 74 (a portion shown as "e-Tag") to a secreted protein 72 synthesized to have an N-terminal extension terminated at a cysteine amino acid. The protein is reacted with molecular tag precursor 74 having the linker shown containing a terminal Br group, which is the target for nucleophilic displacement by the sulfur group in the protein. The protein and molecular tag precursor are reacted under standard conditions for a nucleophilic displacement reaction, coupling the molecular tag to the N-terminal cysteine of the protein, producing protein probe 76, shown in FIG. 11B. This reaction can be carried out in crude protein preparation for example from cell supernatants or cell lysates. In the probe cleaving reaction, cleavage of the sulfur-containing linker in the presence of singlet oxygen, results in a released molecular tag 80, and a modified protein 78 having a $SO_2H$ at the N terminal group.

FIGS. 12A–12C illustrate a second exemplary method for coupling molecular tag, indicated by a common backbone structure 82, to a secreted protein 84 having an N-terminal sulfhydryl group. The reaction involves a nucleophilic addition reaction, to produce the protein probe shown at 86 in FIG. 12B. Three molecular tag-linker structures contemplated in this method are shown at (1)–(3) in FIG. 12C, where R is the protein moiety of the probe in each structure. This reaction can be carried out in crude protein preparation for example from cell supernatants or cell lysates. In the probe cleaving reaction, cleavage of the sulfur-containing linker in the presence of singlet oxygen, results in a released molecular tag 88, and a modified protein 90 having a $SO_2H$ at the N terminal group, as in FIG. 12C.

FIGS. 12A–12C illustrate a second exemplary method for coupling molecular tag, indicated by a common backbone structure 82, to a secreted protein 84 having an N-terminal sulflhydryl group. The reaction involves a nucleophilic addition reaction, to produce the protein probe shown at 86 in FIG. 12B, carried out under reaction conditions well known for nucleophilic addition reactions. Three molecular tag-linker structures contemplated in this method are shown at (1)–(3) in FIG. 12D, where R is the protein moiety of the probe in each structure. This reaction can be carried out in crude protein preparation for example from cell supernatants or cell lysates. In the probe cleaving reaction, cleavage of the sulfur-containing linker in the presence of singlet oxygen, results in a released molecular tag 88, and a modified protein 90 having a $SO_2H$ at the N terminal group, as in FIG. 12C.

Figure 13A:
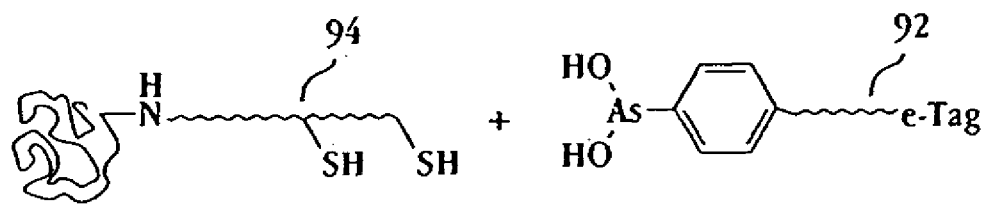
FIGS. 13A–13C illustrate a third method of forming protein probes for use in the assay of the invention, and the probe cleavage reaction in the presence of singlet oxygen.
Figure 13B:
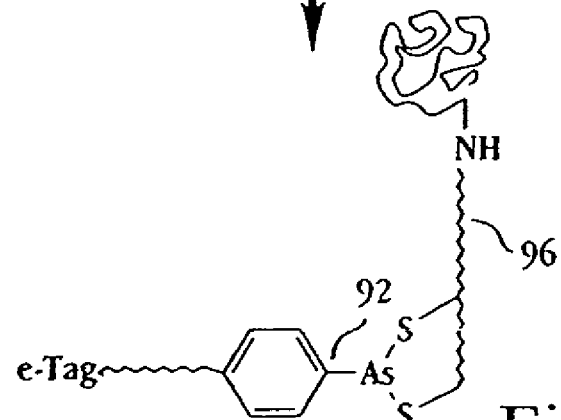
Figure 13C:
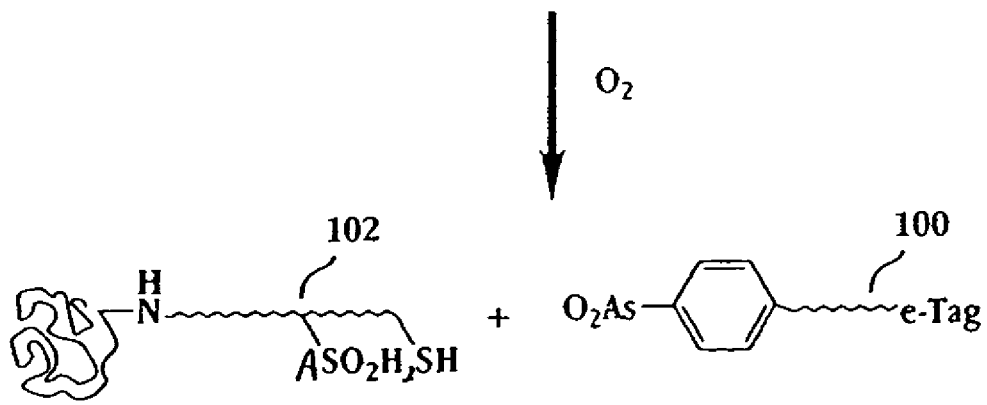

FIGS. 13A–13C illustrate a third exemplary method for coupling molecular tag 92 to a secreted protein 94 having a pair of N-terminal sulflhydryl group, i.e., cysteine amino acids, which are separated by 1–2 amino acids. The reaction involves a bi-displacement reaction to form a cyclic coupled protein probe 96 as shown in FIG. 13B, carried out under conditions well known for bi-displacement reactions. This reaction can be carried out in crude protein preparation for example from cell supernatants or cell lysates. In the probe cleaving reaction, cleavage of the sulfur-containing linker in the presence of singlet oxygen, results in a released molecular tag 100, and a modified protein 102 having a $SO_2H$ at the N terminal group, as seen in FIG. 13C.

Figure 14A:
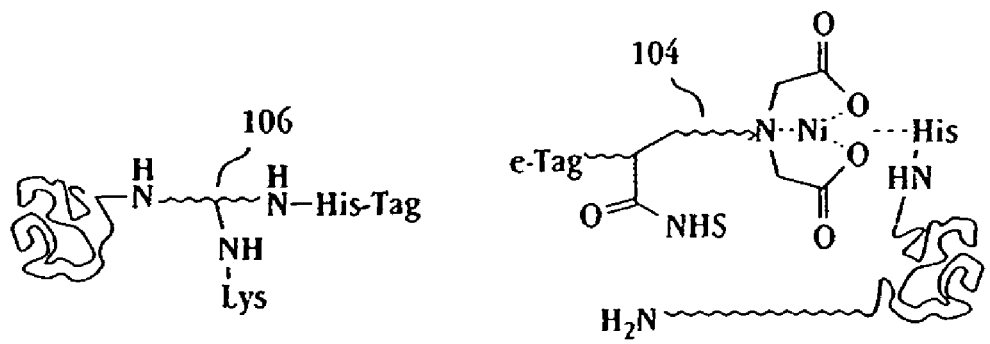
FIGS. 14A and 14B illustrate a fourth method of forming protein probes for use in the assay of the invention (14A) and various molecular tag structures suitable for use in the reaction (14B).
Figure 14B:
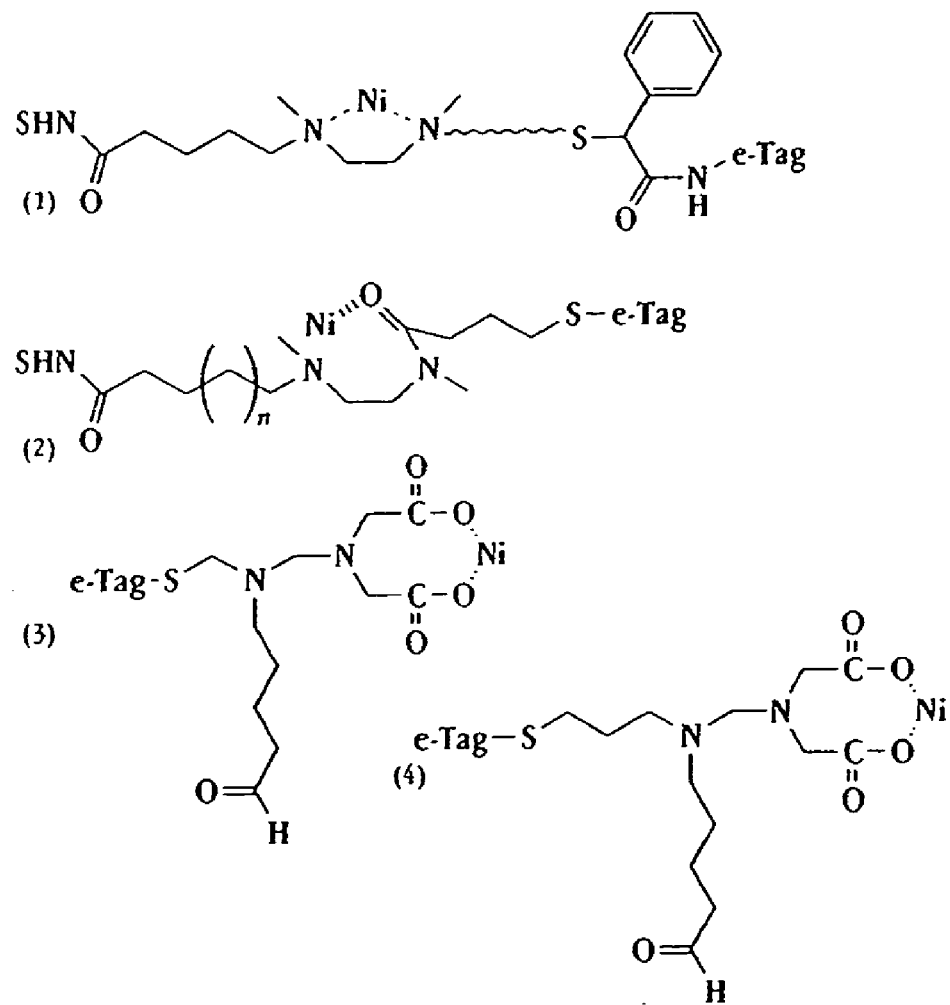

FIGS. 14A and 14B illustrate a fourth exemplary method for coupling molecular tag 104 to a secreted protein 106 having a terminal His tag and a Lys amino acid residue near (within 1–2 amino acid residues) the terminal His. The molecular tag is part of a Ni coordination compound that reacts with the protein in the manner shown in FIG. 14A, to place the intermediate Lys amino group near the terminal end of the protein adjacent a N hydroxy succinamide (NHS) group (compounds (1) and (2) in FIG. 14B), or an aldehyde group (compounds (3) and (4) in FIG. 14B) in the molecular tag. For compounds, (1) and (2) in FIG. 14B, the coupling occurs by NHS reaction with the positioned Lys amine group. For compounds (3) and (4), the reaction occurs by reductive animation, again, under standard conditions. These reaction can be carried out in crude protein preparation for example from cell supernatants or cell lysates.

These methods may be used to construct individual probes, or sets of probes as described above. One set of probes, for inclusion in a kit assaying receptor-specific binding of each and any of a plurality of cell-secreted proteins to receptors carried on the surfaces of one or cells or cell types, has the form $P_N$-(L-$E_N$), where $P_N$ is one of N cell-secreted proteins of interest, L is a linker cleavable under selected reaction conditions, and $E_N$ is a molecular tag associated with $P_N$.

The cells employed with the protein probes described above can be single cell types, e.g., cultured cell lines, or groups of different types of cells, e.g., cells obtained from a given tissue or organ. The cells will typically have the same mammalian origin as the secreted protein, e.g., human cells for assay of human secreted proteins. The cell(s) may also be selected according to the suspected nature of the orphan protein. In particular, it may be useful in examining or confirming the nature of the orphan enzyme, to employ a cell that shows a detectable response to ligand-receptor binding.

For example, to assay an orphan secreted protein for activity as a cytokine, other immune stimulating or inhibitory protein, the cell employed may be spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human Interferon gamma, Schreiber, R. D. In Current Protocols in Immunology. J. E. e.a. Coligan eds. Vol 1 pp. 681–688, John Wiley and Sons, Toronto, 1994. Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Green Publishing Associates and Wiley-Interscience (Chapter 3, In vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137: 3494–3500, 1986; Takai et al., J. Inmunol. 140:508–512, 1988; Herrmann et al., Proc. Natl. Acad. Sci. USA 78:2488–2492, 1981; Herrmann et al., J. Immunol. 128: 1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512. 1988; Bertagnolli et al., Cellular Immunology 133:327–341, 1991; Brown et al., J. Immunol. 153:3079–3092, 1994.

Other assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:

149–160 1989; Stoltenborg et al., J. Immunol. Methods 175:59–68, 1994; Stitt et al., Cell 80:661–670, 1995.

As is clear from the art described above, a number of different functional assays are carried out on a number of different cell types to determine the function of the orphan secreted protein. It is much more preferable to perform a single assay on different cell types to identify the cell surface receptor. Once a cell type or group of cells has been identified for the assay, the cells are preferably modified to have surface-attached cleaving agents, e.g., a sensitizer of the type described above.

Figure 15:
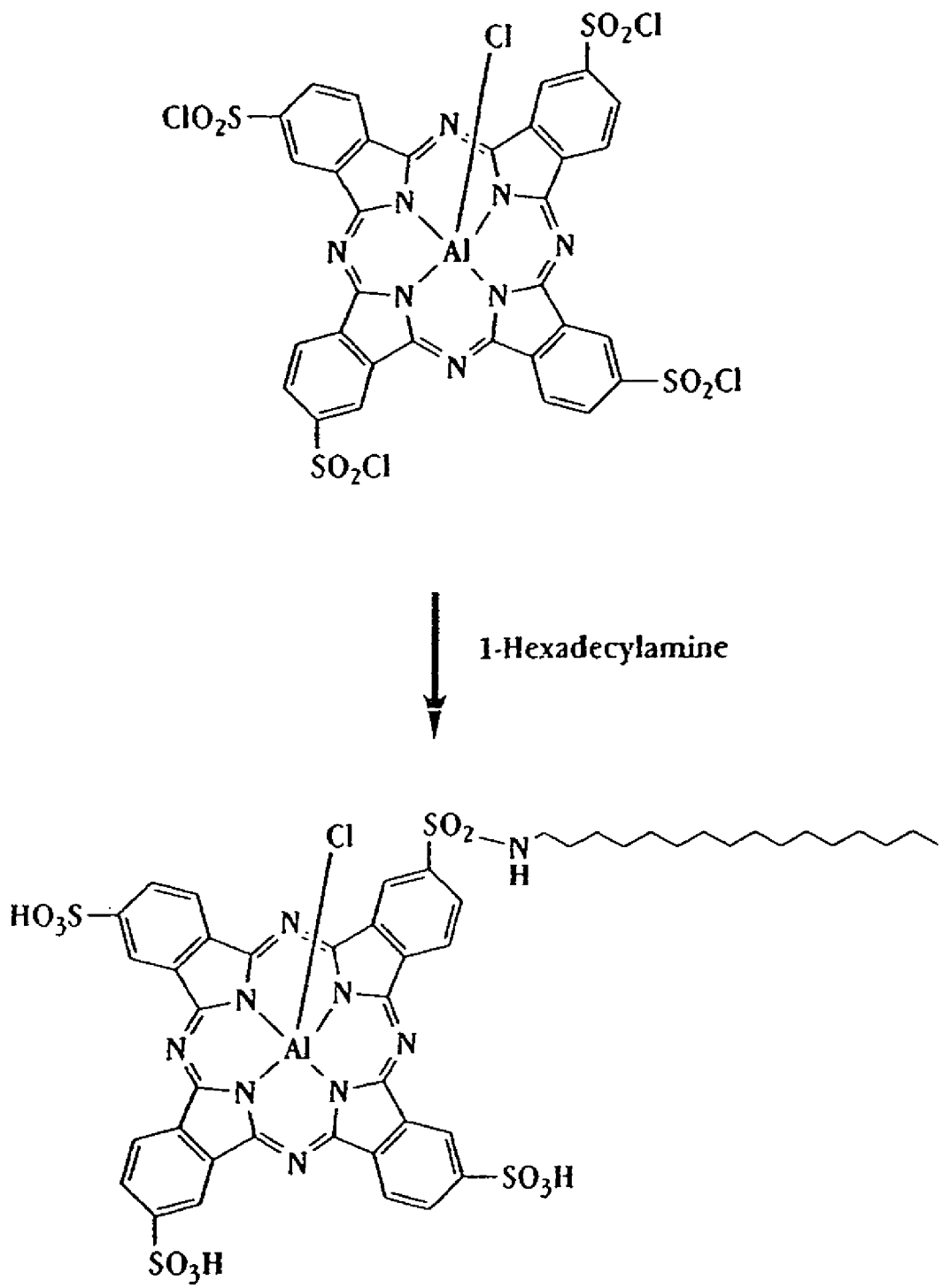
FIG. 15 illustrates the synthesis of a sensitizer-fatty acyl chain conjugate useful for anchoring the sensitizer to a cell-surface membrane.

In one general embodiment, the sensitizer is attached to a lipid-anchor moiety, such as a long-chain alkyl structure, fatty acid, mono-, di- or tri-glyceride, phospholipid, or sterol, that is compatible with a lipid bilayer membrane structure, and has a large partition coefficient for such structures. FIG. 15 illustrates a simple chemical coupling method for attaching one or more long chain fatty alkylyl groups to a phthalocyanine sensitizer group. The number of alkylchains attached to each sensitizer can be adjusted by the stoichiometric ratio of reactants. Methods for coupling compounds to phospholipid head groups or to amino, or to reactive groups in sterols and other lipids is well known.

Once formed, the derivatized sensitizer is added to the cells, e.g., in micellar or liposomal form, and allow to diffuse or equilibrate into the cell membranes under conventional conditions, e.g., physiological salt and pH, 37° C., for a period of 30 minutes to several hours. In another general method, a biotin labeled phospholipid (Molecular Probe) is incorporated into cell membrane, followed by addition of strepavidin sensitizer molecule. The sensitizer molecule can be covalently attached to strepavidin or a biotin labeled sensitizer molecule is first added to strepavidin (1:1 ratio) followed by labeling of cell membrane.

GCPR Pathway Assays

G-protein coupled receptors (GPCRs) represent one of the most important families of drug targets. G protein-mediated signaling systems have been identified in many divergent organisms, such as mammals and yeast. GPCRs respond to, among other extracellular signals, neurotransmitters, hormones, odorants and light. GPCRs are thought to represent a large superfamily of proteins that are characterized by the seven distinct hydrophobic regions, each about 20–30 amino acids in length, that forms the transmembrane domain. The amino acid sequence is not conserved across the entire superfamily, but each phylogenetically related subfamily contains a number of highly conserved amino acid motifs that can be used to identify and classify new members. Individual GPCRs activate particular signal transduction pathways, although at least ten different signal transduction pathways are known to be activated via GPCRs. For example, the beta 2-adrenergic receptor (βAR) is a prototype mammalian GPCR. In response to agonist binding, βAR receptors activate a G protein ($G_s$) which in turn stimulates adenylate cyclase and cyclic adenosine monophosphate production in the cell.

It has been postulated that members of the GPCR superfamily desensitize via a common mechanism involving G protein-coupled receptor kinase (GRK) phosphorylation followed by arrestin binding. The protein β-arrestin regulates GPCR signal transduction by binding agonist-activated receptors that have been phosphorylated by G protein receptor kinases. The β-arrestin protein remains bound to the GPCR during receptor internalization. The interaction between a GPCR and α-arrestin can be measured using several methods. In one example, the β-arrestin protein is fused to green fluorescent protein to create a protein fusion (Barak et al. (1997) J. Biol. Chem. 272(44):27497–500). The agonist-dependent binding of β-arrestin to a GPCR can be visualized by fluorescence microscopy. Microscopy can also be used to visualize the subsequent trafficking of the GPCR β-arrestin complex to clathrin coated pits. Other methods for measuring binding of β-arrestin to a GPCR in live cells include techniques such as FRET (fluorescence resonance energy transfer), BRET (bioluminescent energy transfer) or enzyme complementation (Rossi et al. (1997) Proc. Natl. Acad. Sci. USA 94(16):8405–10).

At present, there are nearly 400 GPCRs whose natural ligands and function are known. These known GPCRs, named for their endogenous ligands, have been classified into five major categories: Class-A Rhodopsin-like; Class-B Secretin-like; Class-C Metabotropic glutamate/pheromone; Class-D Fungal pheromone; Class-E cAMP (dictyostelium). Representative members of Class-A are the amine receptors (e.g., muscarinic, nicotinic, adrenergic, adenosine, dopamine, histamine and serotonin), the peptide receptors (e.g., angiotensin, bradykinin, chemokines, endothelin and opioid), the hormone receptors (e.g., follicle stimulating, lutropin and thyrotropin), and the sensory receptors, including rhodopsin (light), olfactory (smell) and gustatory (taste) receptors. Representatives of Class-B include secretin, calcitonin, gastrin and glucagon receptors.

Many available therapeutic drugs in use today target GPCRs, as they mediate vital physiological responses, including vasodilation, heart rate, bronchodilation, endocrine secretion, and gut peristalsis (Wilson and Bergsma (2000) Pharm. News 7: 105–114). For example, ligands to β-adrenergic receptors are used in the treatment of anaphylaxis, shock, hypertension, hypotension, asthma and other conditions. Additionally, diseases can be caused by the occurrence of spontaneous activation of GPCRs, where a GPCR cellular response is generated in the absence of a ligand. Drugs that are antagonists of GPCRs decrease this spontaneous activity (a process known as inverse agonist) are important therapeutic agents.

Due to the therapeutic importance of GPCRs, methods for the rapid screening of compounds for GPCR ligand activity are desirable. The present invention provides a method of screening test compounds and test conditions for the ability to modulate (activate or inhibit, enhance or depress) a GPCR pathway, and provides methods of assessing GPCR pathway function, such as the function of an orphan GPCR, in a cell in general. In another aspect of the present method, lipophilic photosensitizers are attached to the cellular membranes. A candidate ligand or a library of candidate ligands can be attached to a molecular tag, after which the ligand is allowed to bind to the receptor. After excitation of the photosensitizer with a light source, the cleavable linker is cleaved releasing the molecular tag. The released molecular tag can be detected in the extracellular fluid, as detailed above, which provides information on the structure of the ligand for the GPCR.

In one aspect, the present invention provides methods for screening modulators of GPCR activity comprising: a) providing a cell expressing a known or unknown GPCR, wherein the cell is labeled with a lipophilic photosensitizer, b) exposing the cell to a test compound conjugated by a cleavable linkage to a molecular tag; c) illuminating the photosensitizer to generate singlet oxygen that cleaves the molecular tag, d) detecting the signal from the released molecular tag, and (d) comparing the signal produced in the presence of the test compound with the signal produced in the absence, wherein changes in the signal indicates that the compound is a modulator of a GPCR.

The present invention thus provides a convenient method of identifying modulators for an orphan GPCR. Orphan GPCRs are novel receptors typically identified by sequence comparison-based methods, but whose cognate ligands are not known. It is estimated that from 400 to as many as 5000 orphan GPCRs may be coded for in the human genome, representing a vast potential for developing new drugs.

Preparation of Cells that Express GPCRs

Methods for preparing cells that express GPCRs have been described. See, e.g., U.S. Pat. Nos. 6,051,386, 6,069,296, 6,111,076 and 6,280,934. Generally, complementary DNA encoding GPCRs can be obtained and can be expressed in an appropriate cell host using techniques well known in the art. Typically, once a full-length GPCR cDNA has been obtained, it can be expressed in a mammalian cell line, yeast cell, amphibian cell or insect cell for functional analysis. Preferably, the cell line is a mammalian cell line that has been characterized for GPCR expression and that optionally contains a wide repertoire of G-proteins to allow functional coupling to downstream effectors. Examples of such cell lines include Chinese Hamster Ovary (CHO) or Human Embryonic Kidney 293 (HEK293) lines. Cells in which the cDNA is expressed can be encoded using the methods disclosed herein, thus allowing the multiplex screening of ligands. The expressed receptor can then be screened in a variety of functional assays to identify an activating ligand as disclosed above.

EXAMPLES

The invention is demonstrated further by the following syntheses and illustrative examples. Parts and percentages are by weight unless otherwise indicated. Temperatures are in degrees Centigrade (° C.) unless otherwise specified. The following preparations and examples illustrate the invention but are not intended to limit its scope. Unless otherwise indicated, peptides used in the following examples were prepared by synthesis using an automated synthesizer and were purified by gel electrophoresis or HPLC.

The following abbreviations have the meanings set forth below:
Tris HCl—Tris(hydroxymethyl)aminomethane-HCl (a 10× solution) from BioWhittaker, Walkersville, Md.
TLC—thin layer chromatography
BSA—bovine serum albumin, e.g. available from Sigma Chemical Company (St. Louis, Mo.), or like reagent supplier.
EDTA—ethylene diamine tetra-acetate from Sigma Chemical Company
FAM—carboxyfluorescein
EMCS—N-ε-maleimidocaproyloxy-succinimide ester
EDC—1-Ethyl-3-(3-dimethylaminopropyl)carbodiimide
NHS—N-hydroxysuccinimide
DCC—1,3-dicylcohexylcarbodiimide
DMF—dimethylformamide
Fmoc—N-(9-fluorenylmethoxycarbonyl)-

Example 1

Conjugation and Release of a Molecular Tag

FIG. 7A–B summarize the methodology for conjugation of molecular tag precursor to an antibody or other binding compound with a free amino group, and the reaction of the resulting conjugate with singlet oxygen to produce a sulfinic acid moiety as the released molecular tag. FIG. 8A–J shows several molecular tag reagents, most of which utilize 5- or 6-carboxyfluorescein (FAM) as starting material.

Example 2

Preparation of Pro2, Pro4, and Pro6 through Pro 13

Figure 9A:
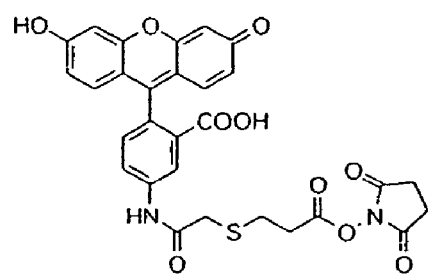
FIGS. 9A–J show the structures of e-tag moieties that have been designed and synthesized. (Pro1 is commercially available from Molecular Probes, Inc.)
Figure 9A:
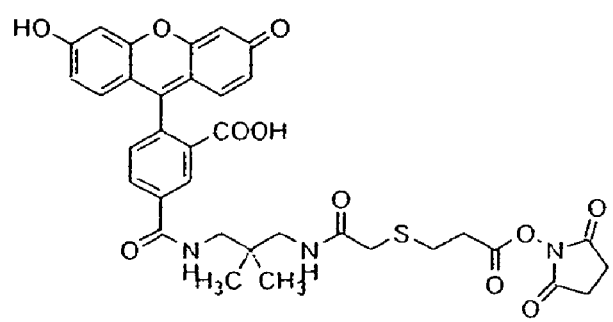
Figure 9A:
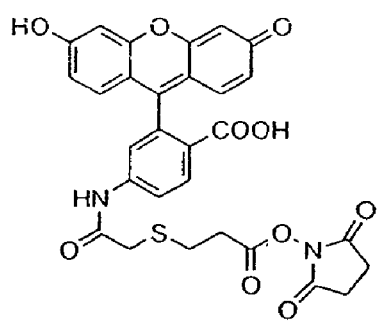
Figure 9A:
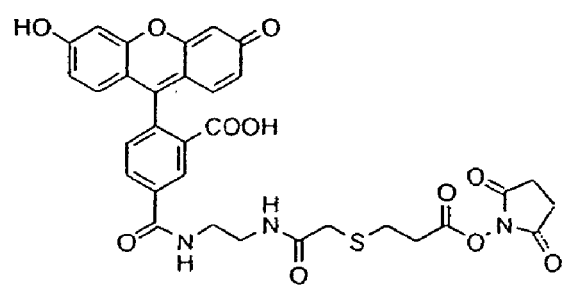

The scheme outlined in FIG. 9A shows a five-step procedure for the preparation of the carboxyfluorescein-derived molecular tag precursors, namely, Pro2, Pro4, Pro6, Pro7, Pro8, Pro9, Pro10, Pro11, Pro12, and Pro13. The first step involves the reaction of a 5- or 6-FAM with N-hydroxysuccinimide (NHS) and 1,3-dicylcohexylcarbodiimide (DCC) in DMF to give the corresponding ester, which was then treated with a variety of diamines to yield the desired amide, compound 1. Treatment of compound 1 with N-succinimidyl iodoacetate provided the expected iodoacetamide derivative, which was not isolated but was further reacted with 3-mercaptopropionic acid in the presence of triethylamine. Finally, the resulting β-thioacid (compound 2) was converted, as described above, to its NHS ester. The various e-tag moieties were synthesized starting with 5- or 6-FAM, and one of various diamines. The diamine is given $H_2N^\frown X^\frown NH_2$ in the first reaction of FIG. 9A. The regioisomer of FAM and the chemical entity of "X" within the diamine are indicated in the table below for each of the molecular tag precursors synthesized. Clearly, the diamine, X, can have a wide range of additional forms, as described above in the discussion of the mobility modifier moiety.

| Precursor | FAM | X |
|---|---|---|
| Pro2 | 5-FAM | $C(CH_3)_2$ |
| Pro4 | 5-FAM | no carbon |
| Pro6 | 5-FAM | $(CH_2)_8$ |
| Pro7 | 5-FAM | $CH_2OCH_2CH_2OCH_2$ |
| Pro8 | 5-FAM | $CH_2CH_2OCH_2CH_2OCH_2CH_2OCH_2CH_2$ |
| Pro9 | 5-FAM | 1,4-phenyl |
| Pro10 | 6-FAM | $C(CH_3)_2$ |
| Pro11 | 6-FAM | no carbon |
| Pro12 | 6-FAM | $CH_2OCH_2CH_2OCH_2$ |
| Pro13 | 6-FAM | $CH_2CH_2OCH_2CH_2OCH_2CH_2OCH_2CH_2$ |

Synthesis of Compound 1

To a stirred solution of 5- or 6-carboxyfluorescein (0.5 mmol) in dry DMF (5 mL) were added N-hydroxysuccinimide (1.1 equiv.) and 1,3-dicylcohexylcarbodiimide (1.1 equiv.). After about 10 minutes, a white solid (dicyclohexylurea) started forming. The reaction mixture was stirred under nitrogen at room temperature overnight. TLC (9:1 $CH_2Cl_2$-MeOH) indicated complete disappearance of the starting material.

The supernatant from the above mixture was added dropwise to a stirred solution of diamine (2–5 equiv.) in DMF (10 mL). As evident from TLC (40:9:1 $CH_2Cl_2$-MeOH—$H_2O$), the reaction was complete instantaneously. The solvent was removed under reduced pressure. Flash chromatography of the resulting residue on iatrobeads silica provided the desired amine (compound 1) in 58–89% yield. The $^1H$ NMR (300 MHz, DMSO-$d_6$) of compound 1 was in agreement with the assigned structure.

Synthesis of Compound 2

To the amine (compound 1) (0.3 mmol) were sequentially added dry DMF (10 mL) and N-succinimidyl iodoacetate (1.1 equiv.). The resulting mixture was stirred at room temperature until a clear solution was obtained. TLC (40:9:1 $CH_2Cl_2$-MeOH—$H_2O$) revealed completion of the reaction.

The above reaction solution was then treated with triethylamine (1.2 equiv.) and 3-mercaptopropionic acid (3.2 equiv.). The mixture was stirred at room temperature overnight. Removal of the solvent under reduced pressure followed by flash chromatography afforded the β-thioacid (compound 2) in 62–91% yield. The structure of compound 2 was assigned on the basis of its $^1$NMR (300 MHz, DMSO-$d_6$).

Synthesis of Pro2, Pro4, and Pro6 Through Pro13

To a stirred solution of the β-thioacid (compound 2) (0.05 mmol) in dry DMF (2 mL) were added N-hydroxysuccinimide (1.5 equiv.) and 1,3-dicylcohexylcarbodiiuide (1.5 equiv.). The mixture was stirred at room temperature under nitrogen for 24–48 h (until all of the starting material had reacted). The reaction mixture was concentrated under reduced pressure and then purified by flash chromatography to give the target molecule in 41–92% yield.

Preparation of Pro1

Figure 9B:
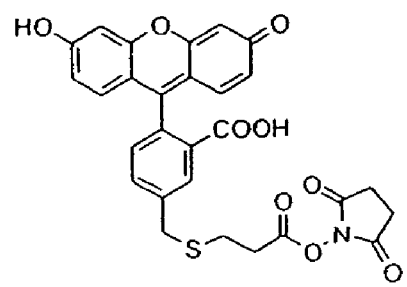
Figure 9B:
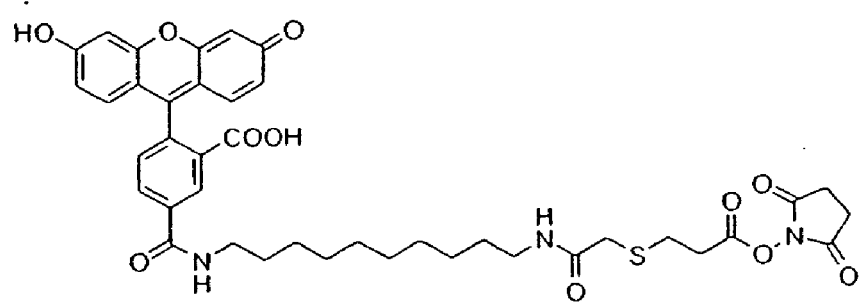
Figure 9B:
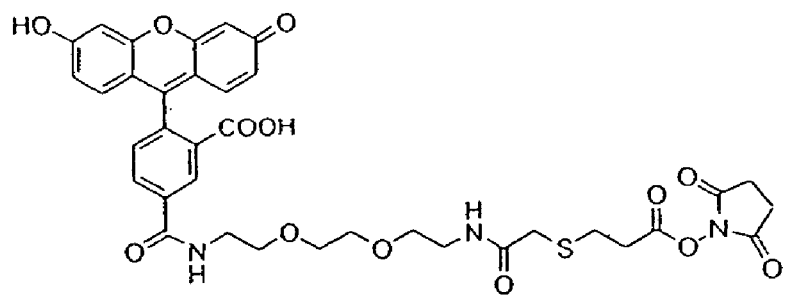
Figure 9B:
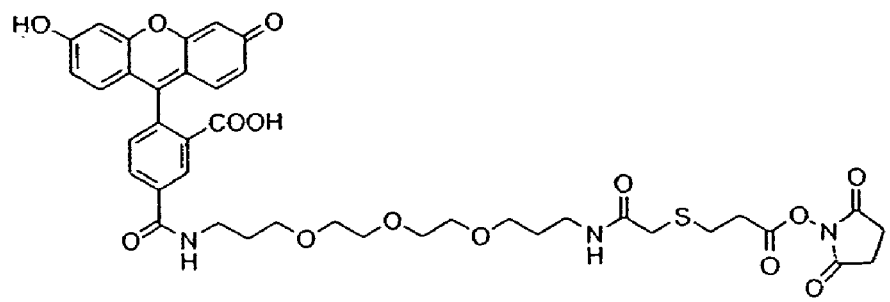

The compounds of this reaction are shown in FIG. 9B. To a stirred solution of 5-iodoacetamidofluorescein (compound 4) (24 mg, 0.047 mmol) in dry DMF (2 mL) were added triethylamine (8 μL, 0.057 mmol) and 3-mercaptopropionic acid (5 μL, 0.057 mmol). The resulting solution was stirred at room temperature for 1.5 h. TLC (40:9:1 $CH_2Cl_2$-MeOH—$H_2O$) indicated completion of the reaction. Subsequently, N-hydroxysuccinimide (9 mg, 0.078 mmol) and 1,3-dicylcohexylcarbodiimide (18 mg, 0.087 mmol) were added. The reaction mixture was stirred at room temperature under nitrogen for 19 h at which time TLC showed complete disappearance of the starting material. Removal of the solvent under reduced pressure and subsequent flash chromatography using 25:1 and 15:1 $CH_2Cl_2$-MeOH as eluant afforded Pro1 (23 mg, 83%).

Preparation of Pro3

Figure 9C:
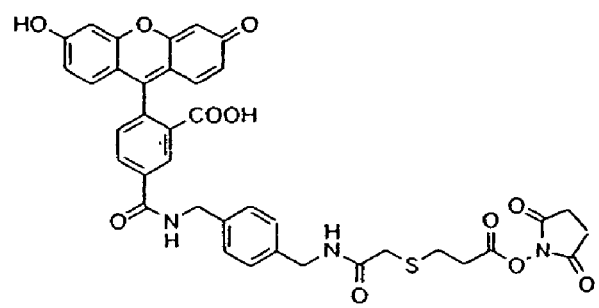
Figure 9C:
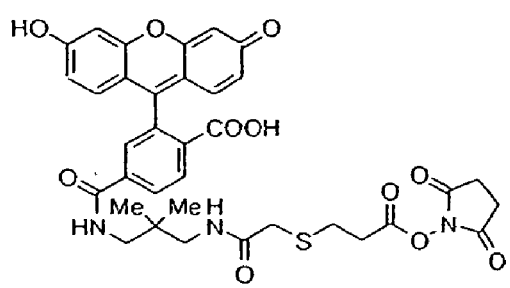
Figure 9C:
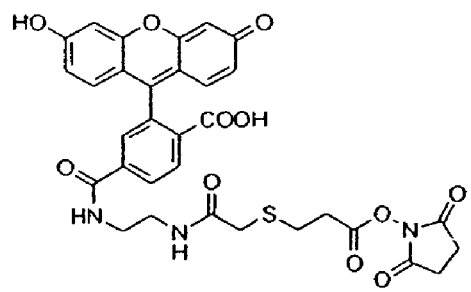
Figure 9C:
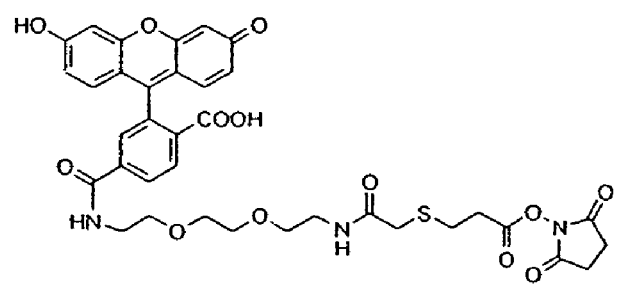

The compounds of this reaction are shown in FIG. 9C. To a stirred solution of 6-iodoacetamidofluorescein (compound 5) (26 mg, 0.050 mmol) in dry DMF (2 mL) were added triethylamine (8 μL, 0.057 mmol) and 3-mercaptopropionic acid (5 μL, 0.057 mmol). The resulting solution was stirred at room temperature for 1.5 h. TLC (40:9:1 $CH_2Cl_2$-MeOH—$H_2O$) indicated completion of the reaction. Subsequently, N-hydroxysuccinimide (11 mg, 0.096 mmol) and 1,3-dicylcohexylcarbodiimide (18 mg, 0.087 mmol) were added. The reaction mixture was stirred at room temperature under nitrogen for 19 h at which time TLC showed complete disappearance of the starting material. Removal of the solvent under reduced pressure and subsequent flash chromatography using 30:1 and 20:1 $CH_2Cl_2$-MeOH as eluant provided Pro3 (18 mg, 61%).

Preparation of Pro5

Figure 9D:
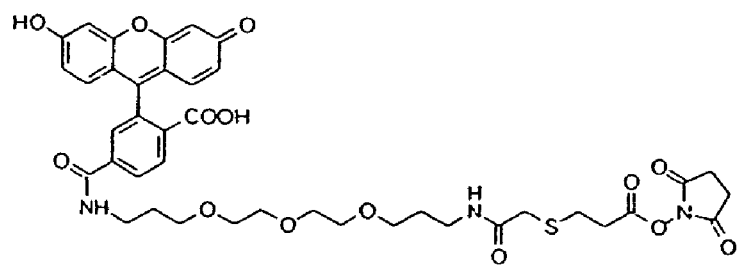
Figure 9D:
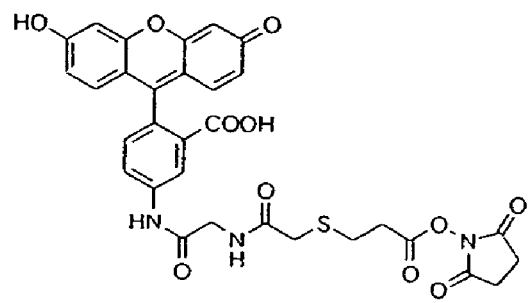
Figure 9D:
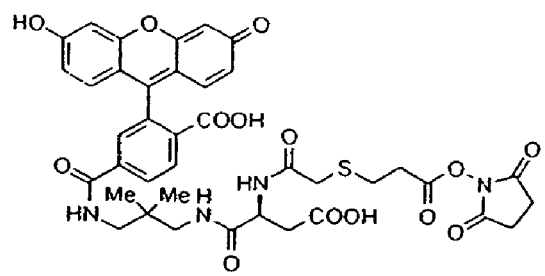
Figure 9D:
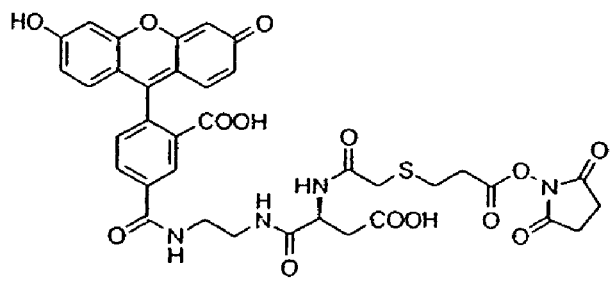

The compounds of this reaction are shown in FIG. 9D.

Synthesis of Compound 7

To a stirred solution of 5-(bromomethyl)fluorescein (compound 6) (40 mg, 0.095 mmol) in dry DMF (5 mL) were added triethylamine (15 μL, 0.108 mmol) and 3-mercaptopropionic acid (10 μL, 0.115 mmol). The resulting solution was stirred at room temperature for 2 days. TLC (40:9:1 $CH_2Cl_2$-MeOH—$H_2O$) indicated completion of the reaction. The reaction solution was evaporated under reduced pressure. Finally, flash chromatography employing 30:1 and 25:1 $CH_2Cl_2$-MeOH as eluant provided the β-thioacid (compound 7) (28 mg, 66%).

Synthesis of Pro5

To a solution of the acid (compound 7) (27 mg, 0.060 mmol) in dry DMF (2 mL) were added N-hydroxysuccinimide (11 mg, 0.096 mmol) and 1,3-dicylcohexylcarbodiimide (20 mg, 0.097 mmol). The reaction mixture was stirred at room temperature under nitrogen for 2 days at which time TLC (9:1 $CH_2Cl_2$-MeOH) showed complete disappearance of the starting material. Removal of the solvent under reduced pressure and subsequent flash chromatography with 30:1 $CH_2Cl_2$-MeOH afforded Pro5 (24 mg, 73%).

Preparation of Pro14

Figure 9E:
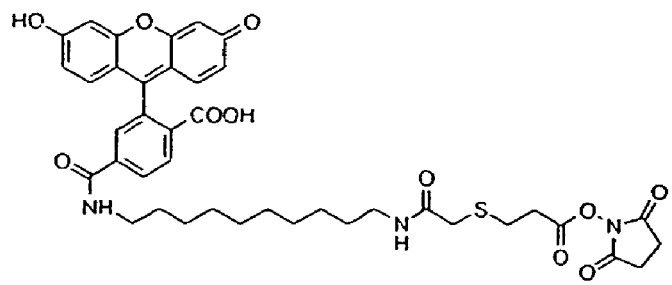
Figure 9E:
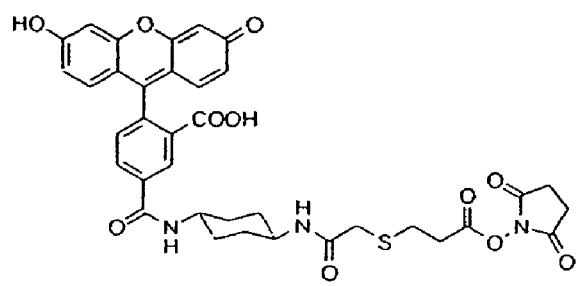
Figure 9E:
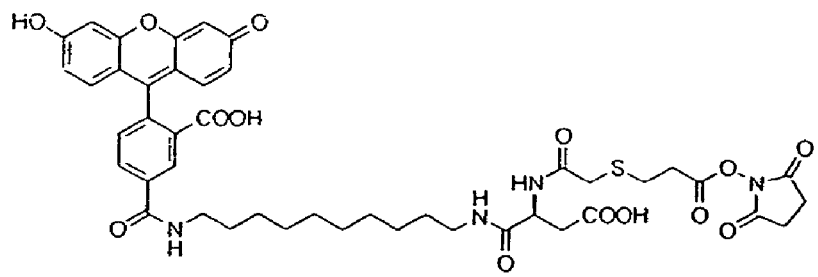
Figure 9E:
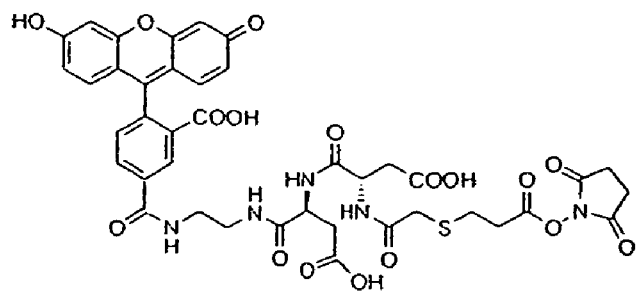
Figure 9F:
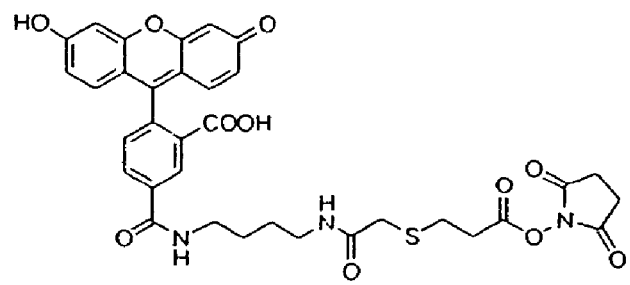
Figure 9F:
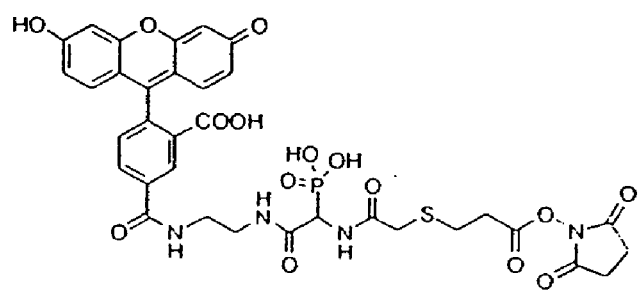
Figure 9F:
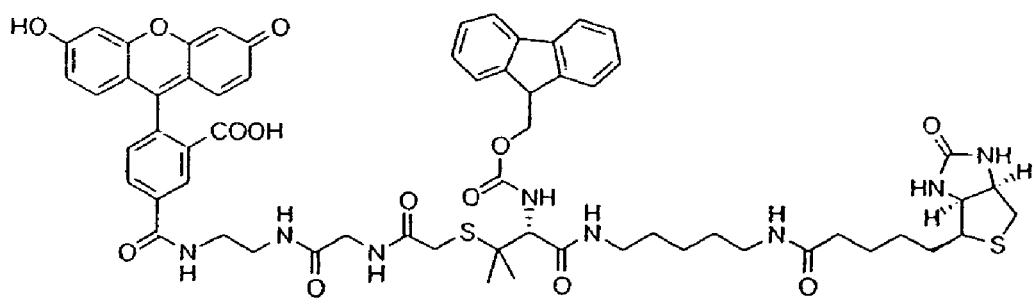
Figure 9F:
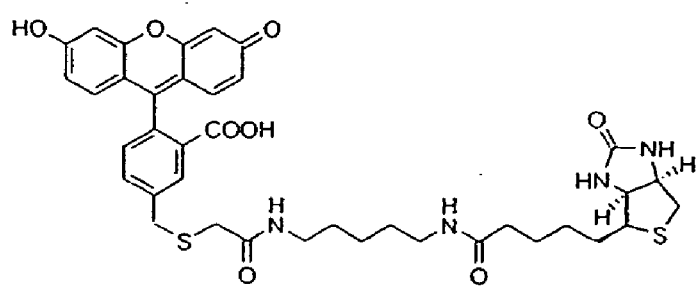
Figure 9G:
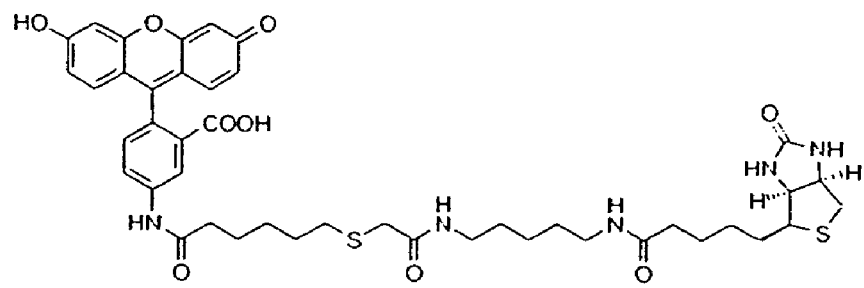
Figure 9G:
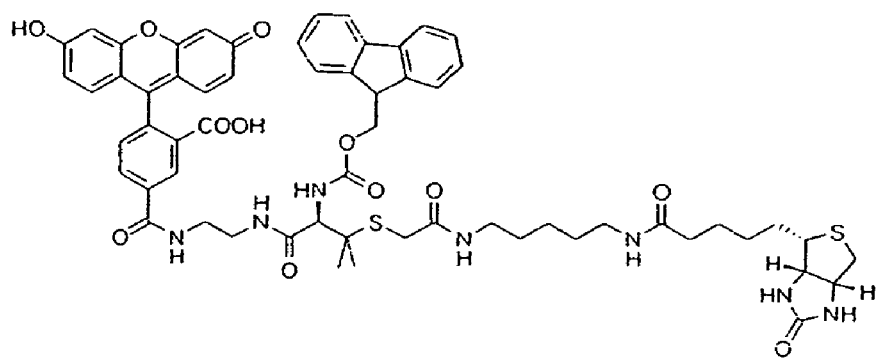
Figure 9G:
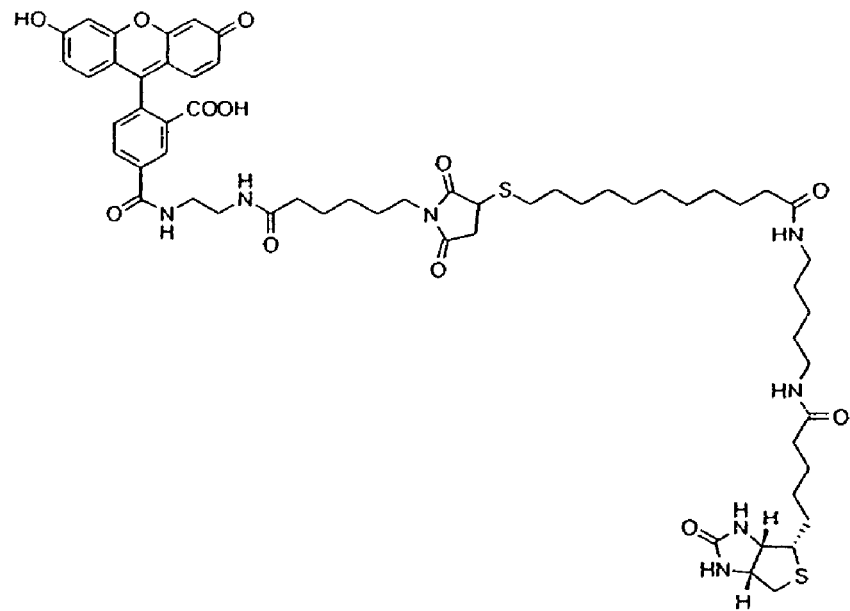
Figure 9H:
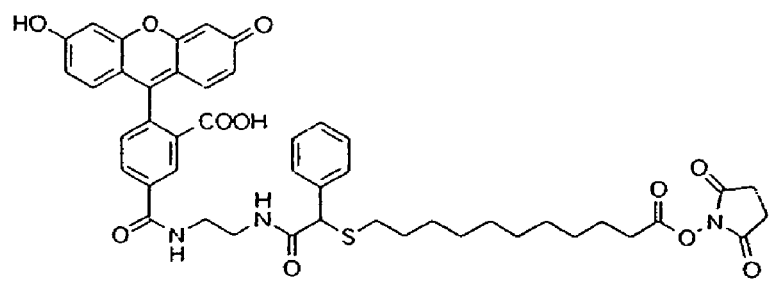
Figure 9H:
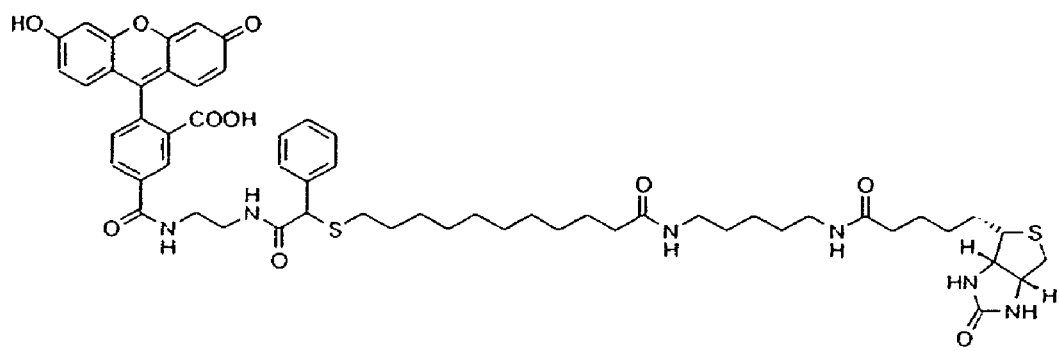
Figure 9H:
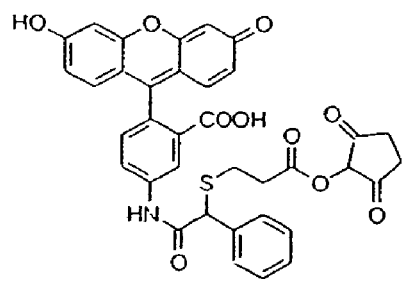
Figure 9H:
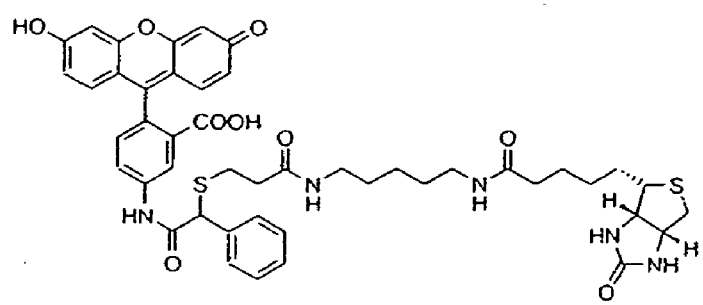
Figure 9I:
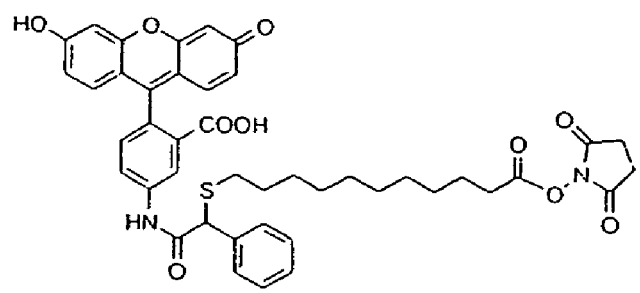
Figure 9I:
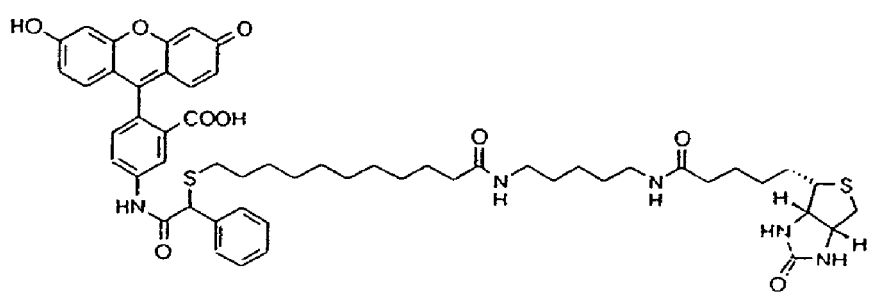
Figure 9I:
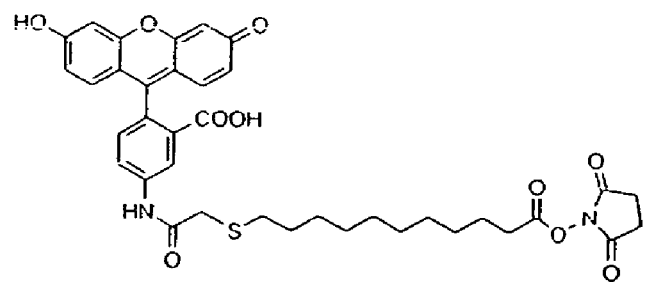
Figure 9I:
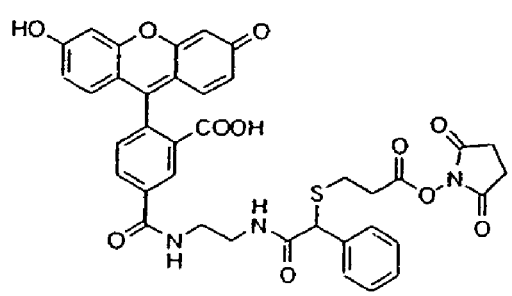
Figure 9J:
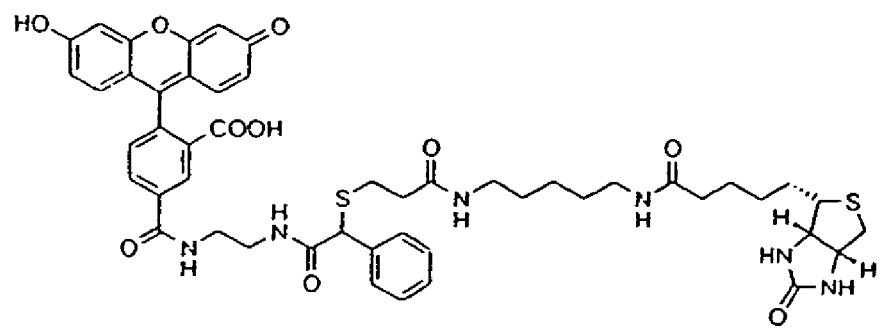
Figure 9J:
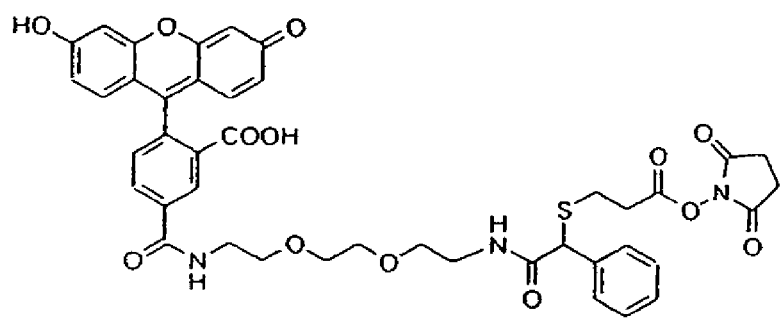
Figure 9J:
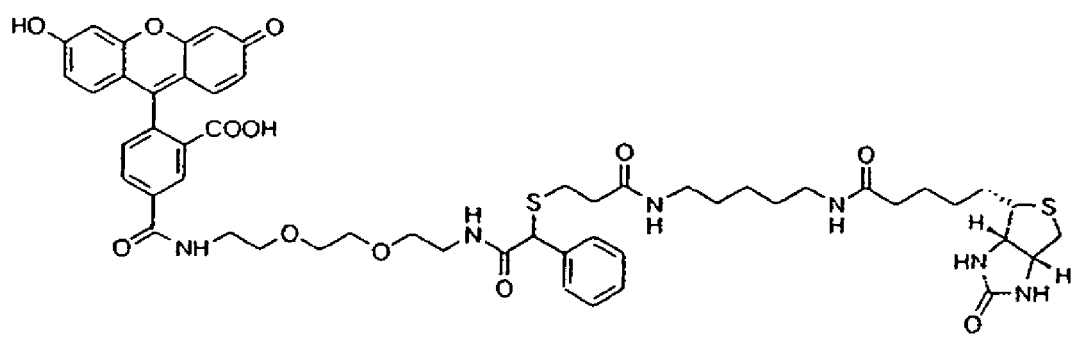
Figure 10A:
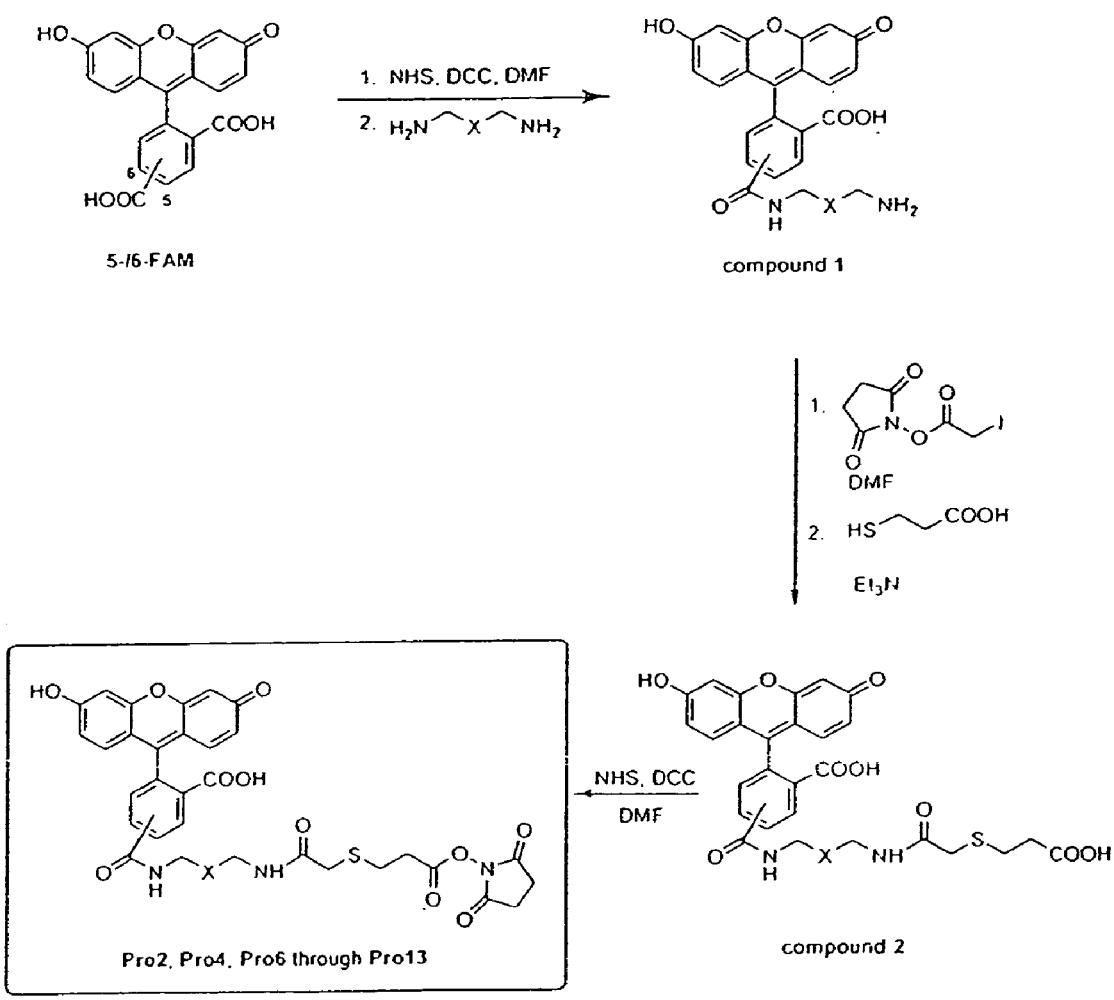
FIGS. 10A–I illustrate the chemistries of synthesis of the e-tag moieties illustrated in FIG. 9.
Figure 10B:
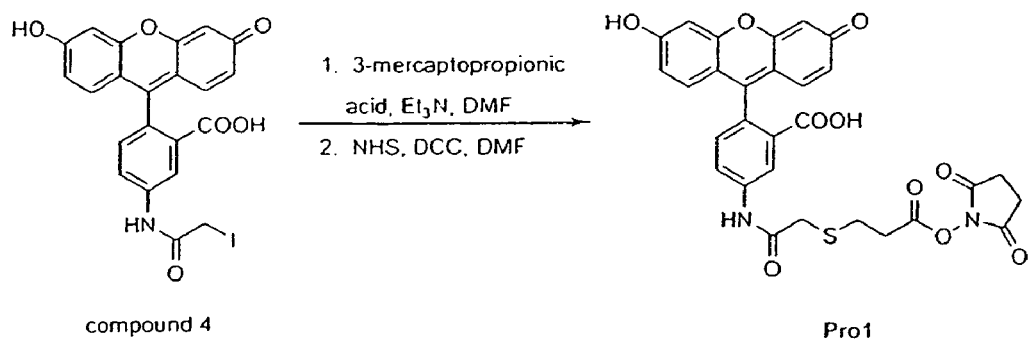
Figure 10C:
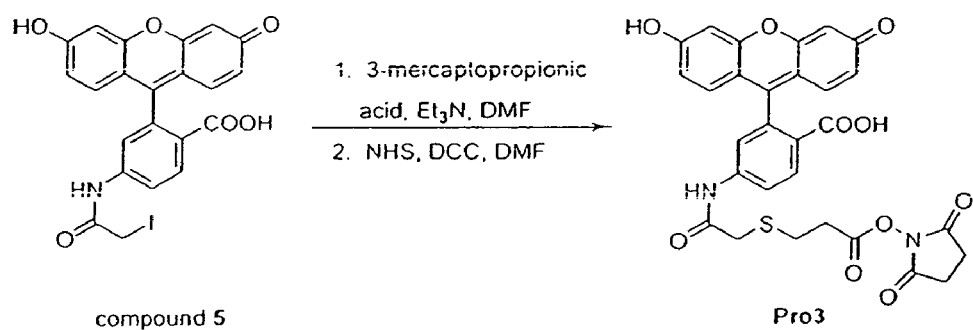
Figure 10D:
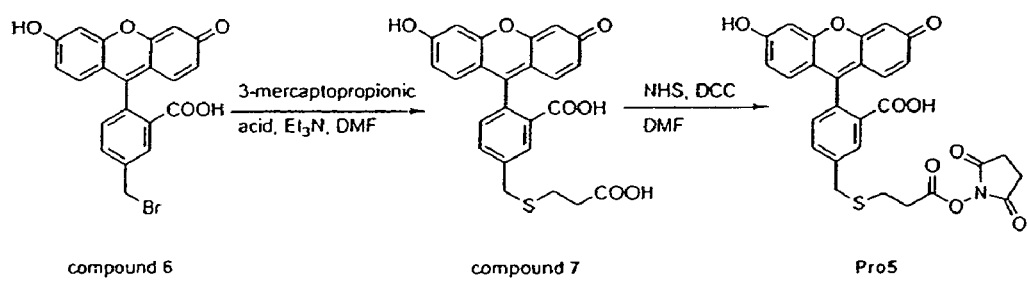
Figure 10E:
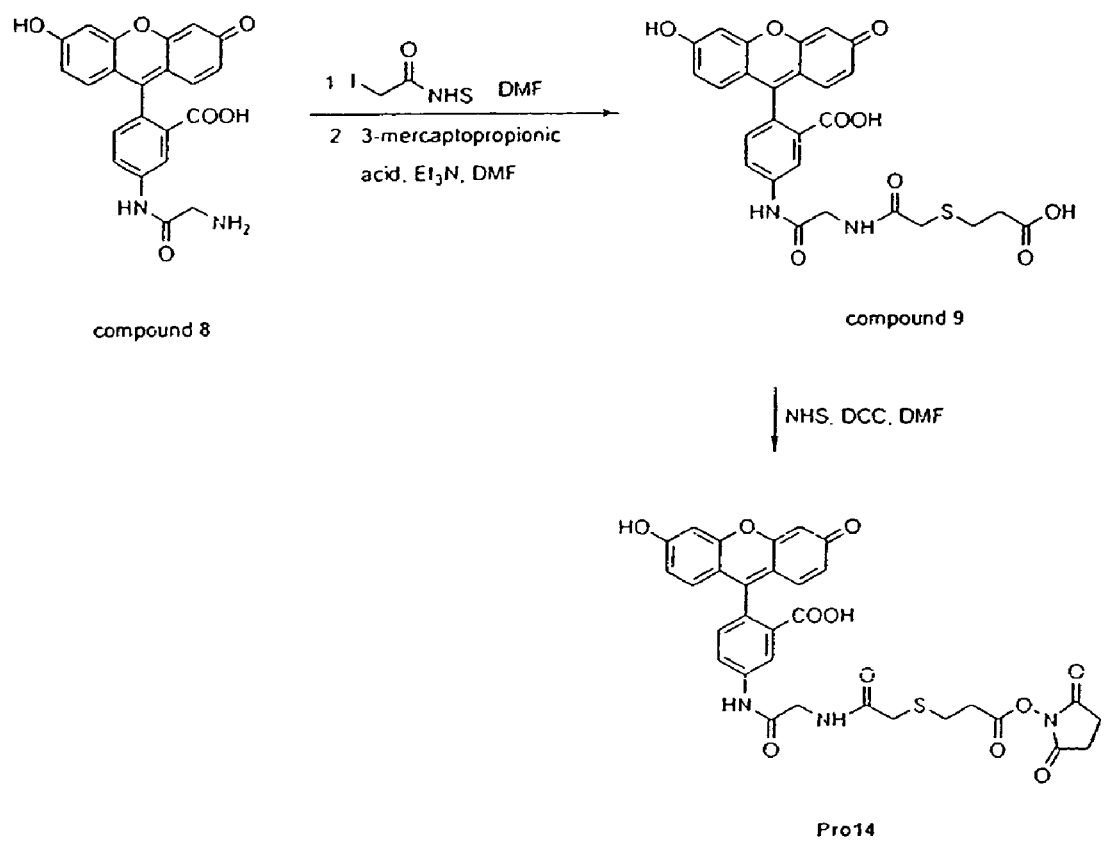
Figure 10F:
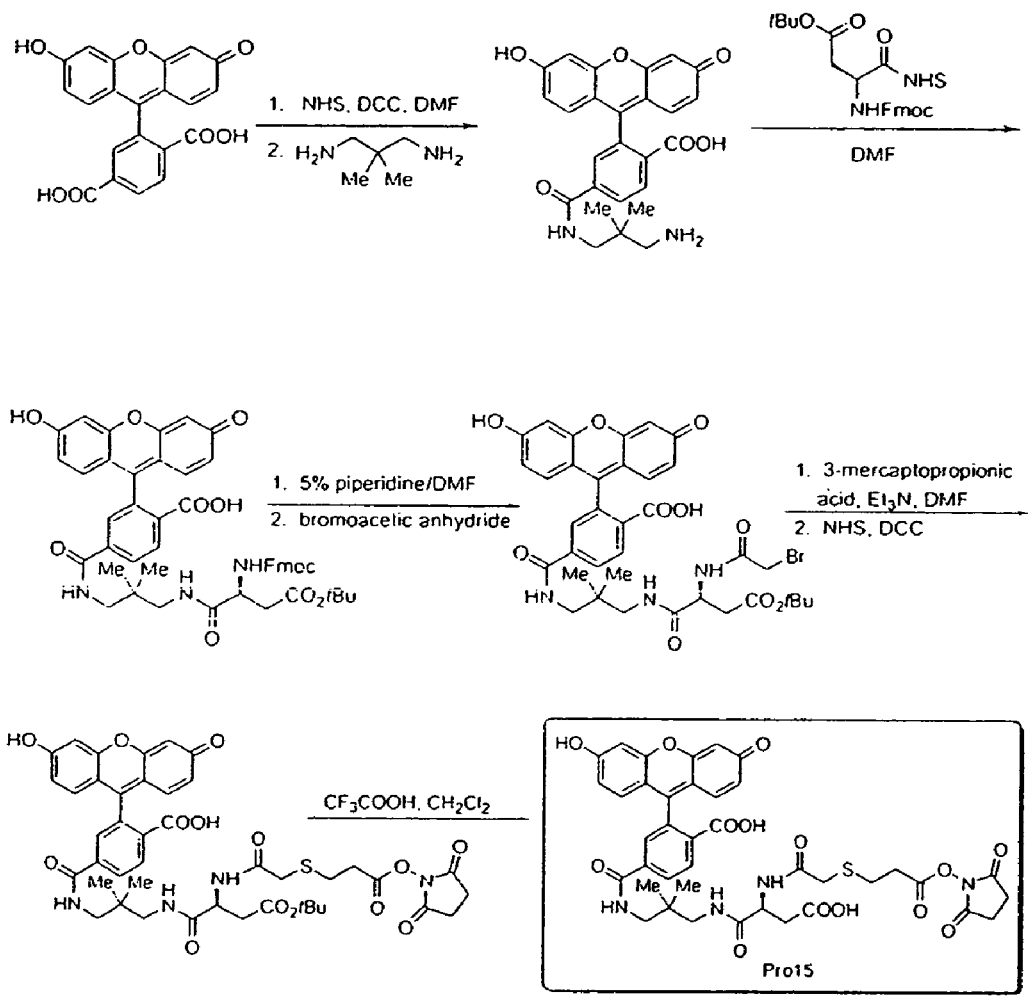
Figure 10G:
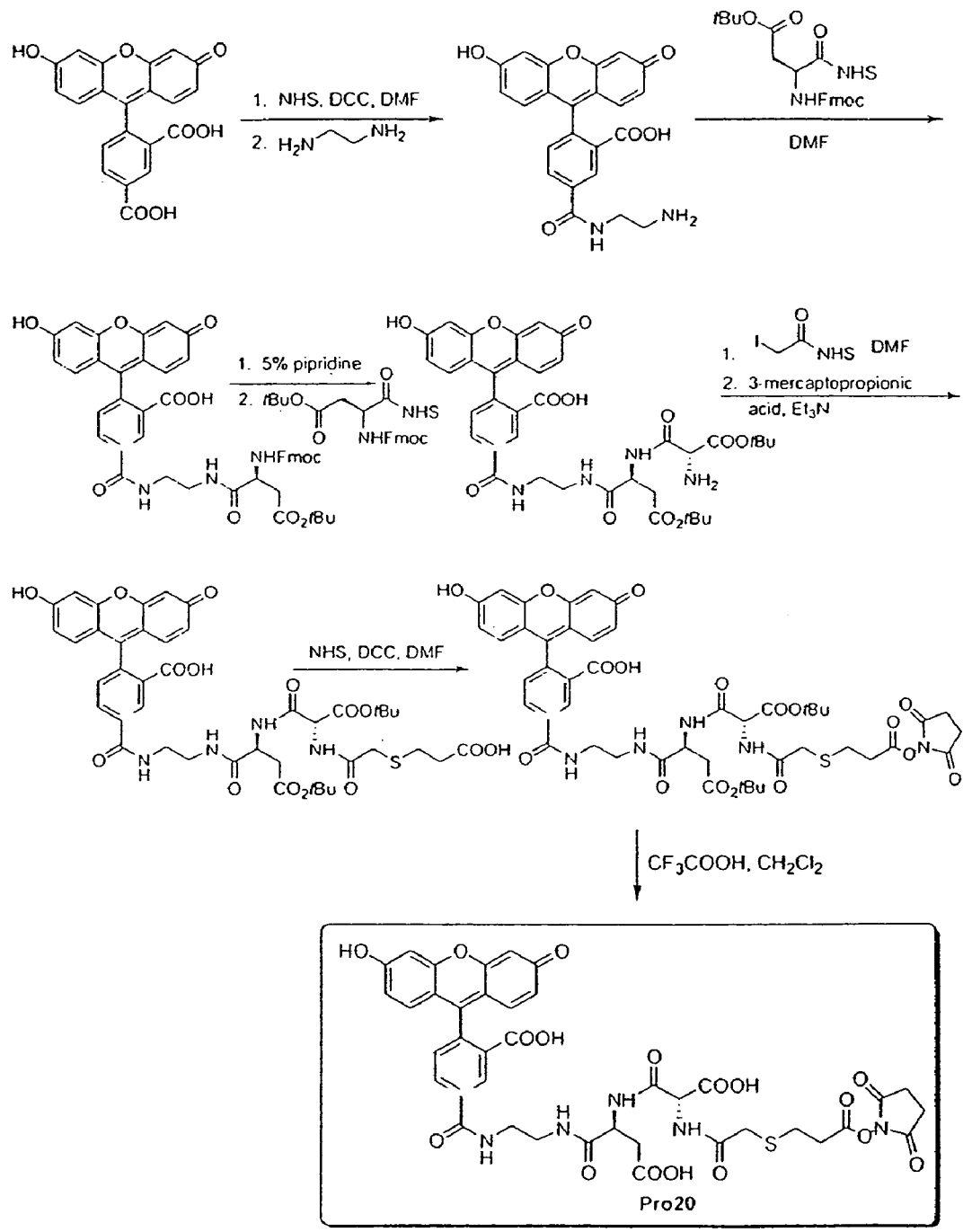
Figure 10H:
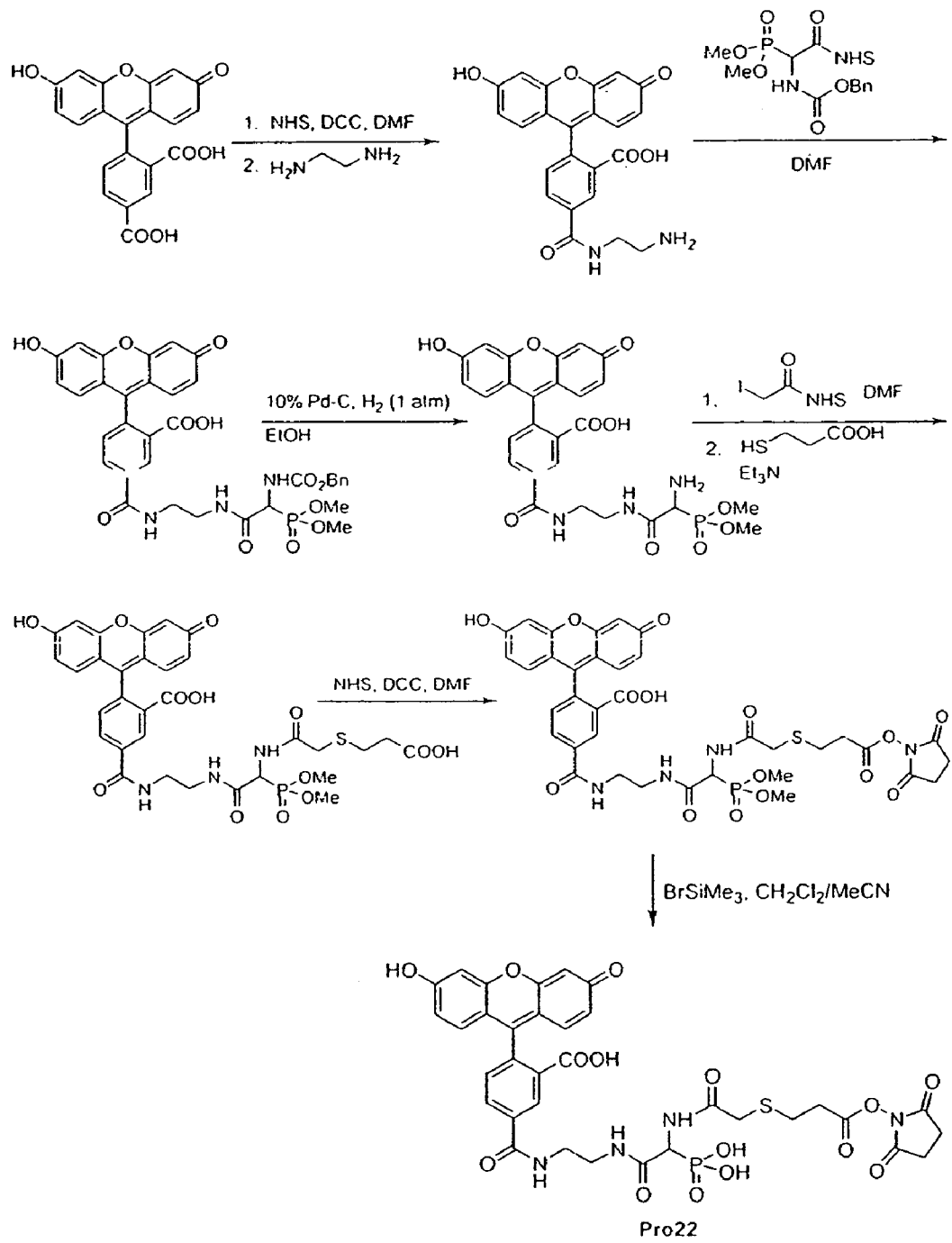
Figure 10I:
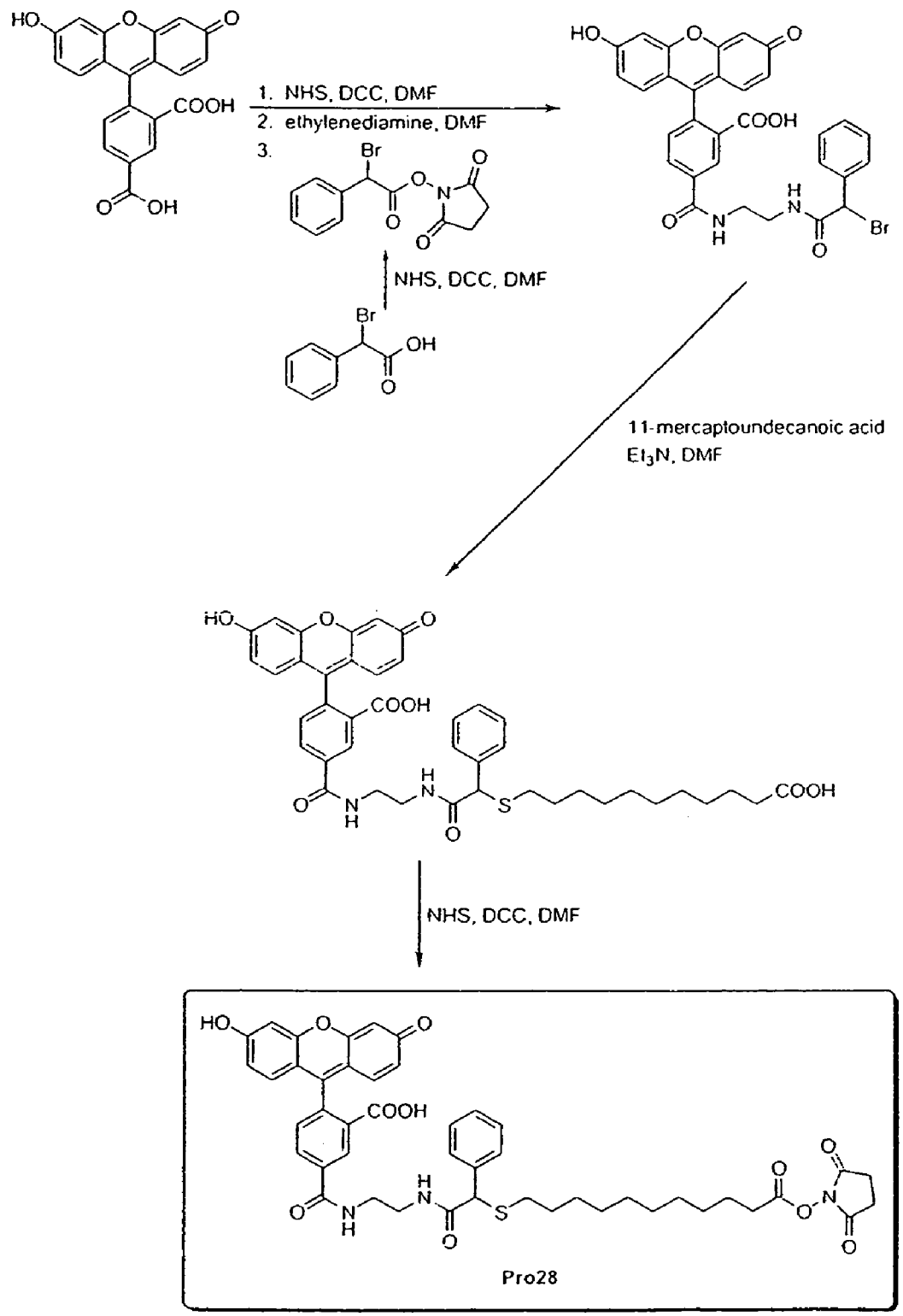

The compounds of this reaction are shown in FIG. 9E.

Synthesis of Compound 9

To 5-aminoacetamidofluorescein (compound 8) (49 mg, 0.121 mmol) were sequentially added dry DMF (4 mL) and N-succinidyl iodoacetate (52 mg, 0.184). A clear solution resulted and TLC (40:9:1 $CH_2Cl_2$-MeOH—$H_2O$) indicated complete disappearance of the starting material.

The above reaction solution was then treated with triethylamine (30 μL, 0.215 mmol) and 3-mercaptopropionic acid (30 μL, 0.344 mmol). The resulting mixture was stirred for 2 h. Removal of the solvent under reduced pressure followed by flash chromatography using 20:1 and 15:1 $CH_2Cl_2$-MeOH as eluant gave the β-thioacid (compound 9) (41 mg, 62%). The structural assignment was made on the basis of $^1$NMR (300 MHz, DMSO-$d_6$).

Synthesis of Pro14

To a stirred solution of compound 9 (22 mg, 0.04 mmol) in dry DMF (2 mL) were added N-hydroxysuccinimide (9 mg, 0.078 mmol) and 1,3-dicylcohexylcarbodiimide (16 mg, 0.078 mmol). The resulting solution was stirred at room temperature under nitrogen for about 24 h. The reaction mixture was concentrated under reduced pressure and the residue purified by flash chromatography using 30:1 and 20:1 $CH_2Cl_2$-MeOH as eluant to give Pro14 (18 mg, 70%).

Synthesis of Pro15, Pro20, Pro22, and Pro28

The synthesis schemes for producing NHS esters of molecular tags Pro15, Pro20, Pro22, and Pro28 are shown in FIGS. 16 F–I, respectively. All of the reagent and reaction conditions are conventional in the art and proceed similarly as the reactions described above.

Example 3

Characterization of Cell Surface Receptor Binding

Using a Protein-Molecular Tag Conjugate

To demonstrate that the amount of probe tag released is related to total number of receptors in the cell sample, a ligand-receptor assay like that described in Section II above was carried out by adding a fixed amount (about 55 nM) protein probe (TNF-tag) added to samples containing increasing numbers of target cells (U937 cells) that respond to TNF. In each sample, the probe was incubated with the cells for 60 minutes, then the sample irradiated at 640–700 nm to release bound etags. The sample was separated by capillary electrophoresis, and the amount of released probe from each sample quantitated as area under the curve. In this, and the assays described below, the cells were initially modified to contain a cell-surface sensitizer agent.

Figure 17:
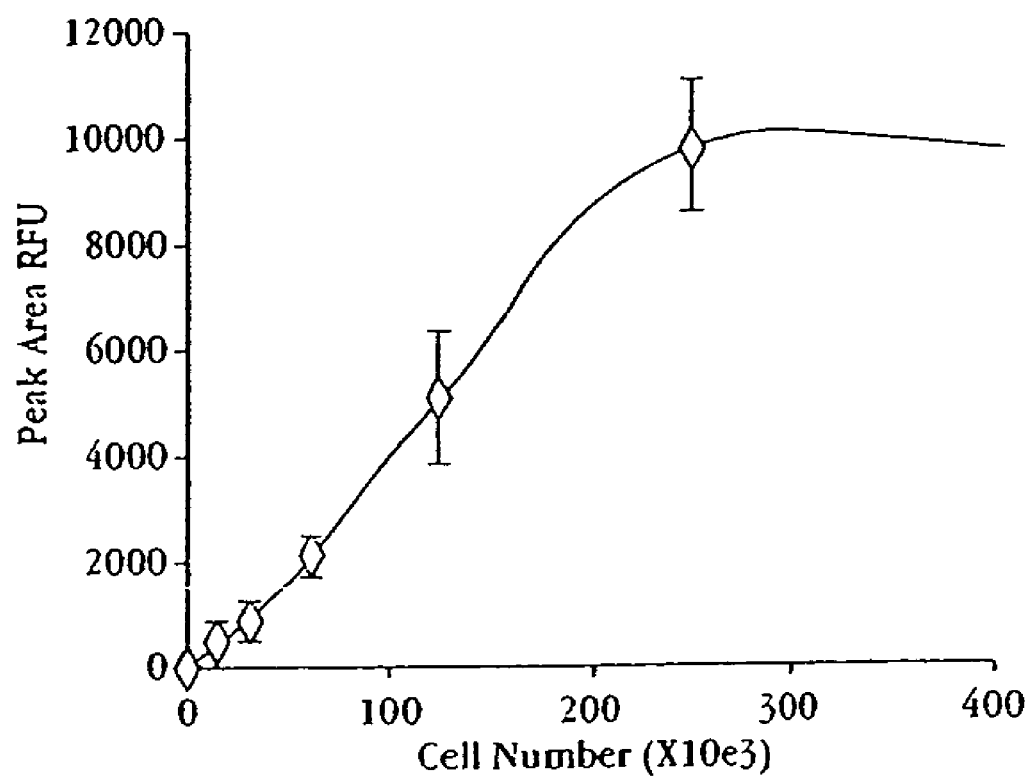
FIG. 17 is a plot of peak area of a molecular tag released from a TNF-molecular tag probe on binding to U937 cells, as a function of number of cells in the assay.

The results are plotted in FIG. 17, which shows the detected level of a molecular tag, expressed as RFU (relative fluorescence units), plotted as a function of numbers of sample cells. As seen, there is a linear relationship between number of cells (and therefore, number of cell receptor) and the total number of probes bound, as evidence by released tags, below receptor saturation. Knowing the concentration of added probe, and the number of cells in a sample, the approximate number of receptors per cell can be determined. According to an important advantage of the invention, the method is sensitive to as few as 200–300 receptors/cell.

Figure 18A:
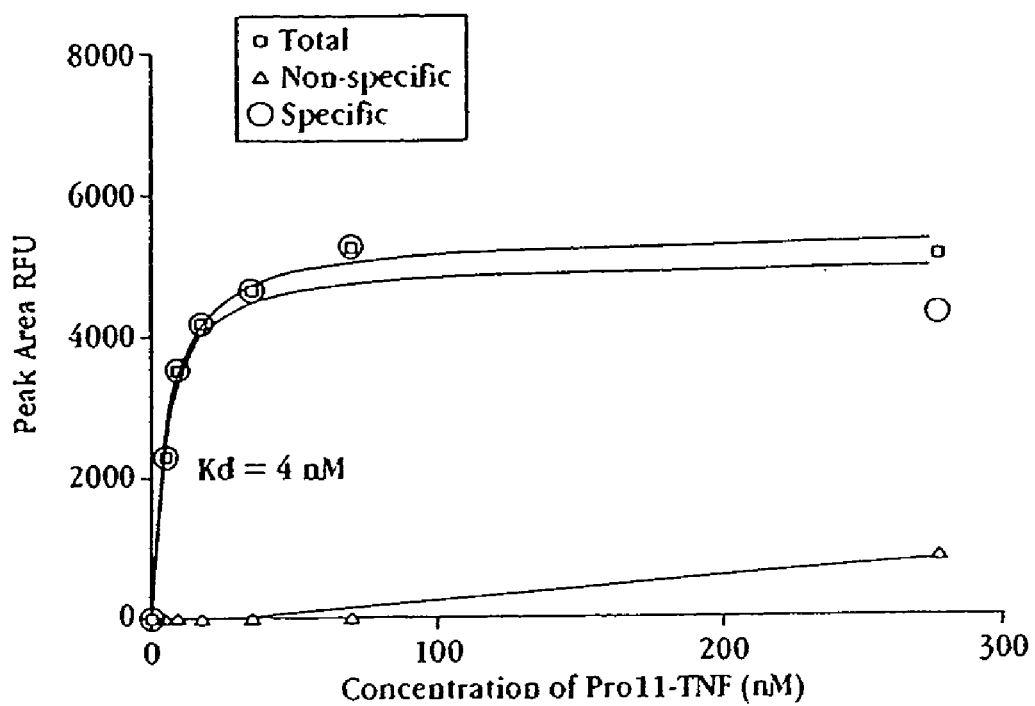
FIGS. 18A and 18B are plot of peak area of an molecular tag released from a TNF-molecular tag probe on binding to U937 cells (18A), and CD40L molecular tag probe from THP-1 cells (18B), as a function of probe concentration.

A receptor density determination can also be made, in accordance with the invention, by a competitive binding study in which protein probe competes with native protein for binding to target cells. To illustrate this method, a multi-sample assay was conducted by mixing fixed numbers of target U937 cells, a 50-fold excess of native TNF, and increasing concentrations of TNF-molecular tag conjugate. The plot in FIG. 18A shows a calculated Kd, determined from the midpoint of the receptor-binding curve, is about 4 nM. Bmax, as determined from the maximum of the binding curve normalized to internal reference, is about $1 \times 10^3$ receptors/cell, consistent with the results found from FIG. 17.

Figure 18B:
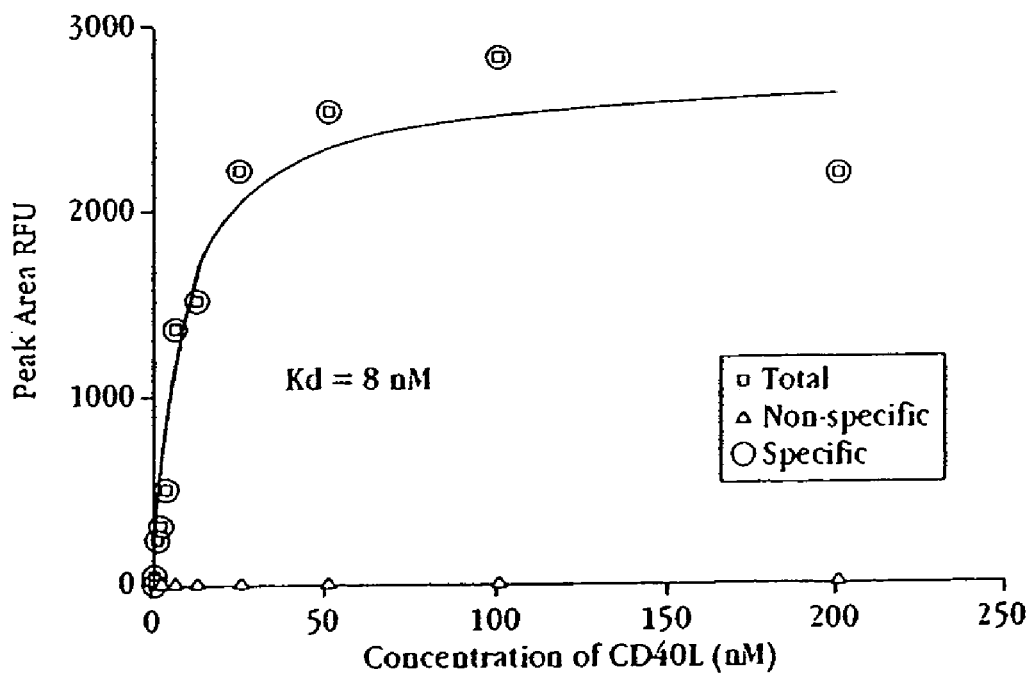

A similar assay was carried out to measure release of a CD40L protein probe from THP-1 cells. The results, presented in FIG. 18B, show a calculated number of receptors/cell about half that calculated from TNF receptors on U937 cells, and a Kd of about twice that for TNF binding to U937 cells.

Figure 19:
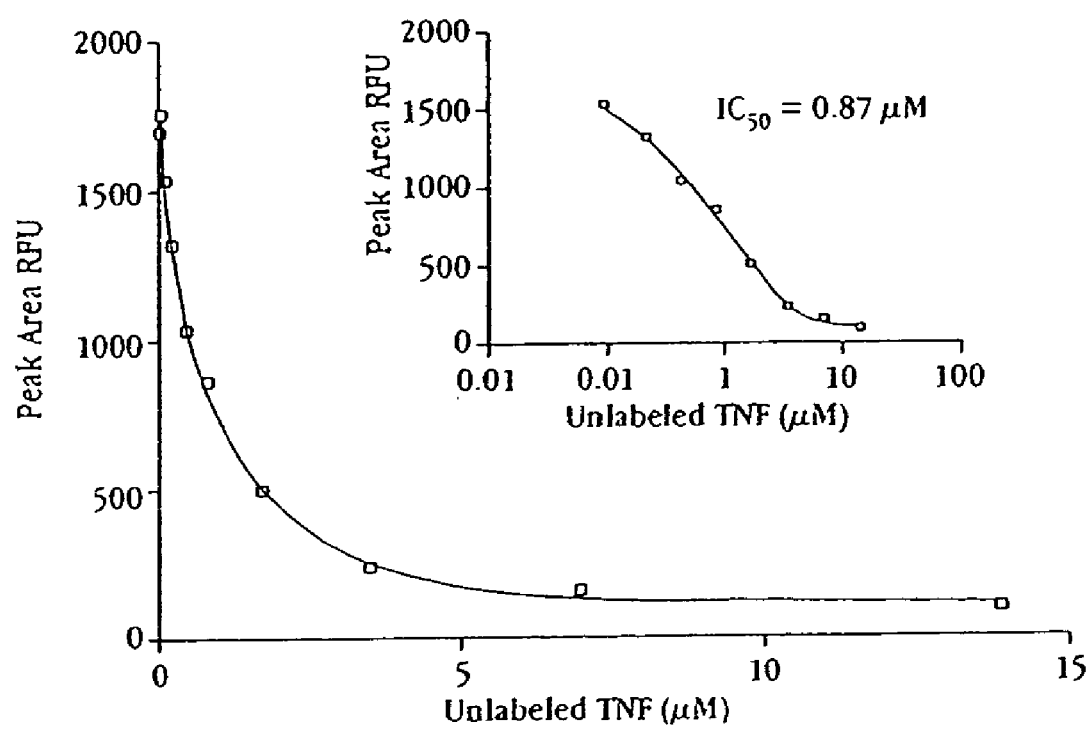
FIG. 19 is of a plot of peak area of a molecular tag released from a TNF-molecular tag probe on binding to U937 cells, as a function of amount of native TNF added to the cells.

As mentioned above, the assay can also be used to examine the ability of test compounds to modulate, e.g., inhibit the binding of protein probe to its receptor. This assay is illustrated by a study in which a fixed number of U937 cells ($5 \times 10^4$) was mixed with a fixed concentration of TNF-molecular tag conjugate (277 nM) and each of increasing amounts of native TNF (as a competitive inhibitor). The plot shown in FIG. 19, and particularly the expanded inset plot, shows that unlabeled TNF displaces half the bound TNF probe at an added concentration of about 870 nM.

Figure 20:
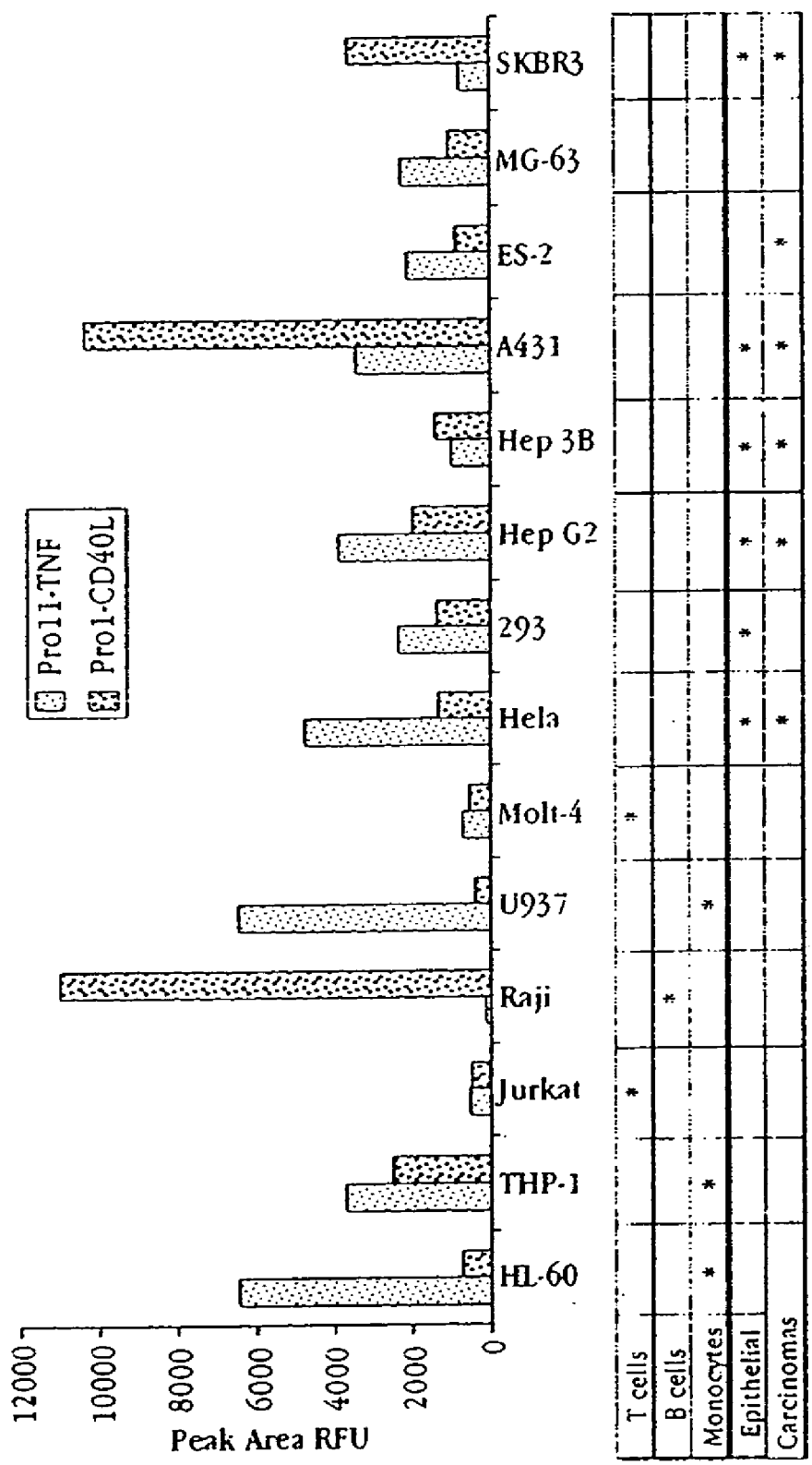
FIG. 20 illustrates levels of detected binding of a TNF secreted-protein probe (light bars) and a CD40L secreted-protein probe (dark bars) to various type of T cells, B cells, monocytes, epithelial cells, and carcinoma cells, as indicated.

To demonstrate the ability to perform multiplexed reactions with different probes in different cell lines, protein probes for TNF and CD40L secreted proteins were added to each of a plurality of different T cells, B cells, monocytes, epithelial cells, and carcinoma cells, as indicated in FIG. 20. For each cell type, the released molecular tags for both probes were analyzed in a single separation format, and the peak areas compared, with the results shown in FIG. 20. As seen, the CD40L probe showed high relative binding levels in Raji, A43 1, and SKBR3 cells; the TNF probe showed dominant relative binding in many other cells, and a few cells showed low levels of both receptors.

It will be appreciated that assays of the type described above can be carried out in singleplex form, where each sample contains a different concentration of reagents, and each probe (which may be identical in all sample) is individually separated, detected, and quantitated. Alternatively, each of the different sample may contain a protein probe with a different etag, allowing the released tags from all of the samples to be separated and quantitated in a single electrophoresis-medium format. The latter approach provides an internal control for variations in tag recovery and detection efficiency.

The method is sensitive for detecting a few hundred receptors/cell, and gives a linear response up to 100,000 receptors/or more. The method also provides simple determination of binding affinity, with relatively little shift due to the presence of tags.

Figure 21A:
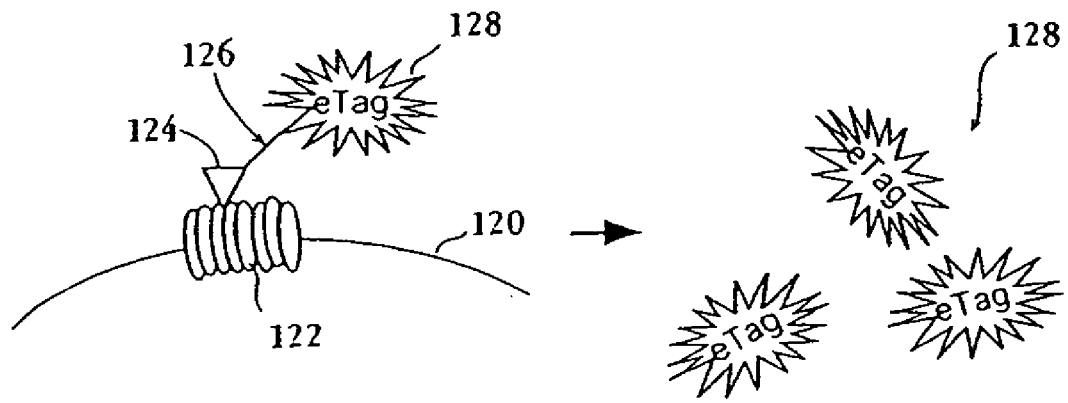
FIGS. 21A and 21B illustrate the application of the invention to screening test compounds for their capable to inhibit binding between a secreted protein and its receptor.
Figure 21B:
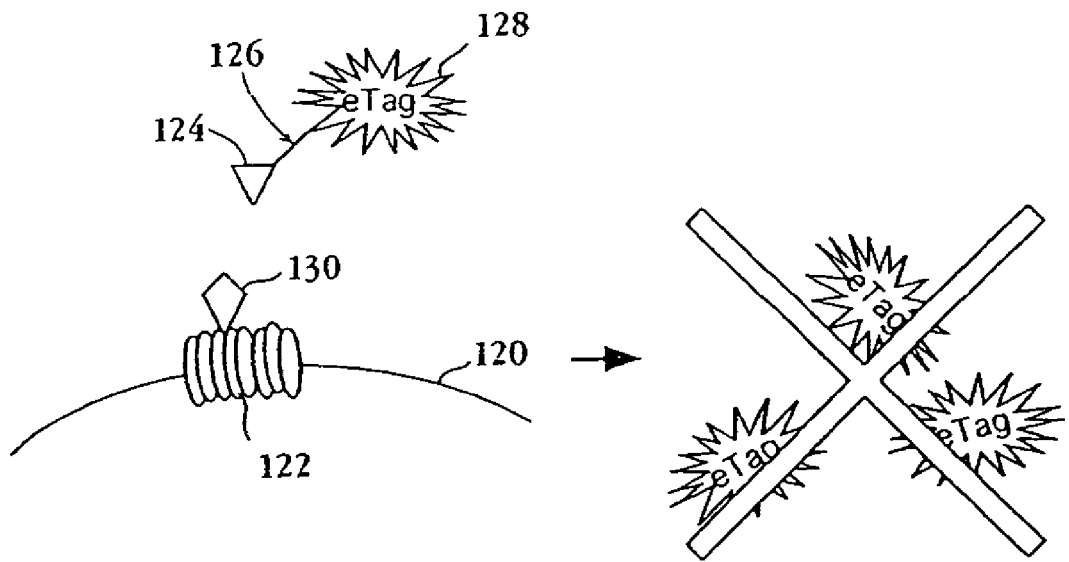

As indicated above, the method is readily adapted to screening a plurality of test compounds for their ability to modulate, e.g., enhance or inhibit, the binding of an secreted-protein ligand to its receptor, e.g., cell-surface receptor. The method is illustrated in FIGS. 21A and 21B, which shows a target cell 120 having a surface receptor 122 that can bind to a protein ligand 124. The purpose of the assay is to test a plurality of compounds for their ability to alter the extent of ligand binding to the receptor, for example, as part of a drug-discovery program to find a compound capable of interfering with ligand-receptor binding.

FIG. 21A illustrates the assay in the absence of test compounds, where binding of a protein probe 126 to its receptor, and subsequent surface-specific cleavage released probe tags, such as tag 128, in proportion to the amount of probe bound.

In FIG. 21B, the target cell or cells are first mixed with a test compound 130 which may bind to receptor 122, as indicated. When protein probe is now added, probe binding to the receptor may be inhibited, either partially or completely, depending on the relative concentrations of probe and test compound, and the relative affinities of the two for the receptor.

In a preferred embodiment, a plurality of cell samples, e.g., in a microtitre-plate format, are each mixed with a different test compound or with a different concentration of the same test compound, and the probe added to each sample has a different etag moiety. Following the binding and cleavage reactions, the reaction mixtures are combined and the combined released etags then separated and detected in a single-separation format. Where each sample contains a different test compound, the relative effect of each of a plurality of such compounds on ligand-receptor binding can be determined from a single electropherogram. Where each sample contains a different concentration of the same test compound, the relative binding affinity and range of effective compound concentrations can be determined from a single electropherogram.

The assay methods above are useful in identifying orphan secreted protein that bind to target receptors, the nature of the cells containing target receptors, the binding affinity of the protein for its receptor, and compounds that may modulate ligand-receptor binding.

Ultimately, to deconvolve an orphan secreted protein, it is important to identify the receptor(s) to which the orphan protein binds. In accordance with one aspect of the invention, this can be done by adapting the assay and reagents to isolating cell-bound receptors, as a necessary step toward analyzing the primary amino acid sequence and ultimately identifying the receptor.

Figure 22A:
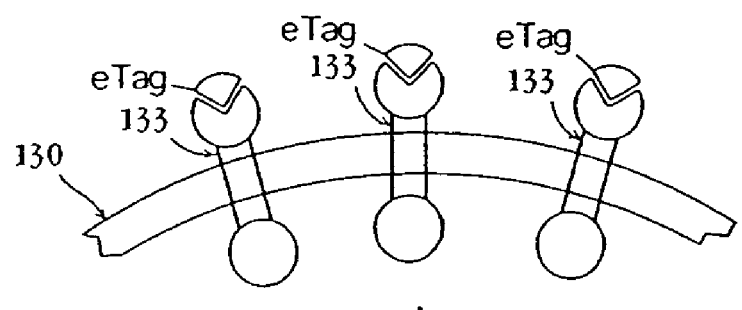
FIGS. 22A–22C illustrates steps in isolating and identifying a cell-surface receptor to which a secreted protein binds, in accordance with a further embodiment of the invention.
Figure 22B:
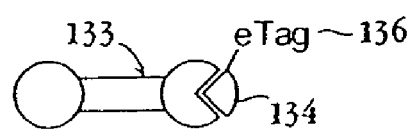
Figure 22B:
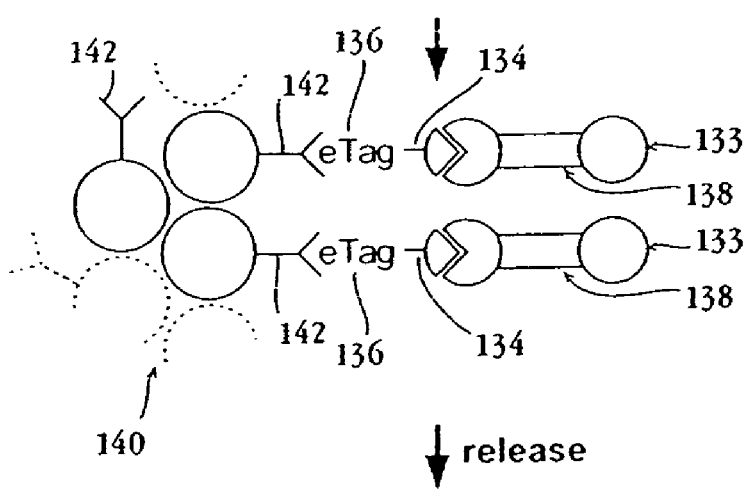
Figure 22C:

With reference to FIG. 22A–22C, the method utilizes cells that have been identified, as above, to have surface receptors, such as receptors 133, that bind specifically to the orphan protein of interest. Preferably a cell having a fairly high surface density of receptors, e.g., over 1,000/cell can be identified, although this is not critical. The identified cells, indicated at 132, are mixed, as above, with a protein probe 134 having a selected etag moiety 136 linked to the protein, although not necessarily by a cleavable linkage. After binding, the cells are treated under gently lysing conditions, e.g., by the addition of a non-ionic detergent, according to known lysing procedures to solubilize the receptor in the cell membrane. This treatment releases a probe-receptor complex 138 (FIG. 22B) as part of the cell lysate.

The lysate is now passed over a solid-phase medium 140, e.g., a particle bed having surface bound antibodies, such as antibodies 142 specific against the probe etag. As indicated in FIG. 22B, the affinity chromatography is effective to capture the solubilized receptor-probe complex. After washing the particle bed to remove unbowed material, the receptor can be released from the solid support, either by cleaving the linker, or preferably, by exposing the complex to salt or pH conditions effective to break the complex, according to known methods.

The isolated receptor may now be identified by conventional methods that may include (I) amino acid analysis, (ii) protease digest, e.g., tryptic digest, with identification of the digest particles, e.g., by mass spectroscopy, to determine primary sequence, and (iii) SDS gel electrophoresis to determine subunit composition and size. With this information, it may be possible to deduce the role or class of the receptor, and thus the role or class of the secreted protein.

What is claimed is:

1. A composition for determining the presence or absence of one or more membrane-associated analytes, the composition comprising:

a sensitizer-treated membrane containing one or more membrane associated analytes, the sensitizer-treated membrane comprising a cell surface membrane having photosensitizers attached, the photosensitizers each having a lipophilic moiety for anchoring the photosensitizers in the cell surface membrane; and one or more binding compounds, such that there is at least one binding compound specific for each of the one or more membrane-associated analytes, each binding compound having one or more molecular tags, each molecular tag being attached by a cleavable linkage, and the molecular tags of each binding compound being distinguishable from those of every other binding compound by one or more physical and/or optical characteristics;

wherein at least one binding compound of the plurality is specifically bound to at least one membrane-associated analyte.

2. The composition of claim 1 wherein said one or more membrane-associated analytes are selected from the group consisting of G-protein coupled receptors "GPCRs."

3. The composition of claim 1 wherein said one or more binding compounds each comprises an antibody composition.

4. The composition of claim 3 wherein said antibody composition is a monoclonal antibody or a polyclonal antibody composition.

5. The composition according to claims 1, 2, 3, or 4 wherein said one or more binding compounds is a plurality of said binding compounds in the range of from 2 to 50 and wherein said one or more physical characteristics is electrophoretic mobility.

6. The composition of claim 5 wherein said molecular tags upon cleavage from different said binding compounds form distinct peaks in an electropherogram.

* * * * *